US010177316B2

(12) United States Patent
Zeng et al.

(10) Patent No.: US 10,177,316 B2
(45) Date of Patent: Jan. 8, 2019

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Walter Yeager, Yardley, PA (US); Scott Joseph, Ewing, NJ (US); Alexey Borisovich Dyatkin, Ambler, PA (US); Gregg Kottas, Ewing, NJ (US); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 232 days.

(21) Appl. No.: 14/990,321

(22) Filed: Jan. 7, 2016

(65) Prior Publication Data

US 2016/0233435 A1  Aug. 11, 2016

Related U.S. Application Data

(60) Provisional application No. 62/113,774, filed on Feb. 9, 2015.

(51) Int. Cl.
| | | |
|---|---|---|
| *H01L 51/00* | (2006.01) | |
| *C09K 11/02* | (2006.01) | |
| *C09K 11/06* | (2006.01) | |
| *C07D 487/06* | (2006.01) | |
| *H01L 51/50* | (2006.01) | |

(52) U.S. Cl.
CPC ........ *H01L 51/0072* (2013.01); *C07D 487/06* (2013.01); *C09K 11/025* (2013.01); *C09K 11/06* (2013.01); *H01L 51/0067* (2013.01); *H01L 51/0073* (2013.01); *H01L 51/0074* (2013.01); *C09K 2211/1007* (2013.01); *C09K 2211/1029* (2013.01); *C09K 2211/185* (2013.01); *H01L 51/5072* (2013.01); *H01L 51/5096* (2013.01)

(58) Field of Classification Search
CPC ............ H01L 51/0072; H01L 51/0074; H01L 51/5096; H01L 51/5072; H01L 51/0067; H01L 51/0073
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Golam Mowla
(74) *Attorney, Agent, or Firm* — Duane Morris LLP

(57) ABSTRACT

A novel compounds useful as hosts for phosphorescent emitters in OLEDs is disclosed.

15 Claims, 2 Drawing Sheets

(56) References Cited

U.S. PATENT DOCUMENTS

| | | |
|---|---|---|
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0051928 A1 | 3/2010 | Fukuzaki |
| 2012/0075273 A1 | 3/2012 | Abe et al. |
| 2012/0292576 A1 | 11/2012 | Parham et al. |
| 2014/0034914 A1 | 2/2014 | Takada et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2012191031 | 10/2012 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011128017 | 10/2011 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., Apr. 30, 2007, 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhigiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato)beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

(56) References Cited

OTHER PUBLICATIONS

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)indium(III) Derivatives," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater, 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Nong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

ORGANIC ELECTROLUMINESCENT MATERIALS AND DEVICES

CROSS-REFERENCE TO RELATED APPLICATIONS

This application claims priority to U.S. Provisional Application Ser. No. 62/113,774, filed Feb. 9, 2015, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and to organic materials used in such devices. The compounds are expected to improve phosphorescent OLED performance.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

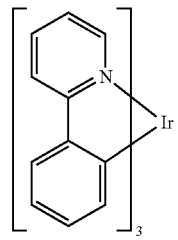

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a new compound having the formula:

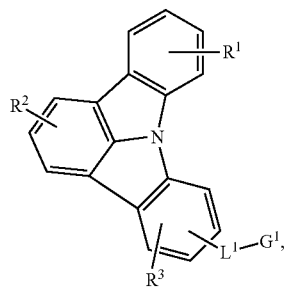

Formula I is disclosed;

wherein $L^1$ is selected from the group consisting of a direct bond, phenyl, biphenyl, terphenyl, fluorene, carbazole, pyridine, pyrimidine, pyrazine, pyridazine, triazine, naphthalene, anthracene, and combinations thereof;

wherein $G^1$ is selected from the group consisting of:

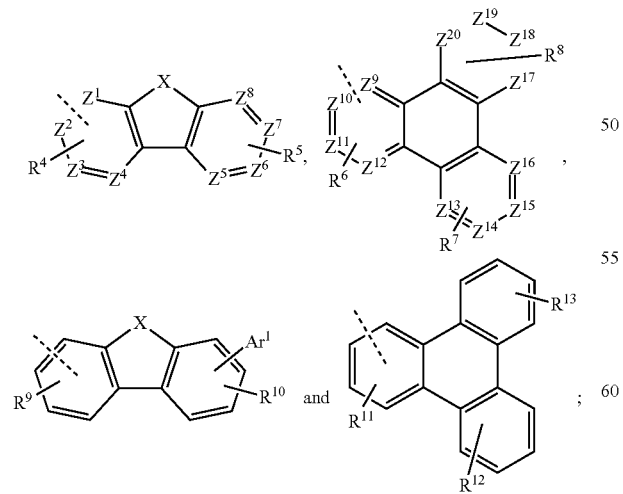

wherein X is selected from the group consisting of oxygen, sulfur, and selenium;

wherein $R^1$, $R^5$, $R^7$, $R^8$, $R^{12}$, and $R^{13}$ each independently represent mono, di, tri, or tetra substitution, or no substitution;

wherein $R^2$, $R^3$, $R^4$, $R^5$, $R^6$, $R^9$, $R^{10}$, and $R^{11}$ each independently represent mono, di, or tri substitution, or no substitution;

wherein $R^1$ to $R^{13}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;

wherein $Z^1$ to $Z^{20}$ are each independently selected from the group consisting of carbon and nitrogen;

wherein at least one of $Z^1$, $Z^2$, $Z^3$, $Z^4$, $Z^5$, $Z^6$, $Z^7$, and $Z^8$ is nitrogen; and at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$, and $Z^{20}$ is nitrogen;

wherein when any of $Z^1$ to $Z^{20}$ is nitrogen, there is no substitution on that nitrogen;

wherein $L^1$ and $G^1$ are bonded together by a C—C bond;

wherein $Ar^1$ is selected from the group consisting of benzene, biphenyl, terphenyl, triphenylene, fluorene, dibenzofuran, dibenzothiophene, dibenzoselenophene, naphthalene, phenanthrene, carbazole, pyridine, pyrimidine, pyrazine, pyridazine, triazine, azatriphenylene, aza-fluorene, aza-dibenzofuran, aza-dibenzothiophene, aza-dibenzoselenophene, aza-carbazole, quinolone, quinazoline, and combinations thereof;

wherein $L^1$ and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, carbazole, pyridine, pyrimidine, pyrazine, pyridazine, triazine, quinolone, phenanthroline, aza-dibenzofuran, aza-dibenzothiophene, aza-dibenzoselenophene, aza-fluorene and aza-triphenylene, aza-carbazole, and combinations thereof; and wherein the compound of Formula I contains at most one non-fused carbazole moiety.

According to another embodiment, a compound having the formula,

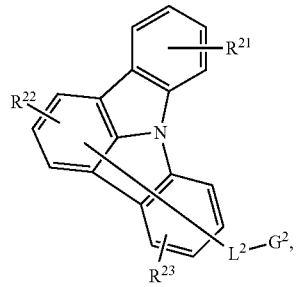

Formula II is disclosed;

wherein $L^2$ is selected from the group consisting of a direct bond, alkyl, alkoxyl, aryl, heteroaryl, and combinations thereof;

wherein $R^{21}$ represents mono, di, tri, or tetra substitution, or no substitution;

wherein $R^{22}$, and $R^{23}$ each independently represent mono, di, or tri substitution, or no substitution;

wherein $R^{21}$ to $R^{23}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;

wherein $G^2$ is selected from the group consisting of:

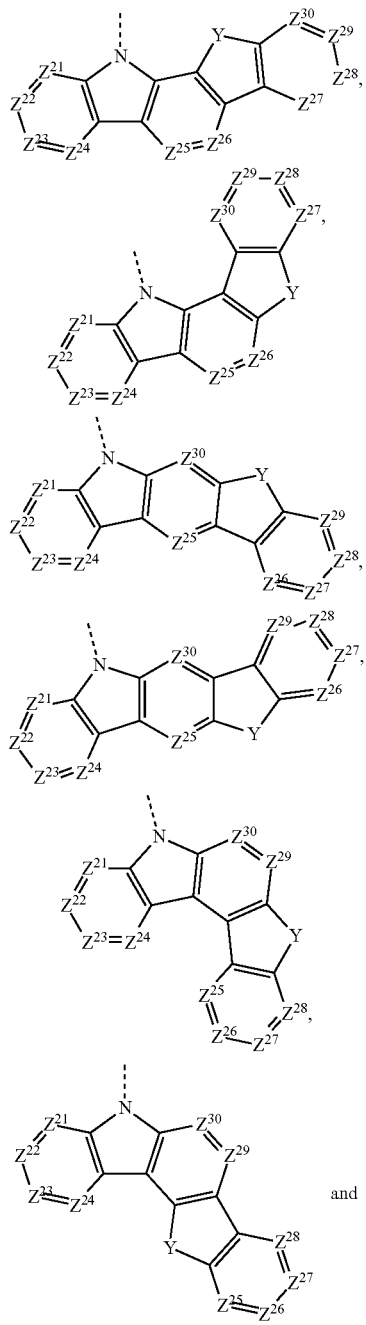

-continued

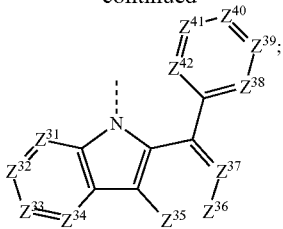

wherein $Z^{21}$ to $Z^{42}$ are each independently selected from the group consisting of C—$R^{20}$ and N;

wherein at least one of $Z^{21}$ to $Z^{42}$ is C—$R^{20}$;

wherein each $R^{20}$ can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any adjacent substituents are optionally joined to form a ring;

wherein Y is selected from the group consisting of: O, S, Se, $BR^{B1}$, $NR^{B2}$, $PR^{B3}$, and $CR^{B4}R^{B5}$;

wherein $R^{B1}$, $R^{B2}$, $R^{B3}$, $R^{B4}$ and $R^{B5}$ are each independently selected from the group consisting of hydrogen, deuterium, alkyl, cycloalkyl, heteroalkyl, arylalkyl, alkoxy, aryloxy, silyl, alkenyl, cycloalkenyl, heteroalkenyl, alkynyl, aryl, heteroaryl, and combinations thereof;

wherein $R^{B4}$ and $R^{B5}$ are optionally jointed to form a ring;

wherein $L^2$ is optionally further substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; and wherein the compound of Formula II contains at most one non-fused carbazole moiety.

According to another aspect of the present disclosure, an organic light emitting device is also provided. The organic light emitting device comprises, an anode, a cathode, and an organic layer that is disposed between the anode and the cathode. The organic layer comprises a compound having a formula selected from the group consisting of:

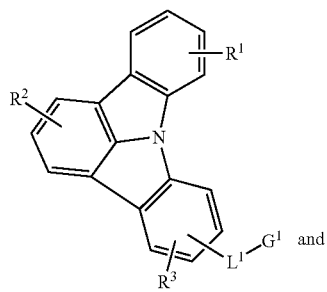

Formula I

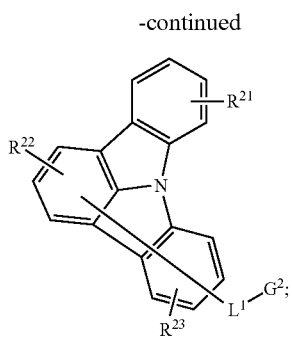

Formula II defined herein.

According to yet another embodiment, a formulation containing the compound of either Formula I or Formula II, including all of their variations, is also provided.

The organic compounds consisting of indolo[3,2,1-jk] carbazole and dibenzofuran, dibenzothiophene, dibenzothienophene, triphenylene, or indolocarbazole disclosed herein are expected to improve OLED performance when incorporated into OLEDs as host material in the emissive layer.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
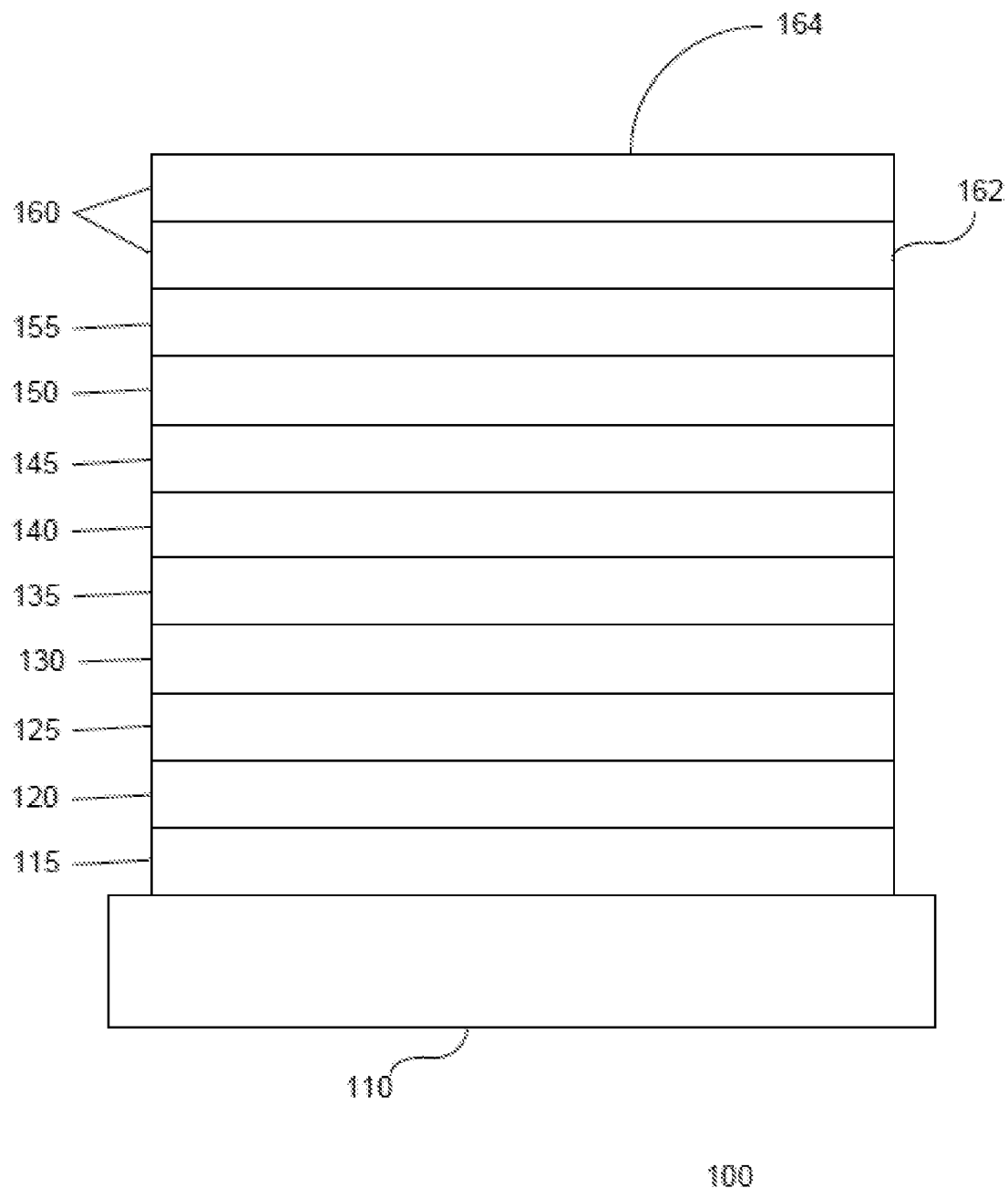
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
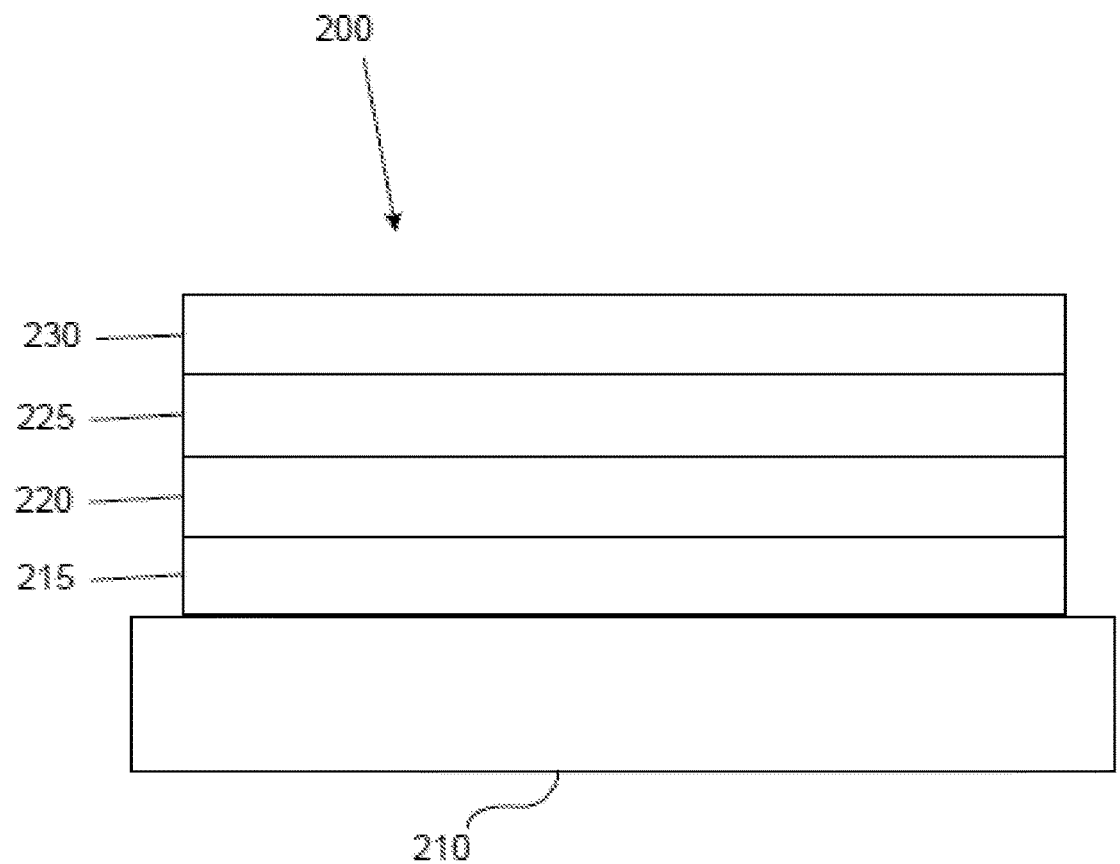
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Disclosed herein is a class of novel compounds containing indolo[3,2,1-jk]carbazole connected to dibenzofuran, dibenzothiophene or dibenzothienophene. Indolocarbazole and dibenzothiophene are excellent charge-transport building blocks due to their rigid chemical structures conducive to molecular assembly. The module containing dibenzothiophene and indolocarbazole is further substituted with aromatic or heteroaromatic building blocks to modify energy levels and charge-transport properties. The compounds of this novel combination are expected to improve OLED device performance when incorporated into the emissive layer as a host material.

The following novel compound that is useful as host material in the emissive layer of organic light emitting devices is disclosed. According to an embodiment, the compound has a structure according to formula:

Formula I

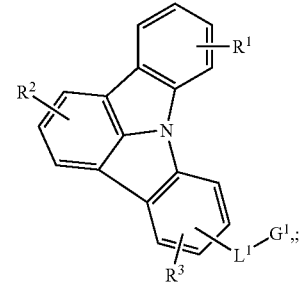

wherein $L^1$ is selected from the group consisting of a direct bond, phenyl, biphenyl, terphenyl, fluorene, carbazole, pyridine, pyrimidine, pyrazine, pyridazine, triazine, naphthalene, anthracene, and combinations thereof;

wherein $G^1$ is selected from the group consisting of:

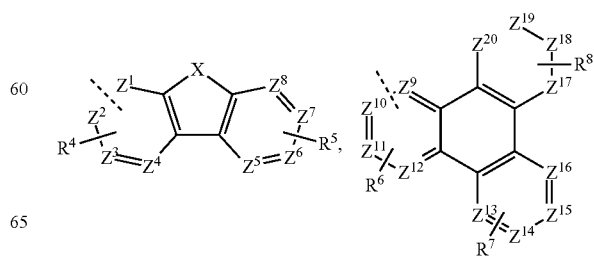

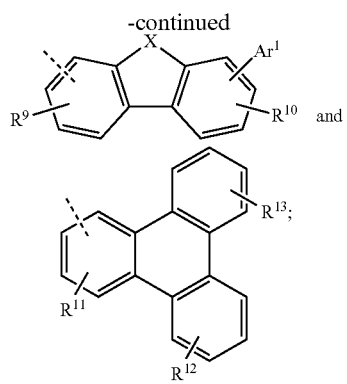
and

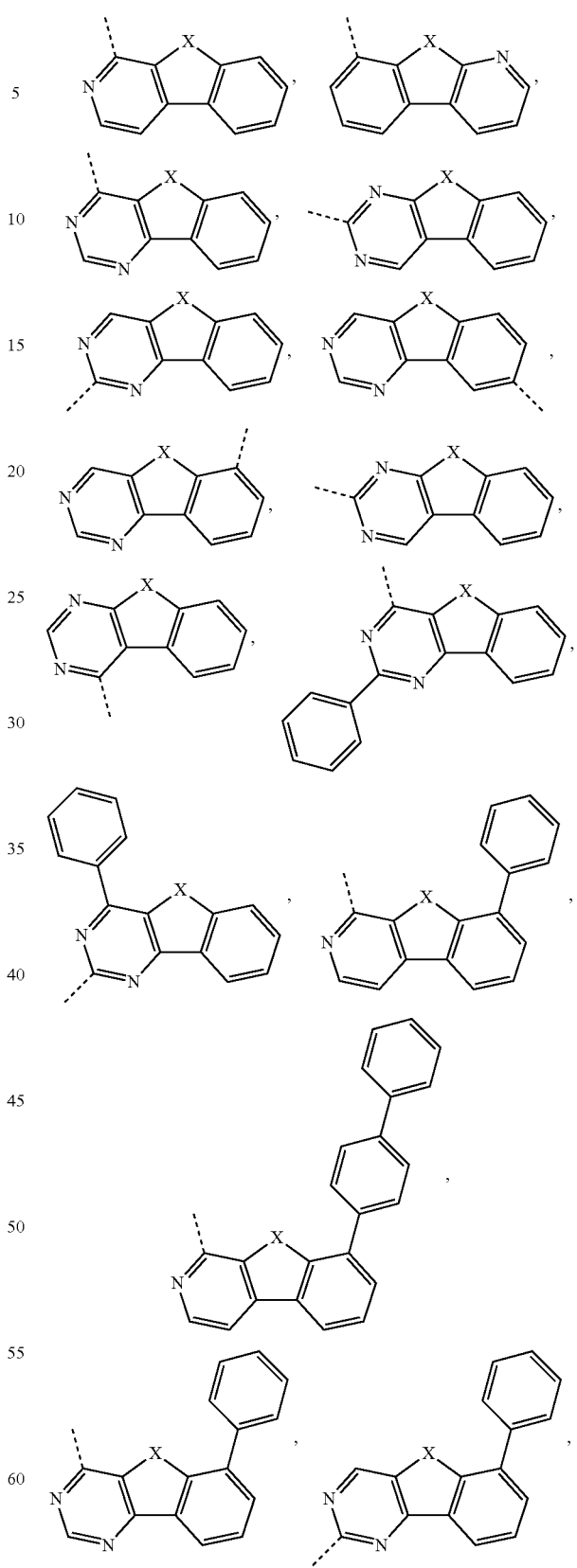

wherein X is selected from the group consisting of oxygen, sulfur, and selenium;

wherein $R^1$, $R^5$, $R^7$, $R^8$, $R^{12}$, and $R^{13}$ each independently represent mono, di, tri, or tetra substitution, or no substitution;

wherein $R^2$, $R^3$, $R^4$, $R^5$, $R^6$, $R^9$, $R^{10}$, and $R^{11}$ each independently represent mono, di, or tri substitution, or no substitution;

wherein $R^1$ to $R^{13}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;

wherein $Z^1$ to $Z^{20}$ are each independently selected from the group consisting of carbon and nitrogen;

wherein at least one of $Z^1$, $Z^2$, $Z^3$, $Z^4$, $Z^5$, $Z^6$, $Z^7$, and $Z^8$ is nitrogen; and at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$, and $Z^{20}$ is nitrogen;

wherein when any of $Z^1$ to $Z^{20}$ is nitrogen, there is no substitution on that nitrogen;

wherein $L^1$ and $G^1$ are bonded together by a C—C bond;

wherein $Ar^1$ is selected from the group consisting of benzene, biphenyl, terphenyl, triphenylene, fluorene, dibenzofuran, dibenzothiophene, dibenzoselenophene, naphthalene, phenanthrene, carbazole, pyridine, pyrimidine, pyrazine, pyridazine, triazine, azatriphenylene, aza-fluorene, aza-dibenzofuran, aza-dibenzothiophene, aza-dibenzoselenophene, aza-carbazole, quinolone, quinazoline, and combinations thereof;

wherein $L^1$ and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, carbazole, pyridine, pyrimidine, pyrazine, pyridazine, triazine, quinolone, phenanthroline, aza-dibenzofuran, aza-dibenzothiophene, aza-dibenzoselenophene, aza-fluorene and aza-triphenylene, aza-carbazole, and combinations thereof; and wherein the compound of Formula I contains at most one non-fused carbazole moiety.

As used herein, "non-fused carbazole moiety" means a carbazole moiety where the phenyl group at the 9 position is not directly connected to 1 position on the carbazole.

In the compound of Formula I, $G^1$ can be selected from the group consisting of:

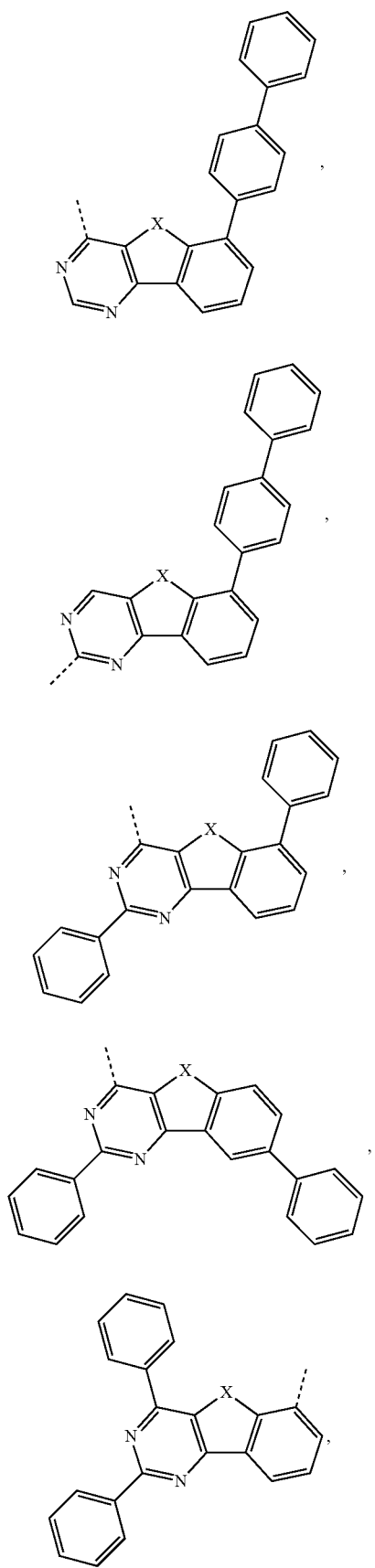
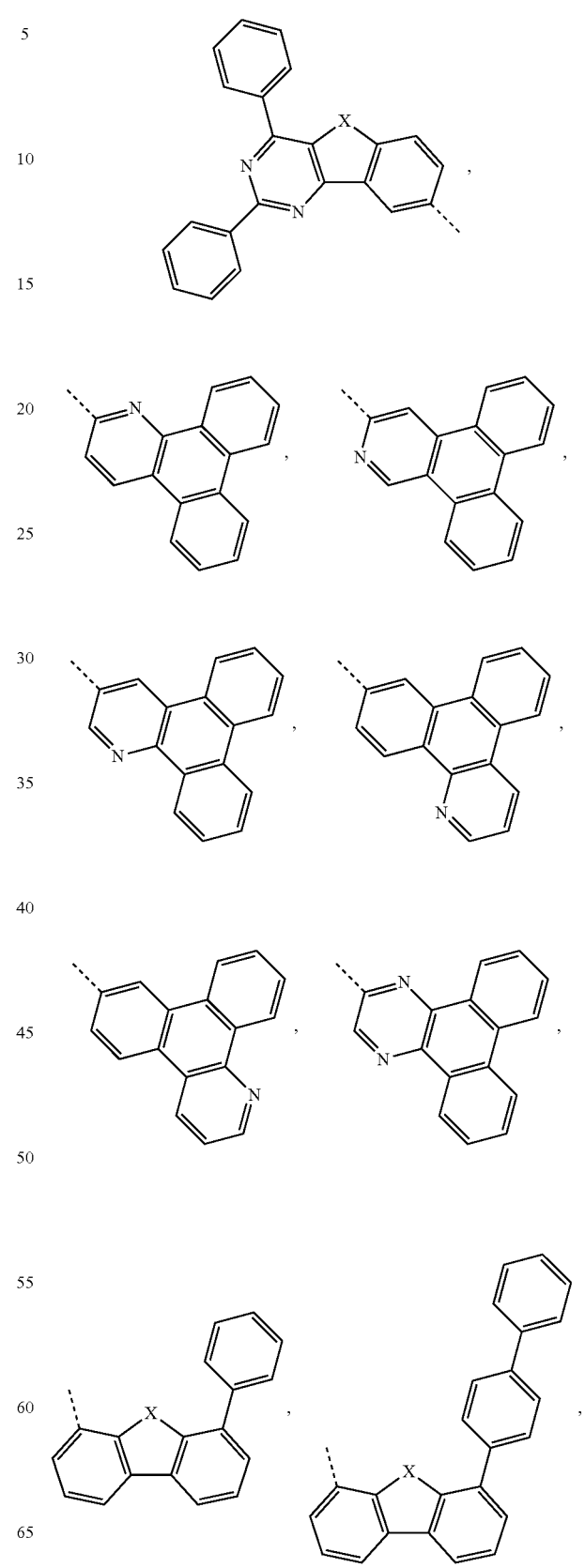

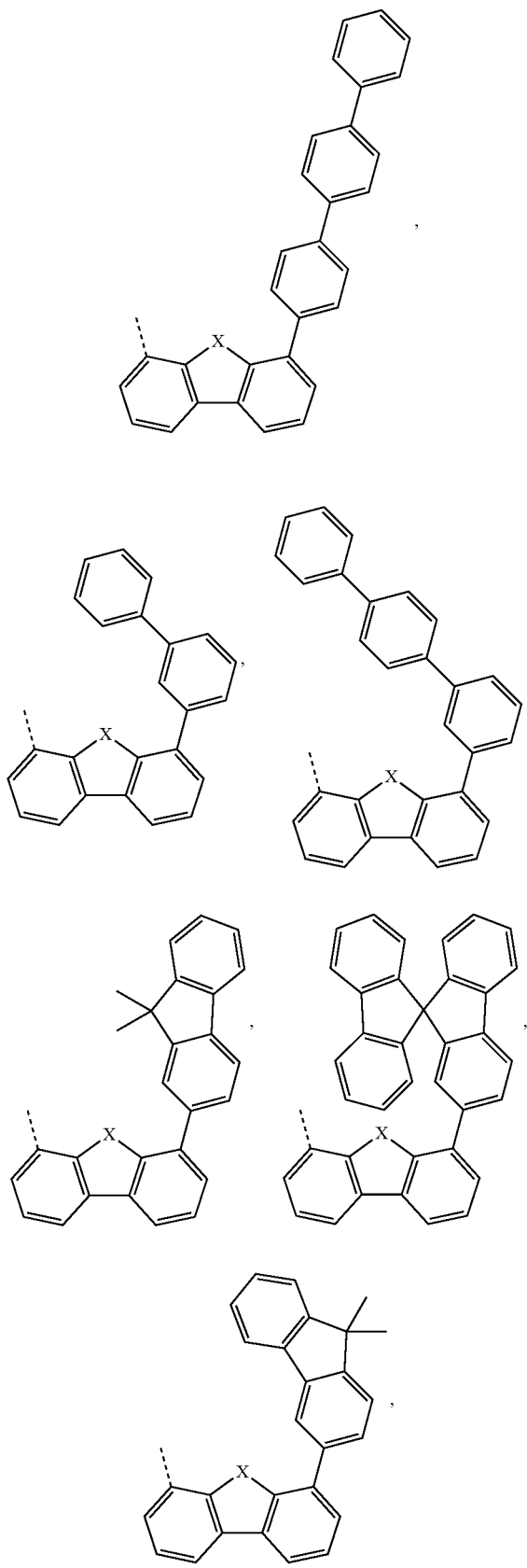
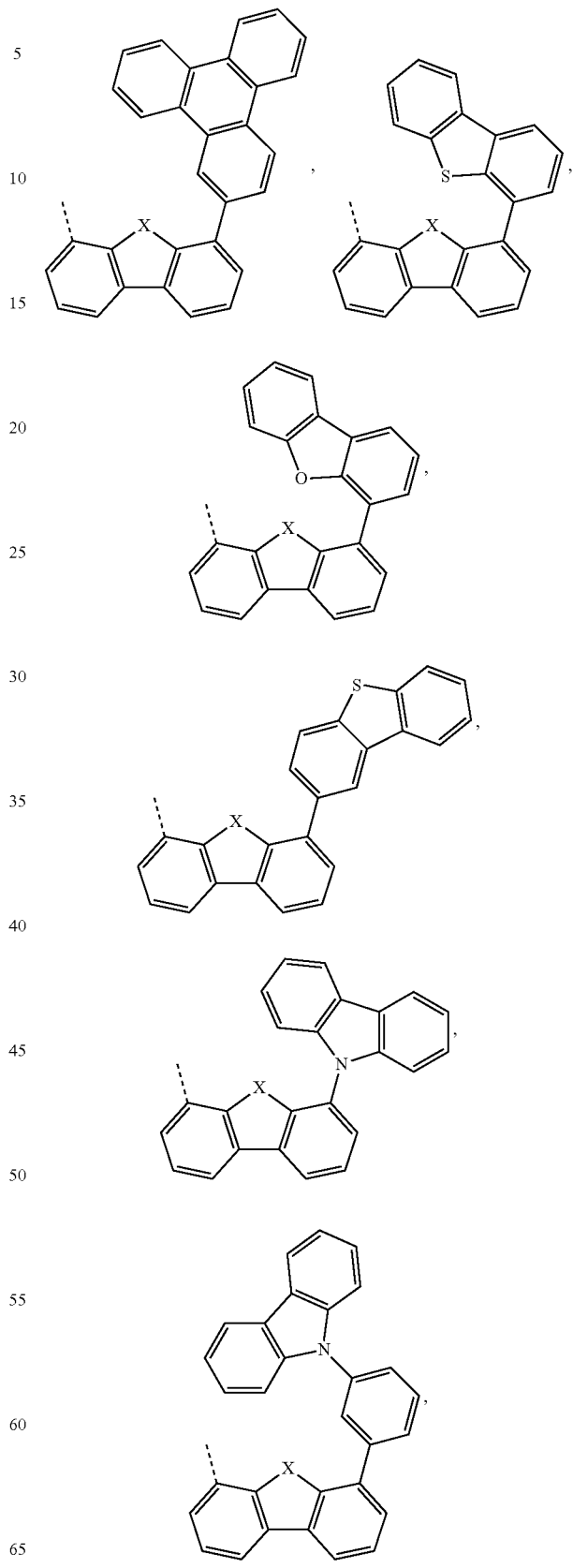

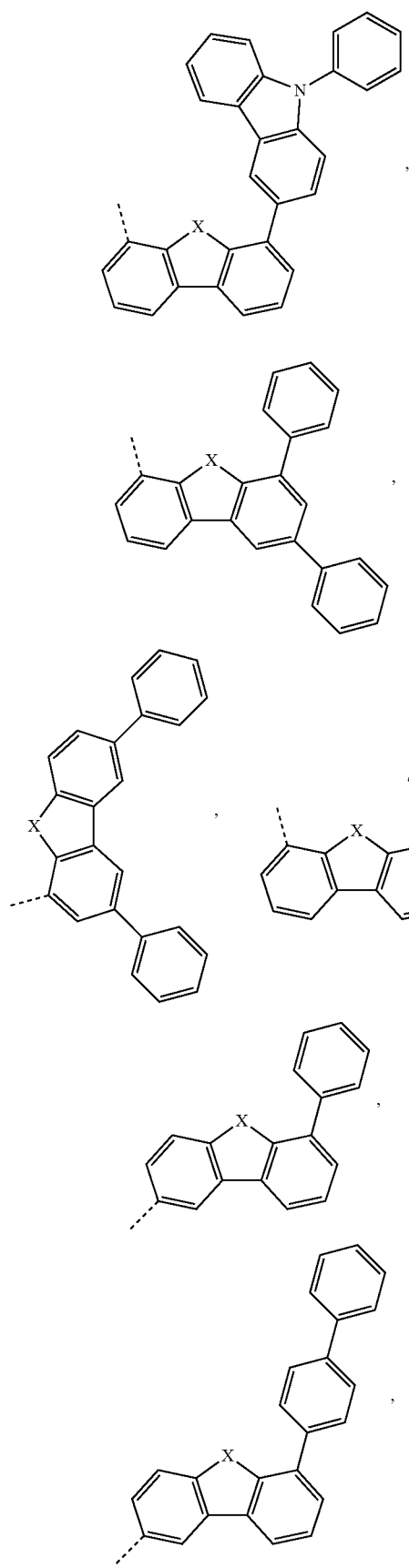
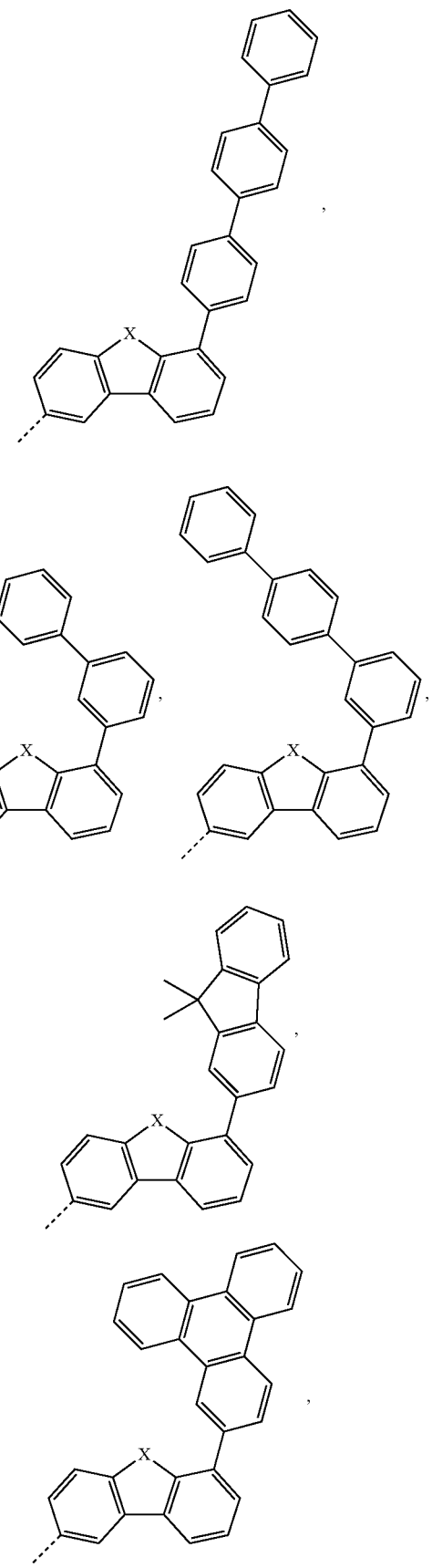

In some embodiments of the compound of Formula I, the compound is selected from the group consisting of:

In the compound of Formula I, L¹ can be selected from the group consisting of: a direct bond, -continued

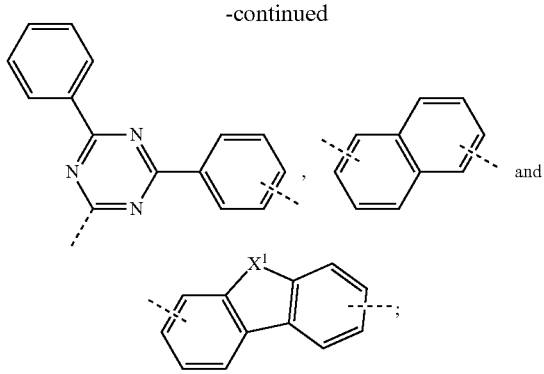

wherein $X^1$ is selected from a group consisting of O, S, Se, $CR^{L1}R^{L2}$, and $NR^{L3}$; and wherein $R^{L1}$, $R^{L2}$, and $R^{L3}$ are each independently selected from the group consisting of hydrogen, deuterium, alkyl, aryl, and combinations thereof.

In some embodiments, the compound of Formula I can be selected from the group consisting of:

Compounds A1, A2, and A3
each represented by the formula

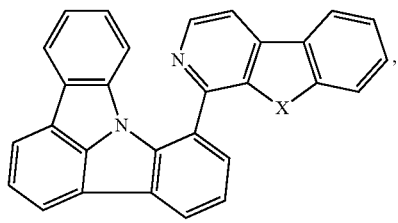

wherein in Compound A1, X = O,
in Compound A2, X = S, and
in Compound A3, X = Se Compounds A4, A5, and A6
each represented by the formula

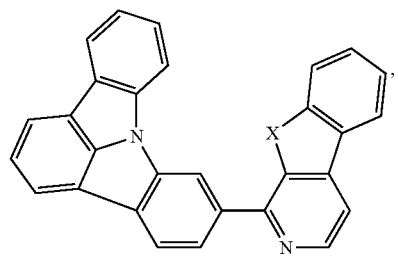

wherein in Compound A4, X = O,
in Compound A5, X = S, and
in Compound A6, X = Se Compounds A7, A8, and A9
each represented by the formula

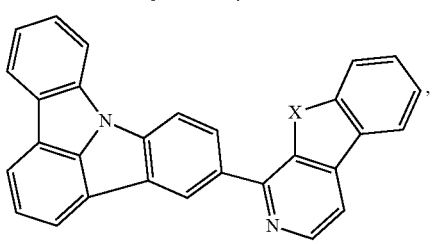

wherein in Compound A7, X = O,
in Compound A8, X = S, and
in Compound A9, X = Se -continued Compounds A10, A11, and A12
each represented by the formula

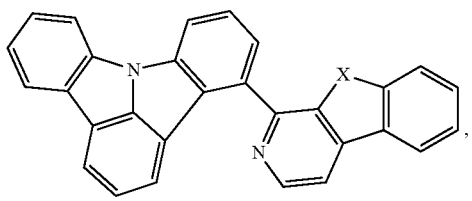

wherein in Compound A10, X = O,
in Compound A11, X = S, and
in Compound A12, X = Se Compounds A13, A14, and A15
each represented by the formula

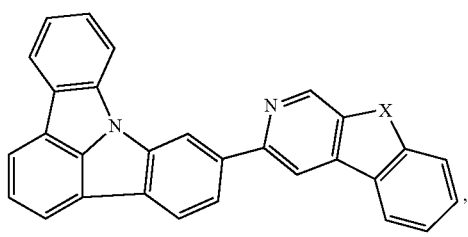

wherein in Compound A13, X = O,
in Compound A14, X = S, and
in Compound A15, X = Se Compounds A16, A17, and A18
each represented by the formula

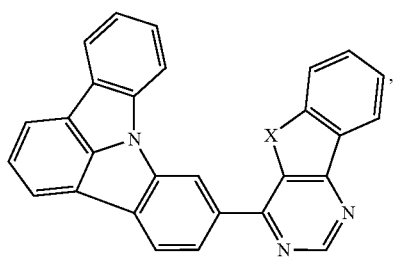

wherein in Compound A16, X = O,
in Compound A17, X = S, and
in Compound A18, X = Se Compounds A19, A20, and A21
each represented by the formula

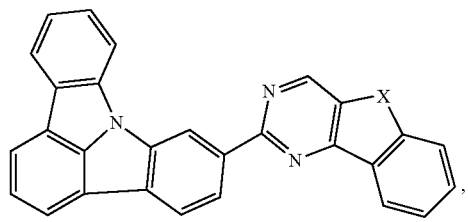

wherein in Compound A19, X = O,
in Compound A20, X = S, and
in Compound A21, X = Se -continued Compounds A22, A23, and A24 each represented by the formula

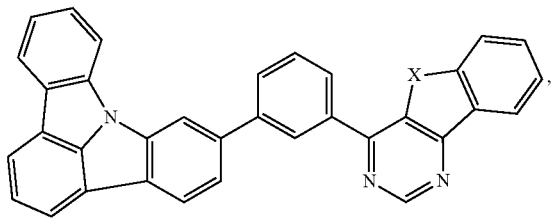

wherein in Compound A22, X = O,
in Compound A23, X = S, and
in Compound A24, X = Se Compounds A25, A26, and A27 each represented by the formula

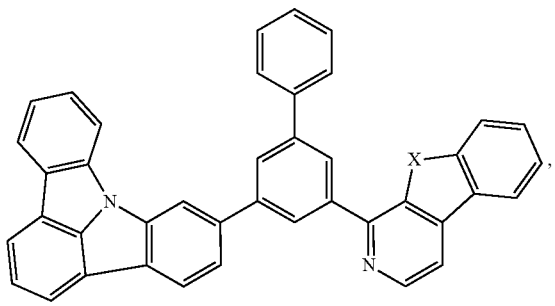

wherein in Compound A25, X = O,
in Compound A26, X = S, and
in Compound A27, X = Se Compounds A28, A29, and A30 each represented by the formula

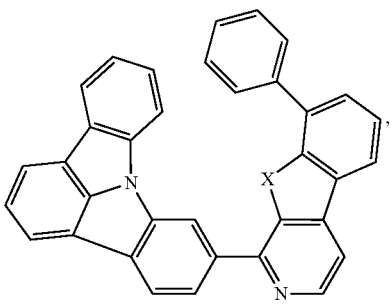

wherein in Compound A28, X = O,
in Compound A29, X = S, and
in Compound A30, X = Se Compounds A31, A32, and A33 each represented by the formula

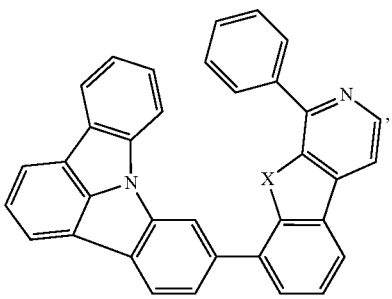

wherein in Compound A31, X = O,
in Compound A32, X = S, and
in Compound A33, X = Se Compounds A34, A35, and A36 each represented by the formula

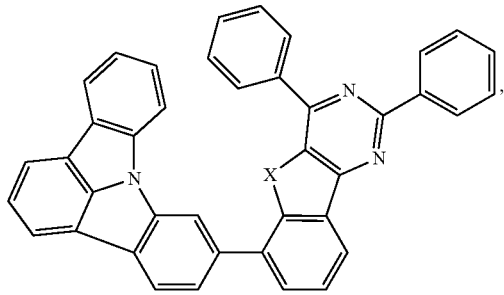

wherein in Compound A34, X = O,
in Compound A35, X = S, and
in Compound A36, X = Se Compounds A37, A38, and A39 each represented by the formula

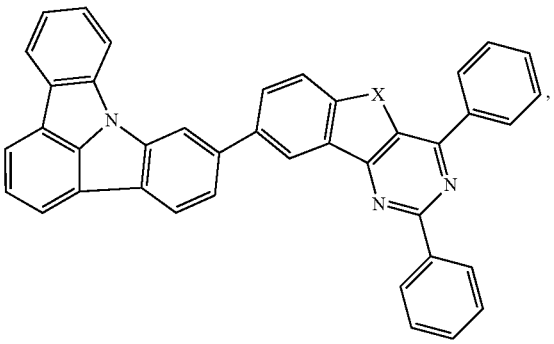

wherein in Compound A37, X = O,
in Compound A38, X = S, and
in Compound A39, X = Se Compounds A40, A41, and A42 each represented by the formula

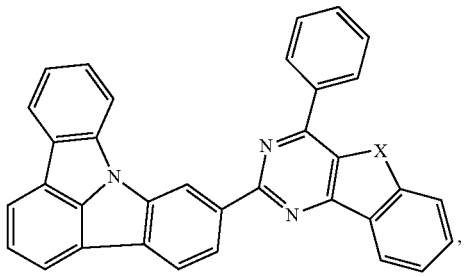

wherein in Compound A40, X = O,
in Compound A41, X = S, and
in Compound A42, X = Se Compounds A43, A44, and A45 each represented by the formula

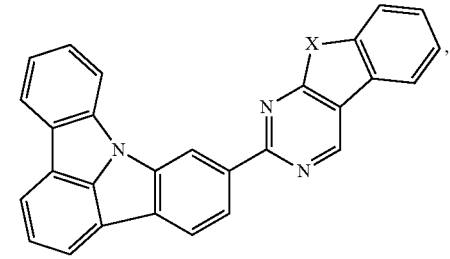

wherein in Compound A43, X = O,
in Compound A44, X = S, and
in Compound A45, X = Se -continued
Compounds A46, A47, and A48 each represented by the formula
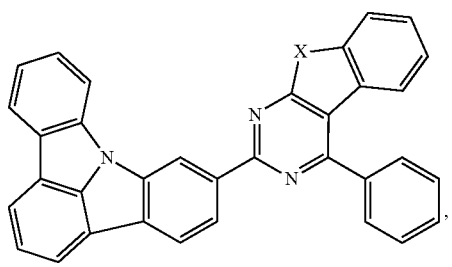
wherein in Compound A46, X = O, in Compound A47, X = S, and in Compound A48, X = Se
Compound B1
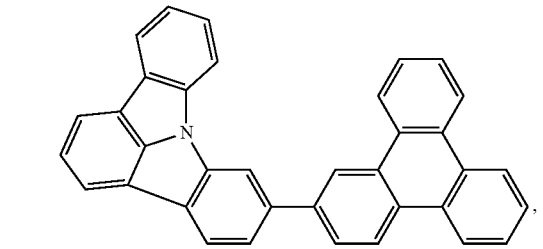
Compound B2
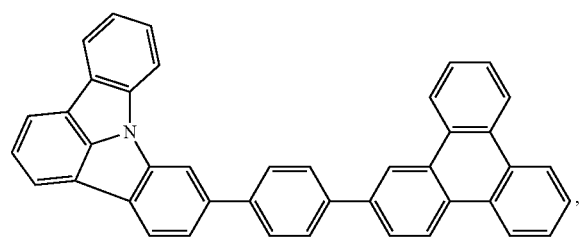
Compound B3
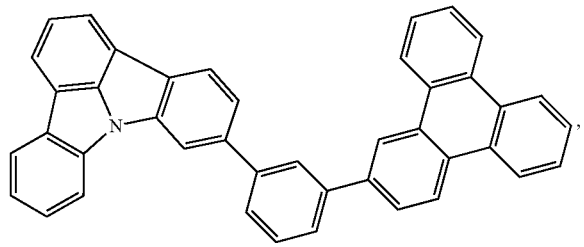
Compound B4
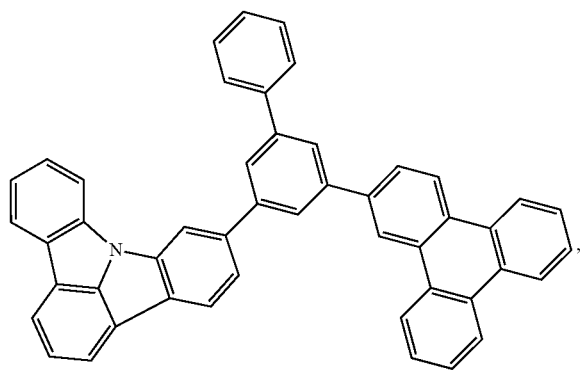
-continued
Compound B5
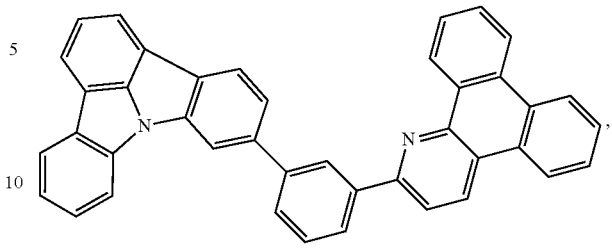
Compound B6
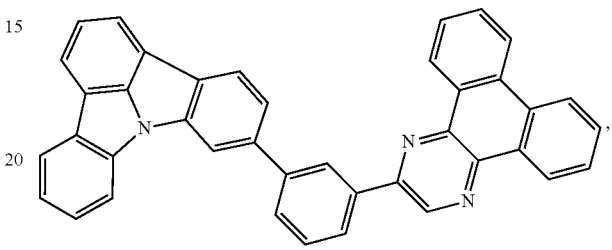
Compound B7
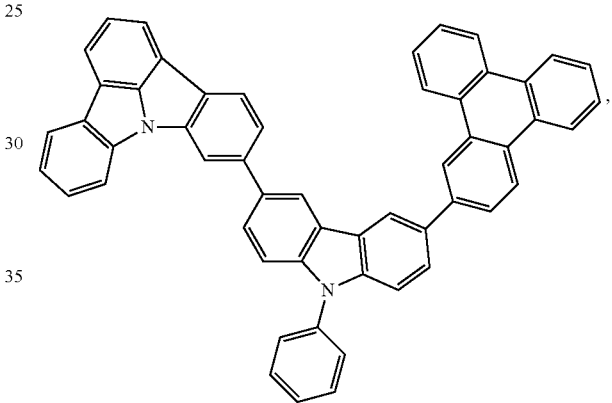
Compound B8
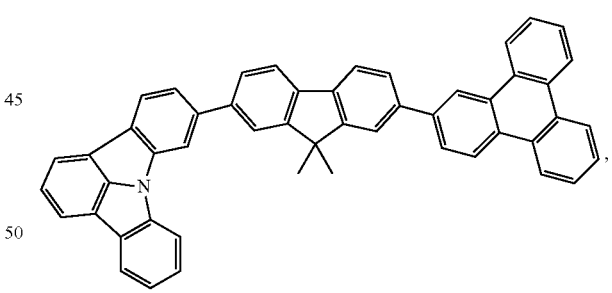
Compound B9
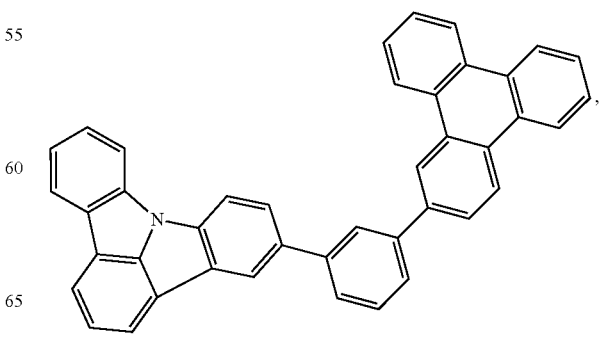

Compounds C1, C2, and C3 each represented by the formula

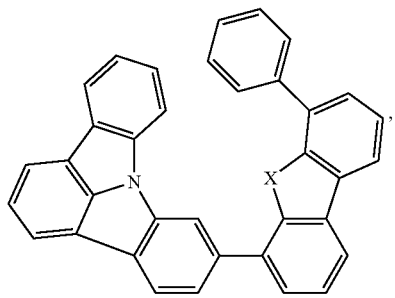

wherein in Compound C1, X = O,
in Compound C2, X = S, and
in Compound C3, X = Se Compounds C4, C5, and C6 each represented by the formula

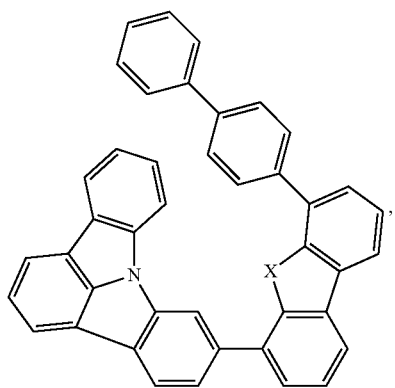

wherein in Compound C4, X = O,
in Compound C5, X = S, and
in Compound C6, X = Se Compounds C7, C8, and C9 each represented by the formula

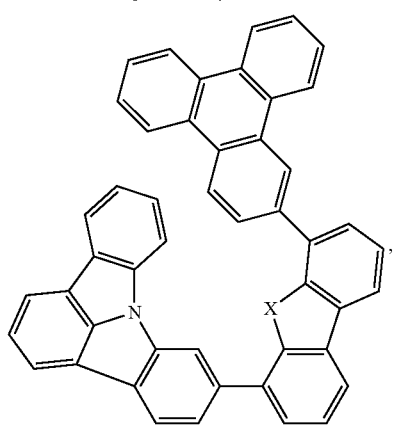

wherein in Compound C7, X = O,
in Compound C8, X = S, and
in Compound C9, X = Se Compounds C10, C11, and C12 each represented by the formula

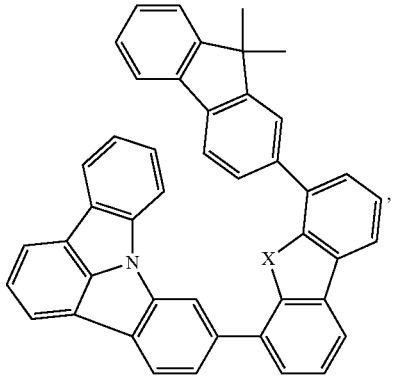

wherein in Compound C10, X = O,
in Compound C11, X = S, and
in Compound C12, X = Se Compounds C13, C14, and C15 each represented by the formula

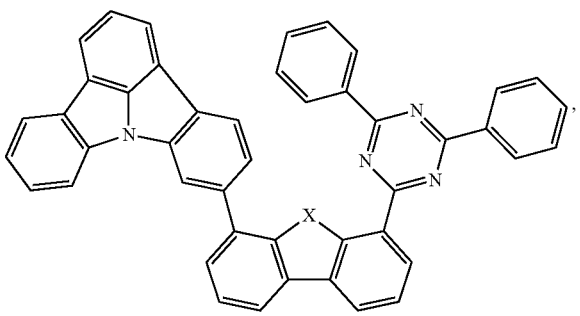

wherein in Compound C13, X = O,
in Compound C14, X = S, and
in Compound C15, X = Se Compounds C16, C17, and C18 each represented by the formula

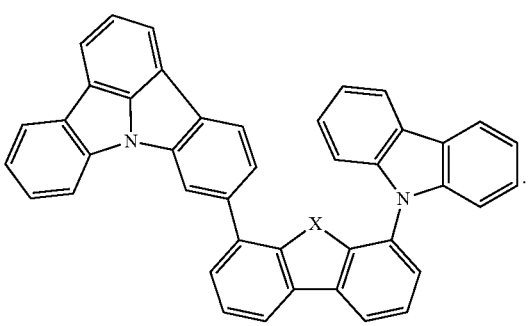

wherein in Compound C16, X = O,
in Compound C17, X = S, and
in Compound C18, X = Se Compounds C19, C20, and C21 each represented by the formula

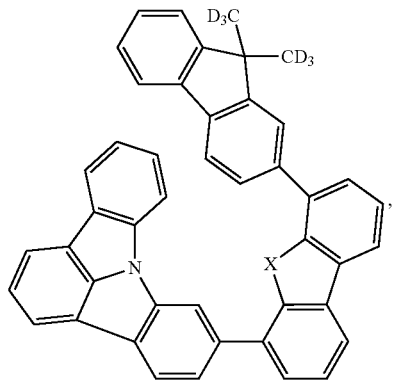

wherein in Compound C19, X = O,
in Compound C20, X = S, and
in Compound C21, X = Se Compounds C22, C23, and C24 each represented by the formula

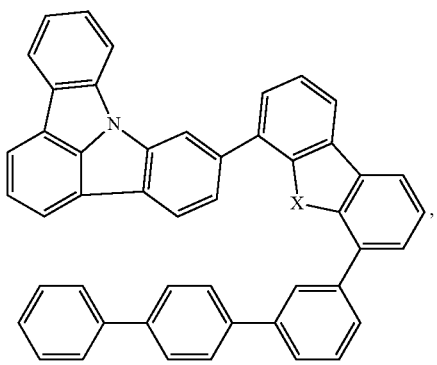

wherein in Compound C22, X = O,
in Compound C23, X = S, and
in Compound C24, X = Se Compounds C25, C26, and C27 each represented by the formula

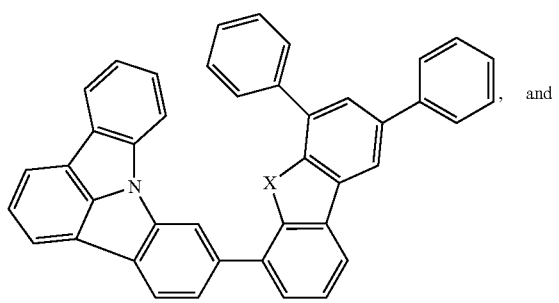, and wherein in Compound C25, X = O,
in Compound C26, X = S, and
in Compound C27, X = Se Compounds C28, C29, and C30 each represented by the formula

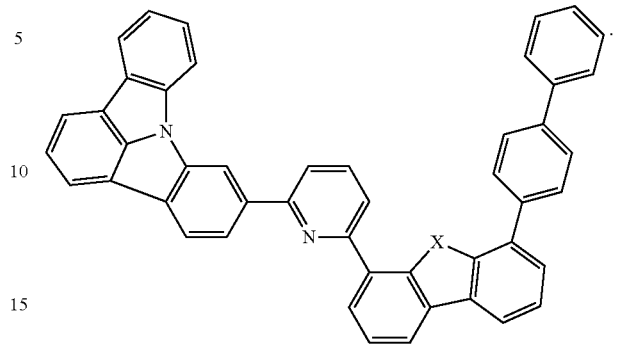

wherein in Compound C28, X = O,
in Compound C29, X = S, and
in Compound C30, X = Se According to another embodiment, a compound having the formula,

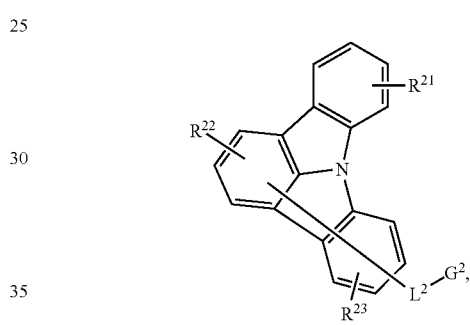

Formula II is disclosed;

wherein $L^2$ is selected from the group consisting of a direct bond, alkyl, alkoxyl, aryl, heteroaryl, and combinations thereof;

wherein $R^{21}$ represents mono, di, tri, or tetra substitution, or no substitution;

wherein $R^{22}$, and $R^{23}$ each independently represent mono, di, or tri substitution, or no substitution;

wherein $R^{21}$, $R^{22}$, and $R^{23}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;

wherein $G^2$ is selected from the group consisting of:

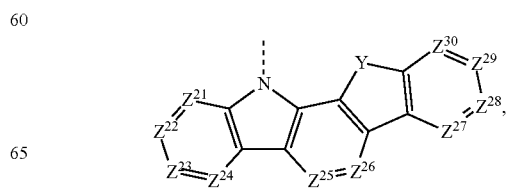

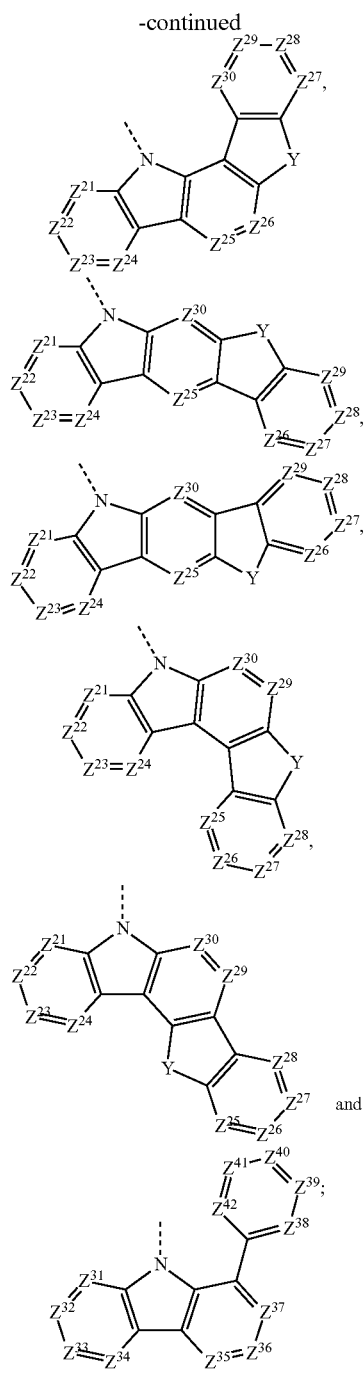

wherein $Z^{21}$ to $Z^{42}$ are each independently selected from the group consisting of C—$R^{20}$ and N;

wherein at least one of $Z^{21}$ to $Z^{42}$ is C—$R^{20}$;

wherein each $R^{20}$ can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any adjacent substituents are optionally joined to form a ring;

wherein Y is selected from the group consisting of: O, S, Se, $BR^{B1}$, $NR^{B2}$, $PR^{B3}$, and $CR^{B4}R^{B5}$;

wherein $R^{B1}$, $R^{B2}$, $R^{B3}$, $R^{B4}$ and $R^{B5}$ are each independently selected from the group consisting of hydrogen, deuterium, alkyl, cycloalkyl, heteroalkyl, arylalkyl, alkoxy, aryloxy, silyl, alkenyl, cycloalkenyl, heteroalkenyl, alkynyl, aryl, heteroaryl, and combinations thereof;

wherein $R^{B4}$ and $R^{B5}$ are optionally jointed to form a ring;

wherein $L^2$ is optionally further substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; and wherein the compound of Formula II contains at most one non-fused carbazole moiety.

In some embodiments, the compound of Formula II can be selected from the group consisting of:

Compound D1

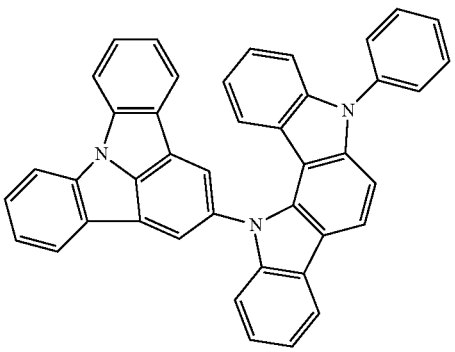

Compound D2

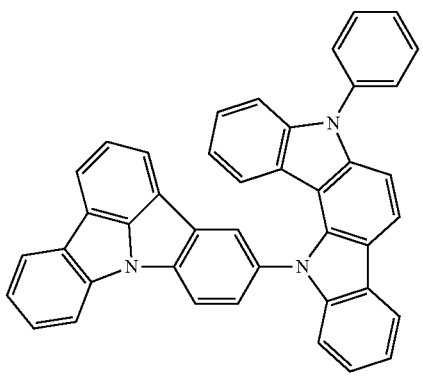

Compound D3

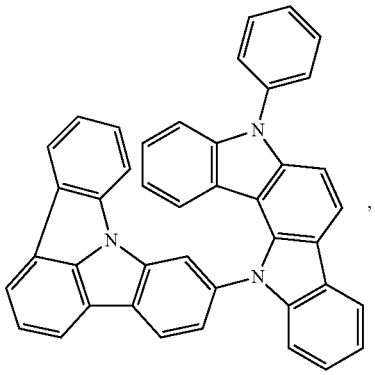

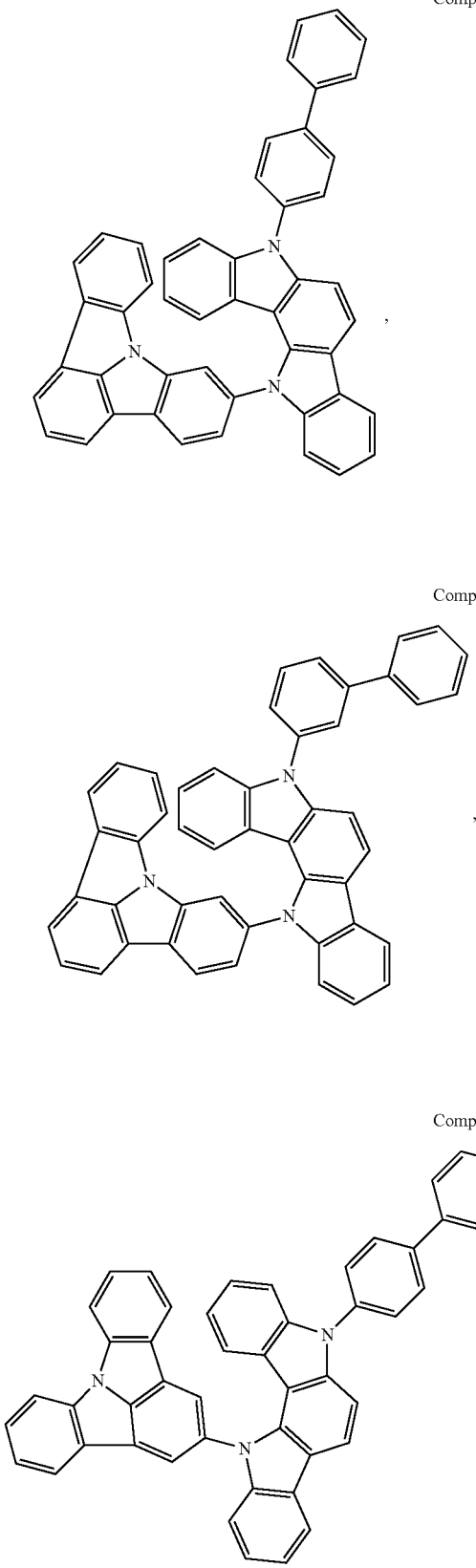
Compound D4
Compound D5
Compound D6
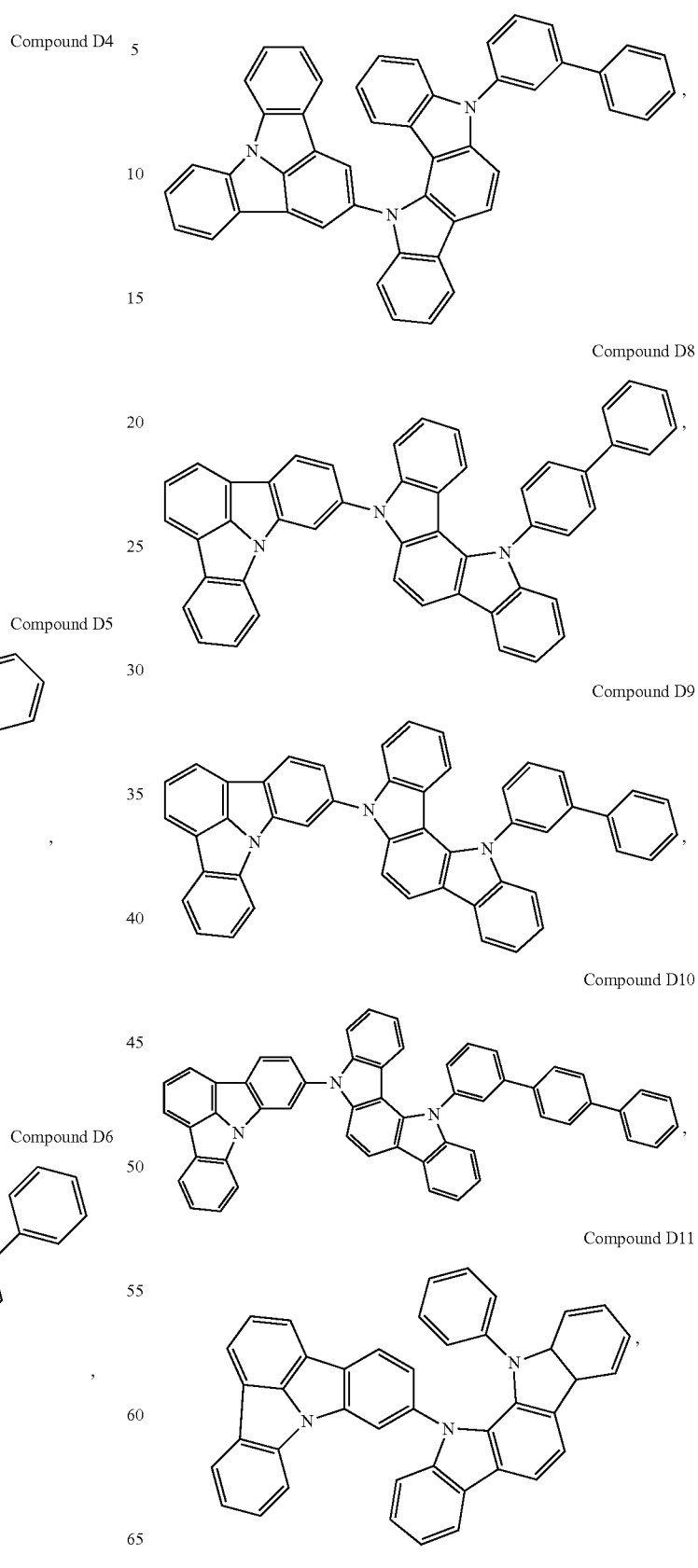
Compound D7
Compound D8
Compound D9
Compound D10
Compound D11

Compound D12
Compound D13
Compound D14
Compound D15
Compound D16
Compound D17
Compound D18
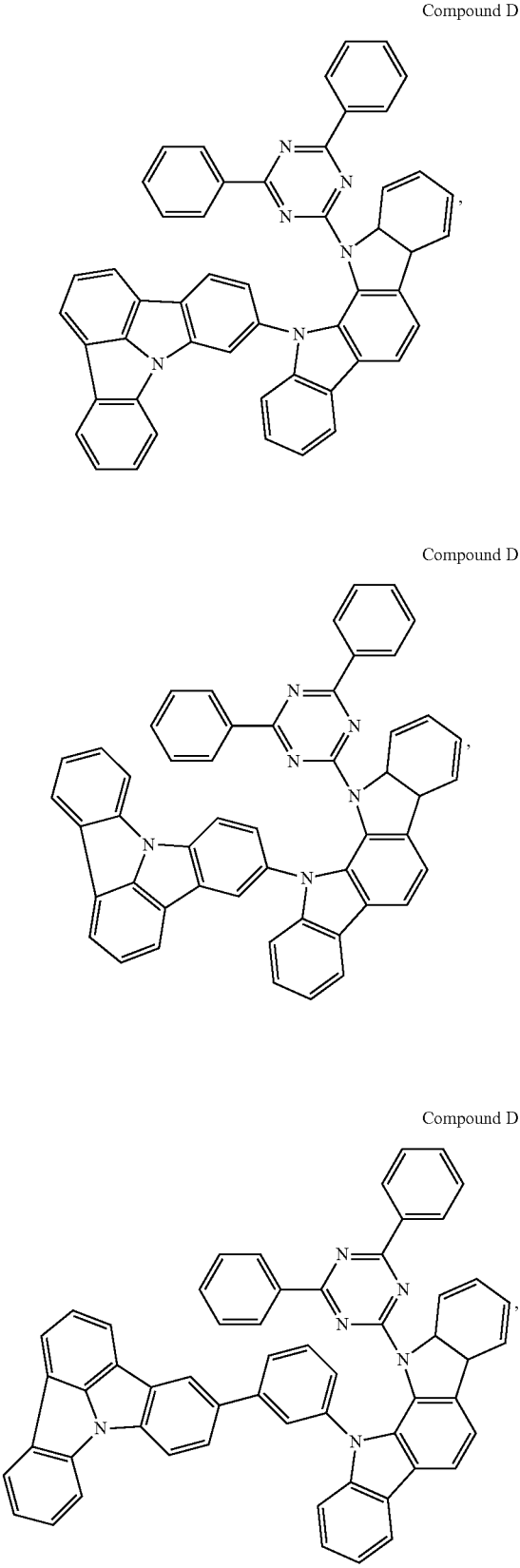
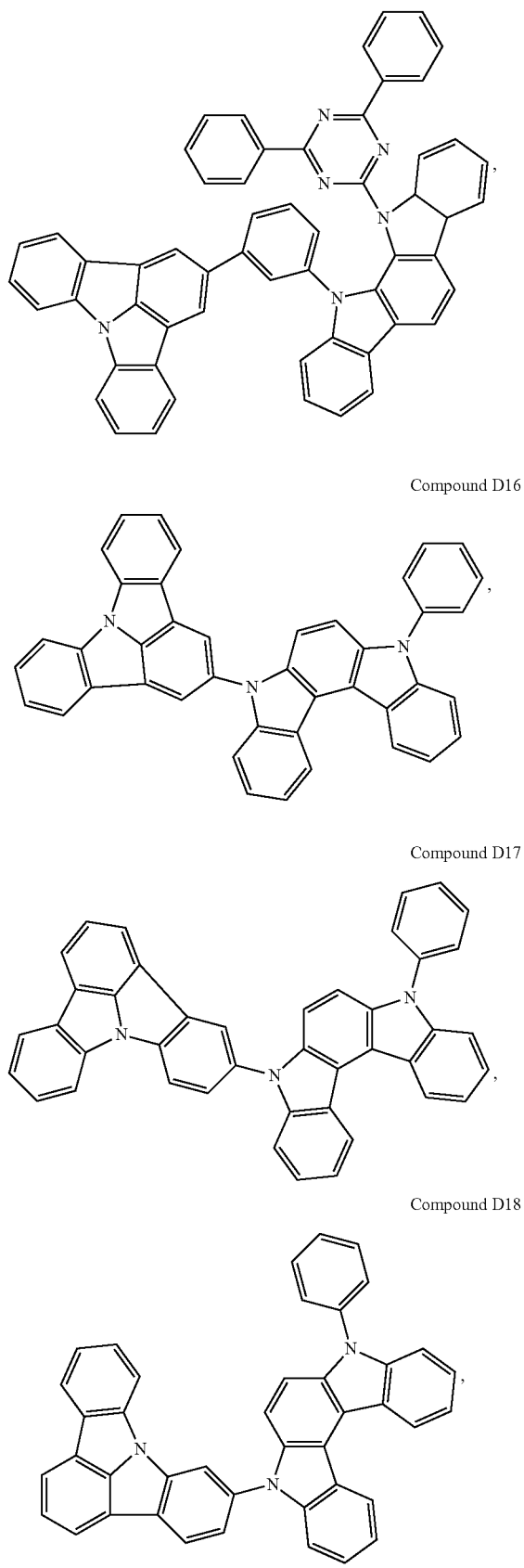

Compound D19
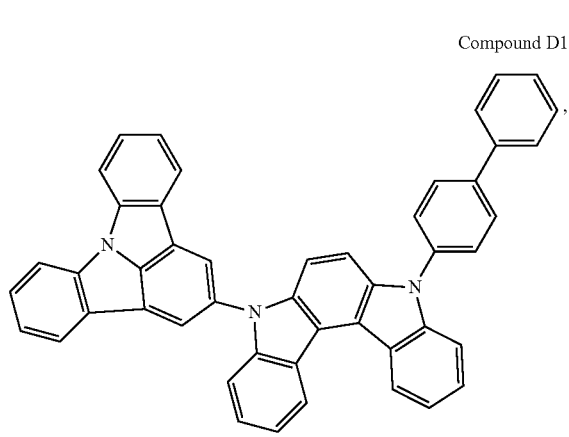
Compound D22
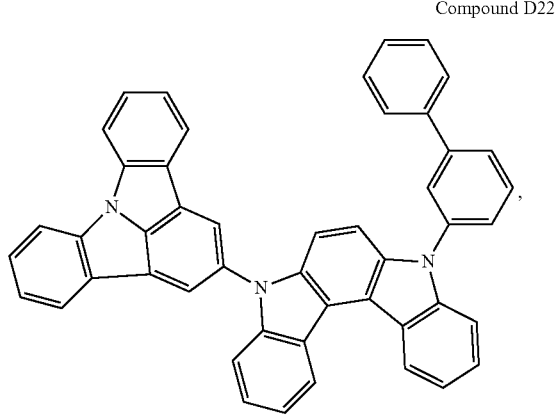
Compound D20
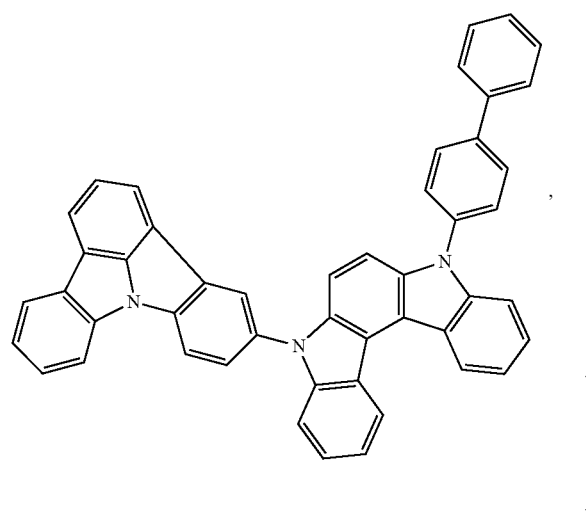
Compound D23
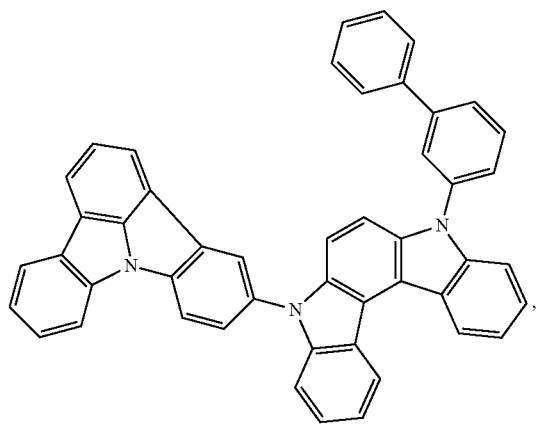
Compound D21
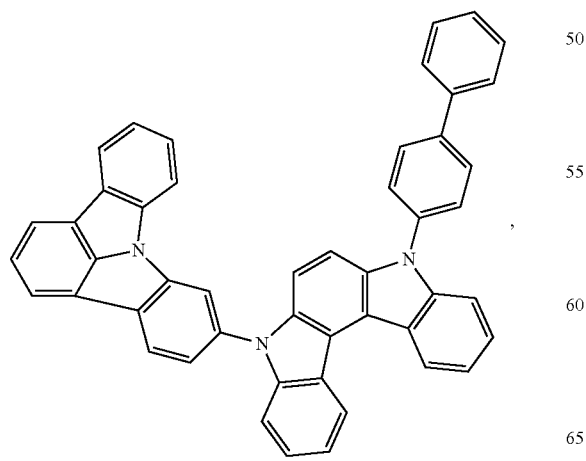
Compound D24
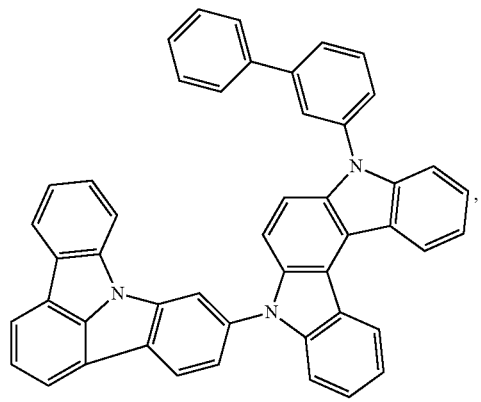

Compound D25
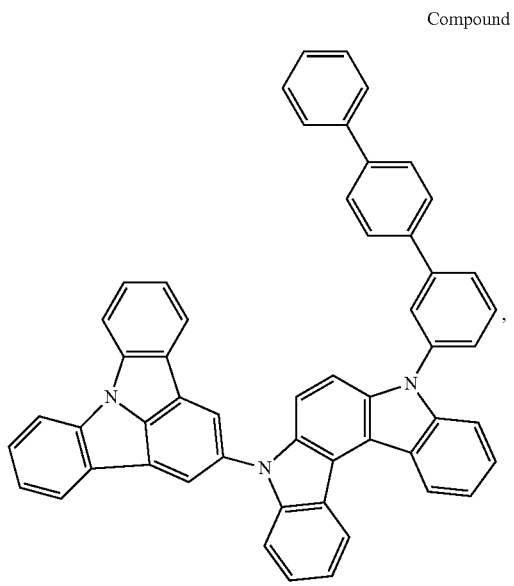
Compound D26
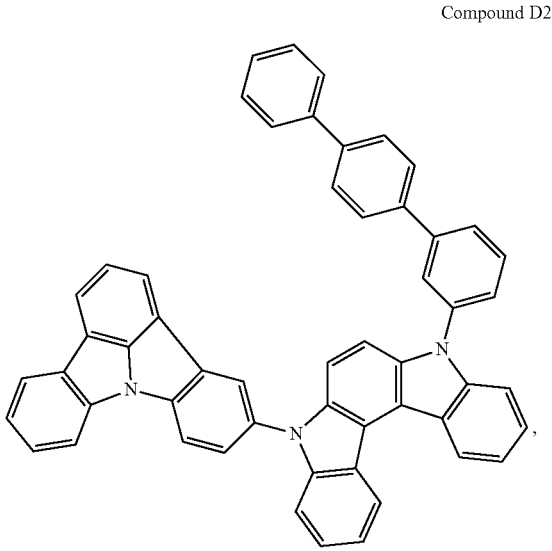
Compound D27
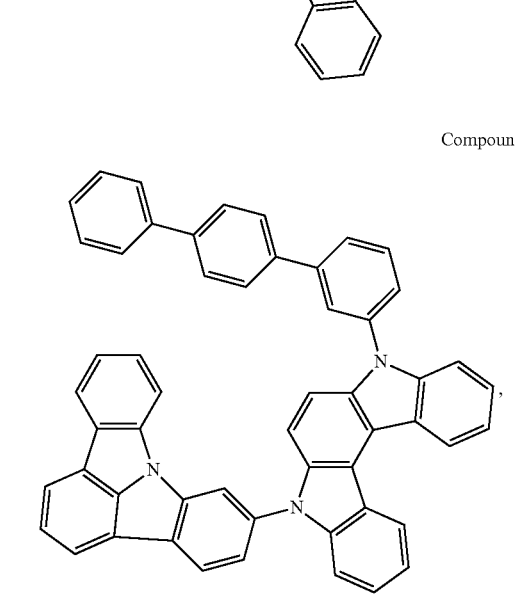
Compound D28
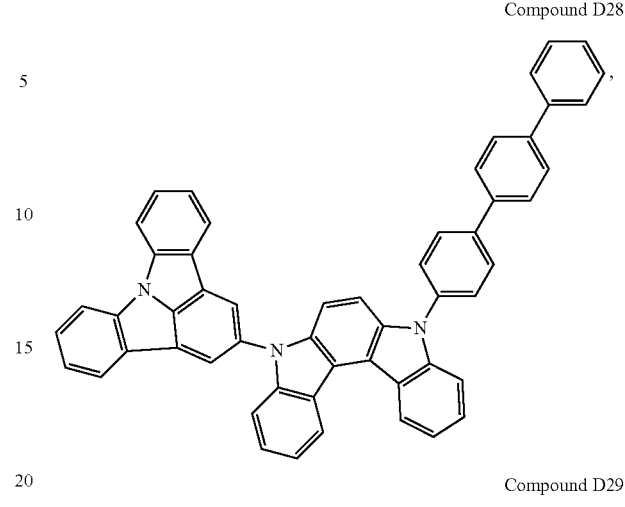
Compound D29
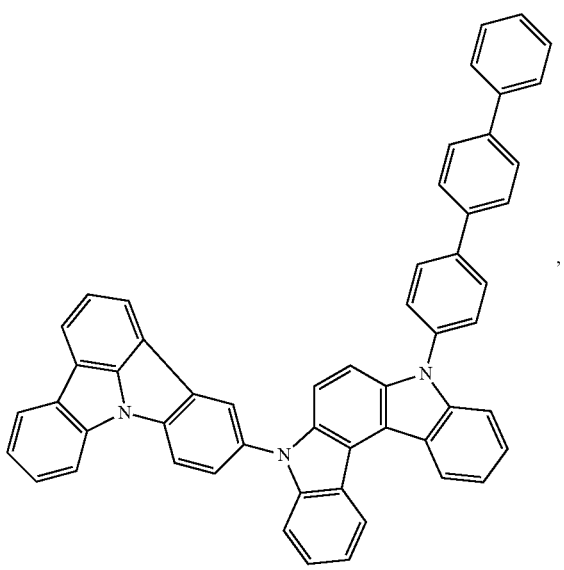
Compound D30
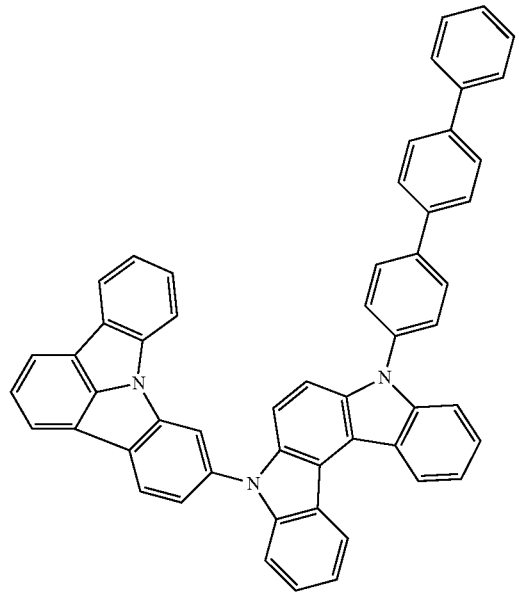

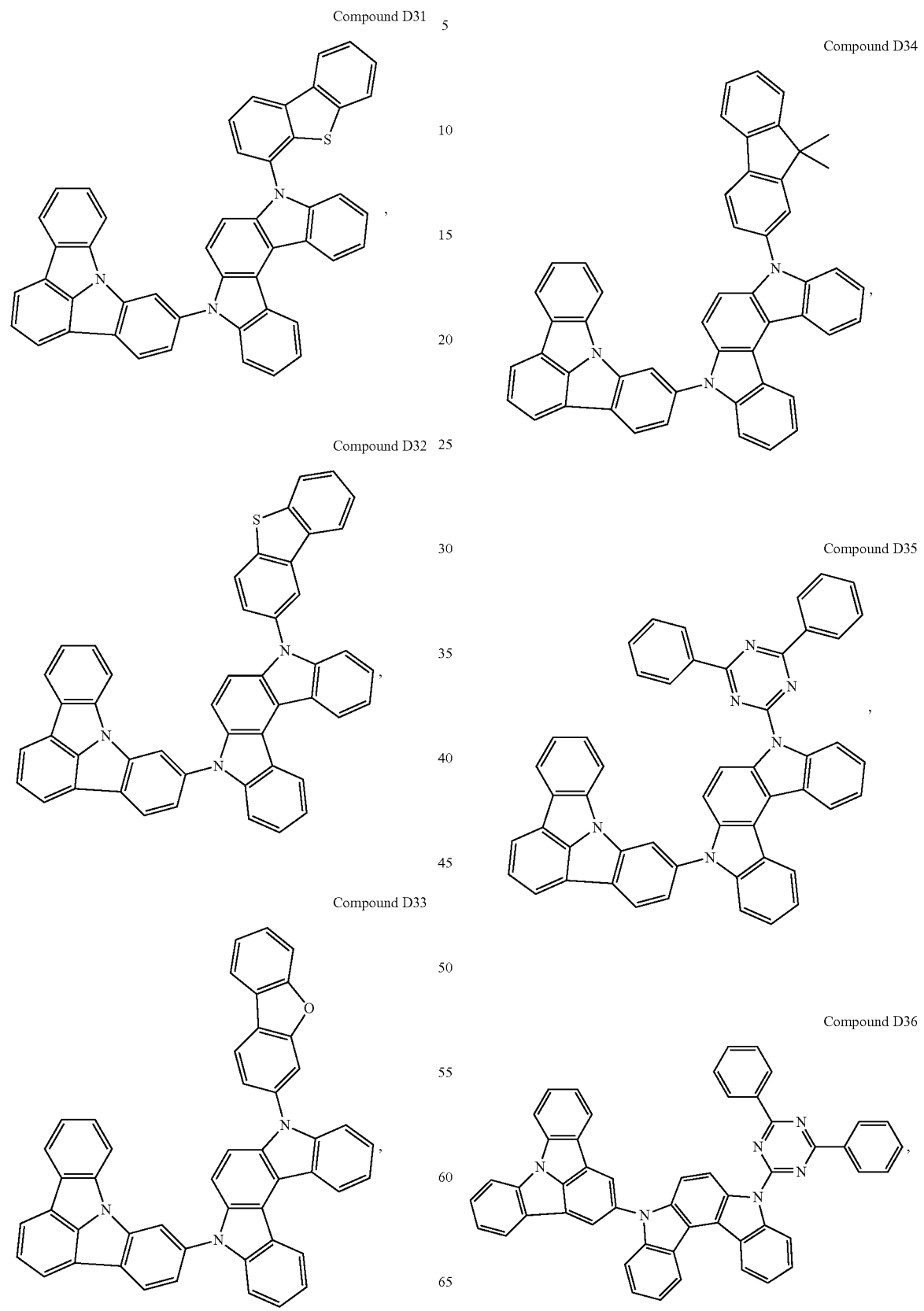

Compound D37
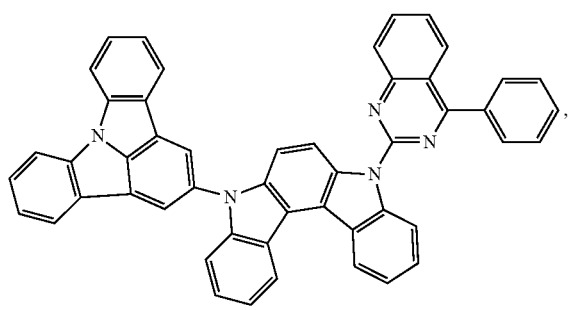
Compound D38
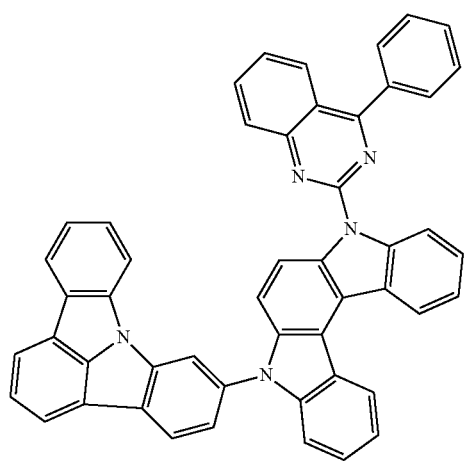
Compound D39
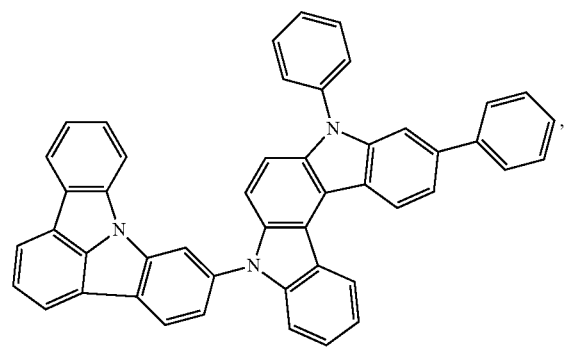
Compound D40
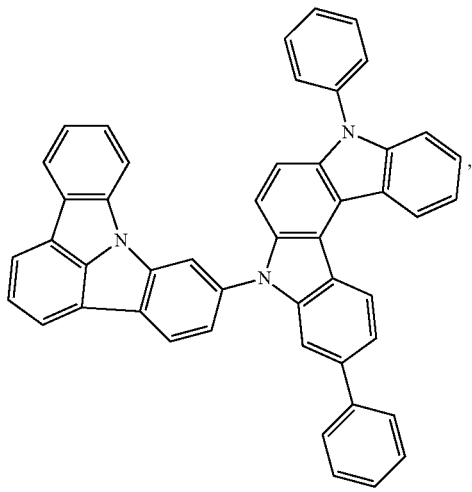
Compound D41
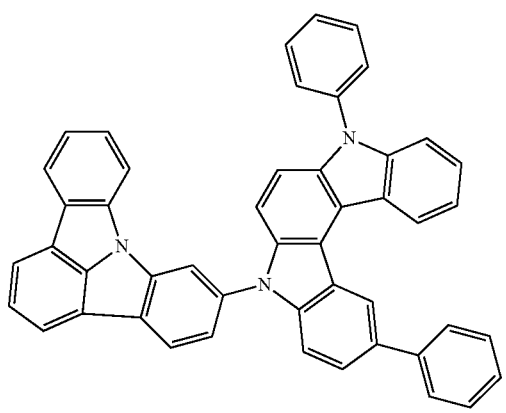
Compound D42
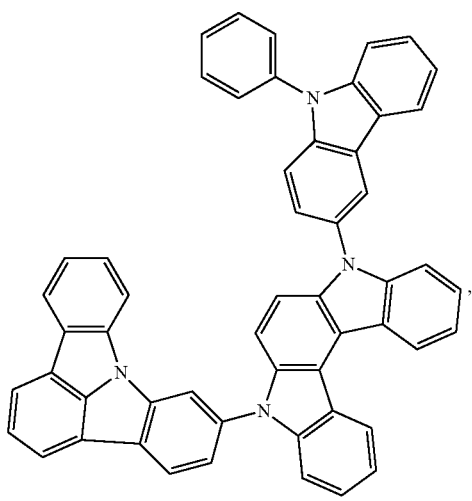

Compound D43

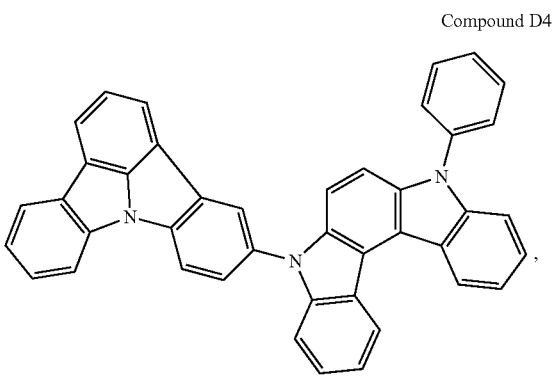

Compound D44

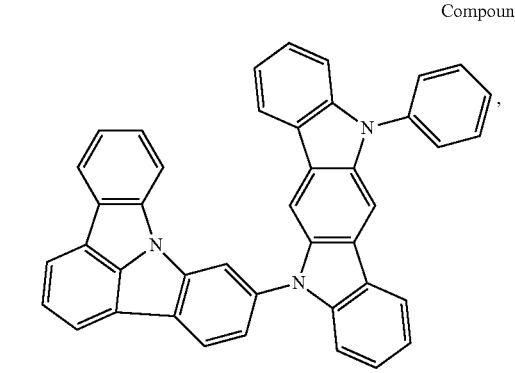

Compound D45

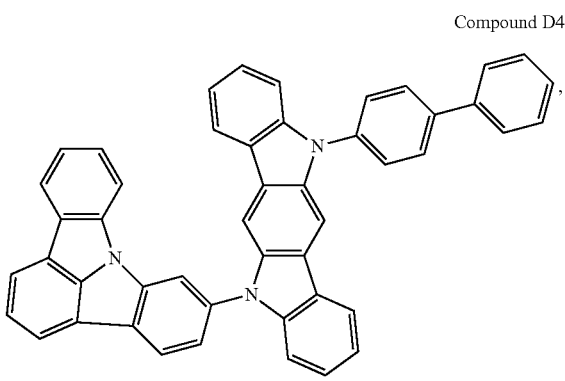

Compounds E1, E2 and E3 each
represented by the formula

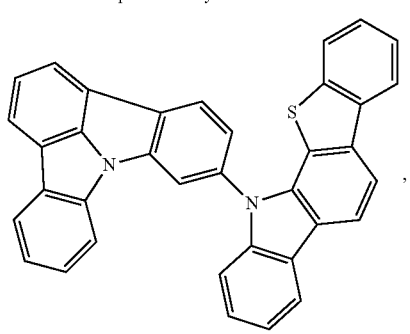

wherein in Compound E1, X = O,
in Compound E2, X = S, and
in Compound E3, X = Se Compounds E4, E5 and E6 each
represented by the formula

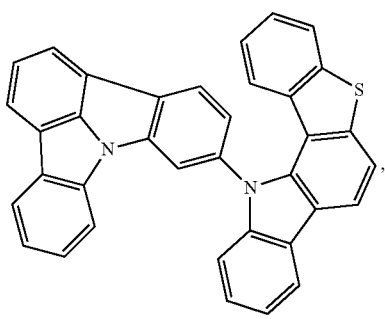

wherein in Compound E4, X = O,
in Compound E5, X = S, and
in Compound E6, X = Se Compounds E7, E8 and E9 each
represented by the formula

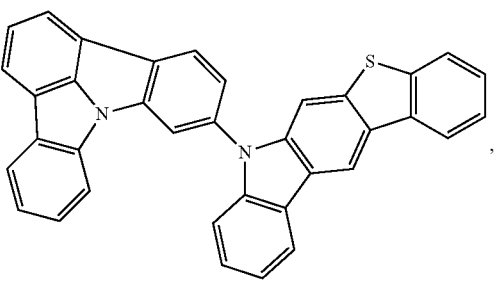

wherein in Compound E7, X = O,
in Compound E8, X = S, and
in Compound E9, X = Se Compounds E10, E11 and E12 each
represented by the formula

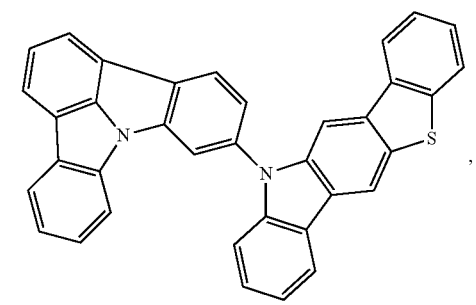

wherein in Compound E10, X = O,
in Compound E11, X = S, and
in Compound E12, X = Se Compounds E13, E14 and E15 each
represented by the formula

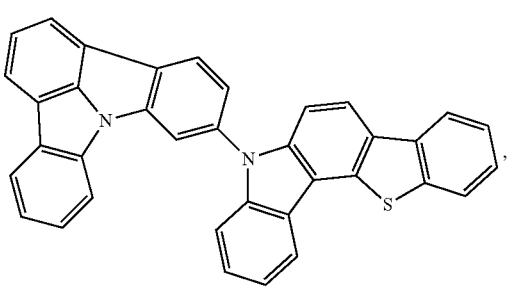

wherein in Compound E13, X = O,
in Compound E14, X = S, and
in Compound E15, X = Se Compounds E16, E17 and E18 each represented by the formula

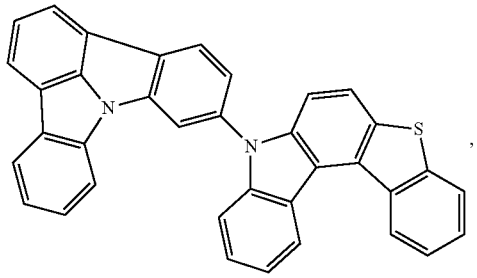

wherein in Compound E16, X = O,
in Compound E17, X = S, and
in Compound E18, X = Se Compound F1

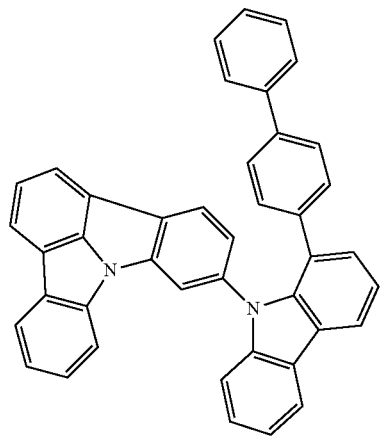

Compound F2

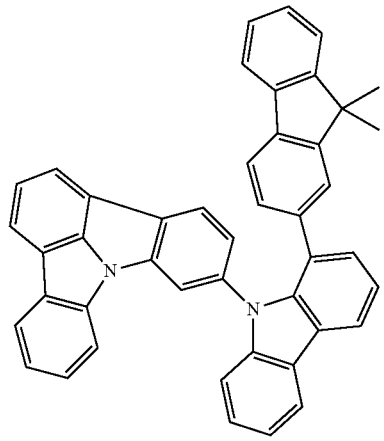

Compound F3

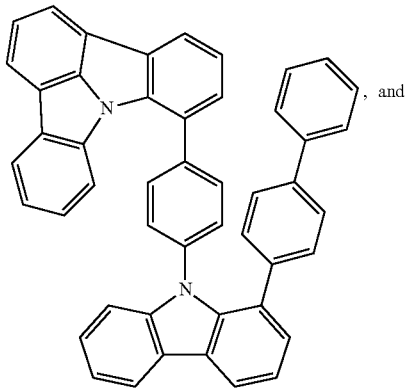

, and

Compound F4

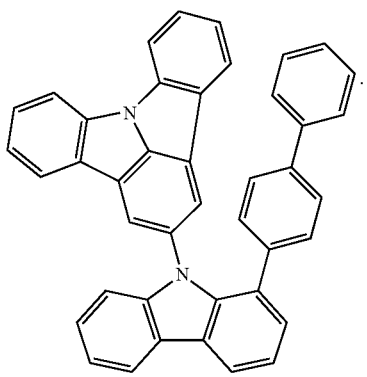

According to another aspect of the present disclosure, a first organic light emitting device (OLED) is also provided. The first organic light emitting device comprises, an anode, a cathode, and an organic layer that is disposed between the anode and the cathode. The organic layer comprises a compound having a formula selected from the group consisting of:

Formula I

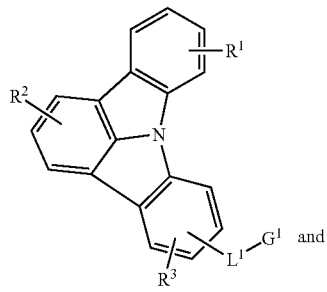

and

Formula II

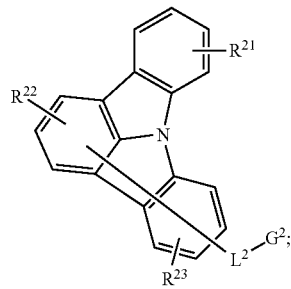

wherein $L^1$ is selected from the group consisting of a direct bond, phenyl, biphenyl, terphenyl, fluorene, carbazole, pyridine, pyrimidine, pyrazine, pyridazine, triazine, naphthalene, anthracene, and combinations thereof;

wherein $G^1$ is selected from the group consisting of:

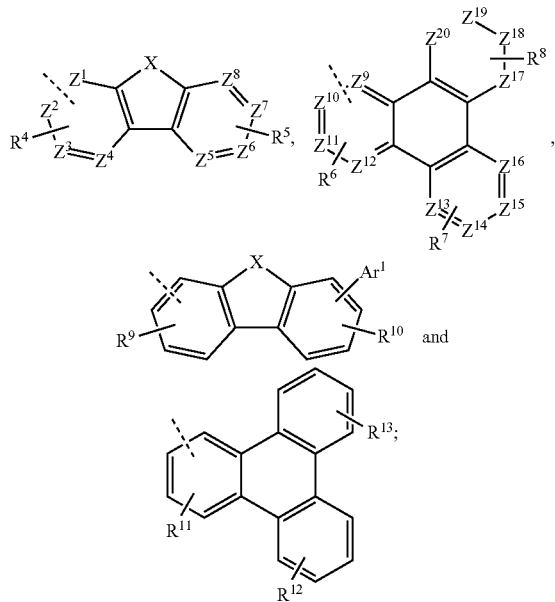

wherein X is selected from the group consisting of oxygen, sulfur and selenium;

wherein $R^1$, $R^5$, $R^7$, $R^8$, $R^{12}$, $R^{13}$, and $R^{21}$ each independently represent mono, di, tri, or tetra substitution, or no substitution;

wherein $R^2$, $R^3$, $R^4$, $R^5$, $R^6$, $R^9$, $R^{10}$, $R^{11}$, $R^{22}$, and $R^{23}$ each independently represent mono, di, or tri substitution, or no substitution;

wherein $R^1$ to $R^{13}$, and $R^{21}$ to $R^{23}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;

wherein $Z^1$ to $Z^{20}$ are each independently selected from the group consisting of carbon and nitrogen;

wherein at least one of $Z^1$, $Z^2$, $Z^3$, $Z^4$, $Z^5$, $Z^6$, $Z^7$ and $Z^8$ is nitrogen; and at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen;

wherein when any of $Z^1$ to $Z^{20}$ is nitrogen, there is no substitution on that nitrogen;

wherein $L^1$ and $G^1$ are bonded together by a C—C bond;

wherein $Ar^1$ is selected from the group consisting of benzene, biphenyl, terphenyl, triphenylene, fluorene, dibenzofuran, dibenzothiophene, dibenzoselenophene, naphthalene, phenanthrene, carbazole, pyridine, pyrimidine, pyrazine, pyridazine, triazine, azatriphenylene, aza-fluorene, aza-dibenzofuran, aza-dibenzothiophene, aza-dibenzoselenophene, aza-carbazole, quinolone, quinazoline, and combinations thereof;

wherein $L^1$ and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, carbazole, pyridine, pyrimidine, pyrazine, pyridazine, triazine, quinolone, phenanthroline, aza-dibenzofuran, aza-dibenzothiophene, aza-dibenzoselenophene, aza-fluorene and aza-triphenylene, aza-carbazole, and combinations thereof;

wherein $L^2$ is selected from the group consisting of a direct bond, alkyl, alkoxyl, aryl, heteroaryl, and combinations thereof;

wherein $G^2$ is selected from the group consisting of:

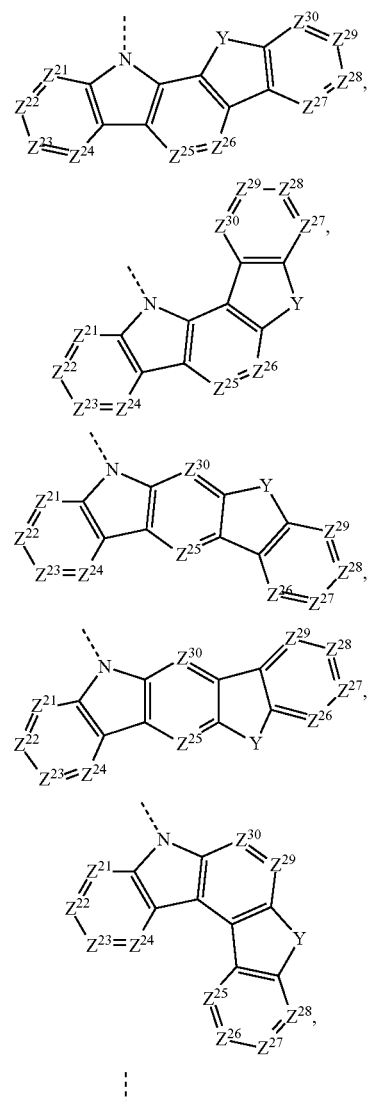

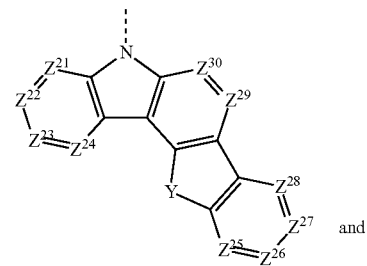

and

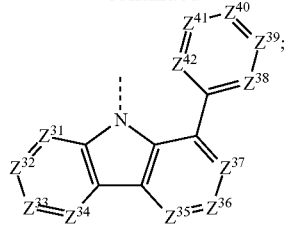

wherein $Z^{21}$ to $Z^{42}$ are each independently selected from the group consisting of C—$R^{20}$ and N;

wherein at least one of $Z^{21}$ to $Z^{42}$ is C—$R^{20}$;

wherein each $R^{20}$ can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any adjacent substituents are optionally joined to form a ring;

wherein Y is selected from the group consisting of: O, S, Se, $BR^{B1}$, $NR^{B2}$, $PR^{B3}$, and $CR^{B4}R^{B5}$;

wherein $R^{B1}$, $R^{B2}$, $R^{B3}$, $R^{B4}$ and $R^{B5}$ are each independently selected from the group consisting of hydrogen, deuterium, alkyl, cycloalkyl, heteroalkyl, arylalkyl, alkoxy, aryloxy, silyl, alkenyl, cycloalkenyl, heteroalkenyl, alkynyl, aryl, heteroaryl, and combinations thereof;

wherein $R^{B4}$ and $R^{B5}$ are optionally jointed to form a ring;

wherein $L^2$ is optionally further substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; and wherein the compounds of Formula I and Formula II each contains at most one non-fused carbazole moiety.

In the first OLED, the organic layer can be an emissive layer and the compound of Formula I or Formula II is a host. In some embodiments of the first organic light emitting device, the organic layer further comprises a phosphorescent emissive dopant; wherein the emissive dopant is a transition metal complex having at least one ligand or part of the ligand if the ligand is more than bidentate selected from the group consisting of:

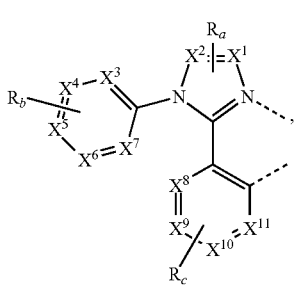

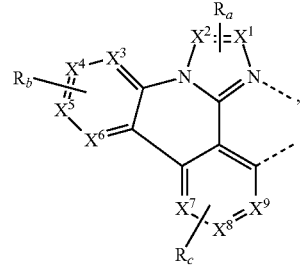

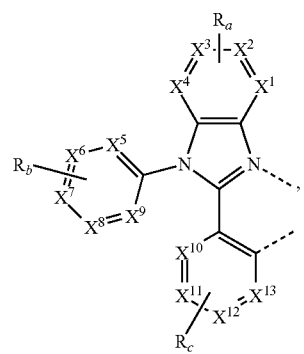

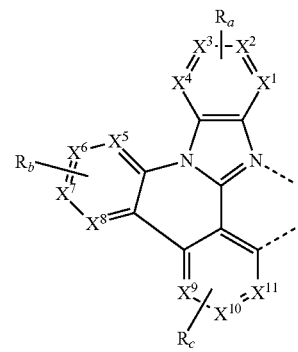
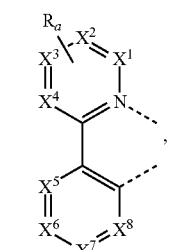

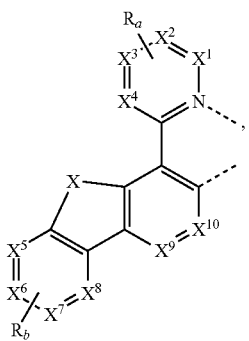
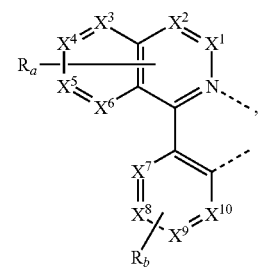

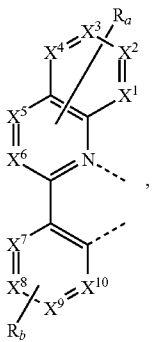
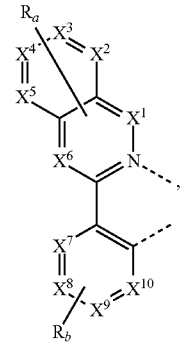

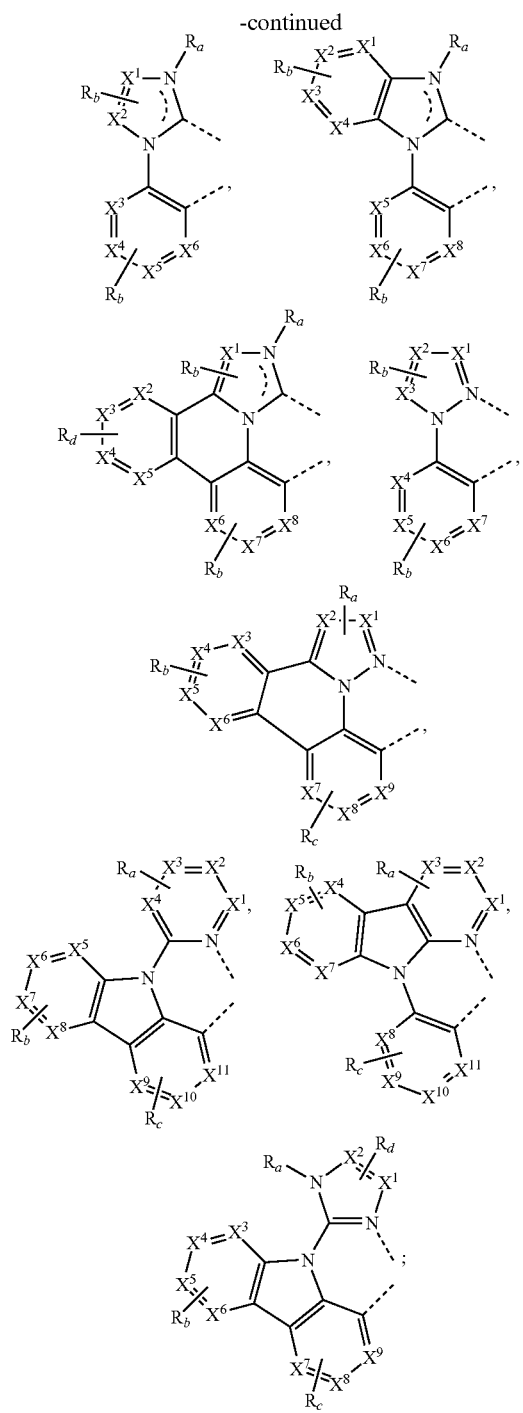

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R^a$, $R_b$, $R_c$, and $R_d$ are optionally fused or joined to form a ring or form a multidentate ligand.

In some embodiments of the first OLED, the organic layer is a blocking layer and the compound having Formula I or Formula II is a blocking material in the organic layer.

In other embodiments of the first OLED, the organic layer is an electron transporting layer and the compound having Formula I or Formula II is an electron transporting material in the organic layer.

In other embodiments of the first OLED, the OLED device is incorporated into a device selected from the group consisting of a consumer product, an electronic component module, an organic light-emitting device, and a lighting panel.

The organic layer can include one or more emitter dopants. The emitter dopants can be phosphorescent dopants and/or fluorescent dopants.

In yet another aspect of the present disclosure, a formulation comprising a first compound having a formula of

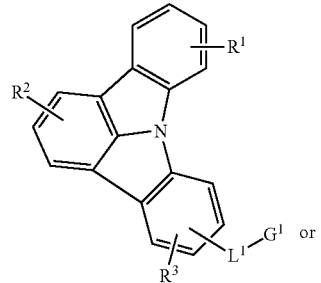

Formula I

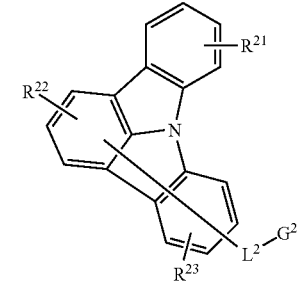

Formula II defined above is disclosed. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

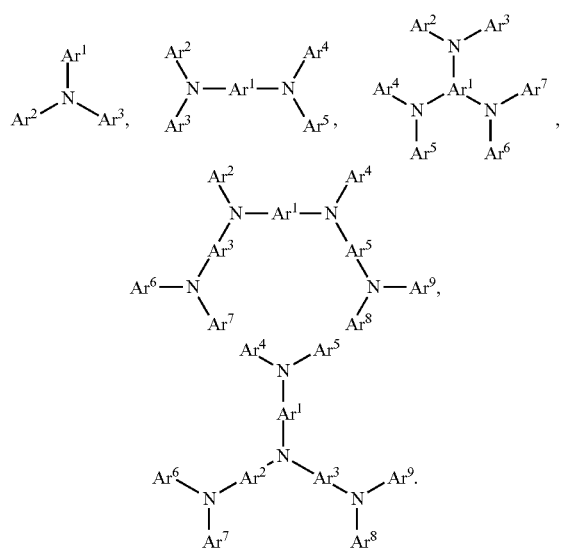

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

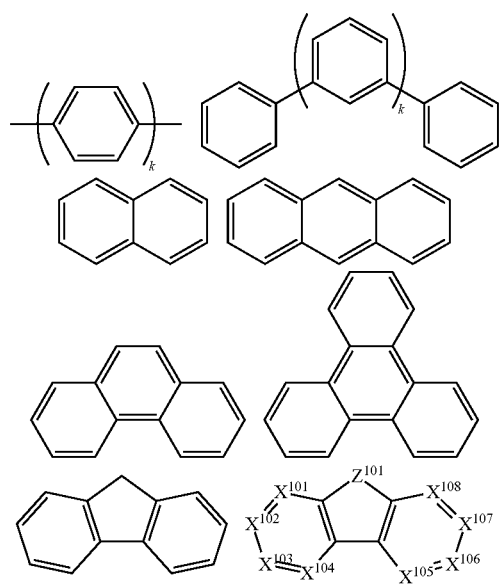

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not are limited to the following general formula:

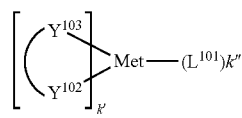

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

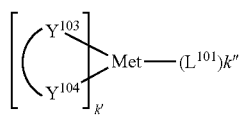

wherein Met is a metal; $(Y^{103}-Y^{104})$ is a bidentate ligand. $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

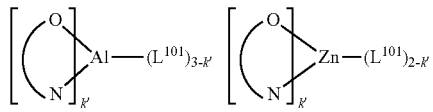

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

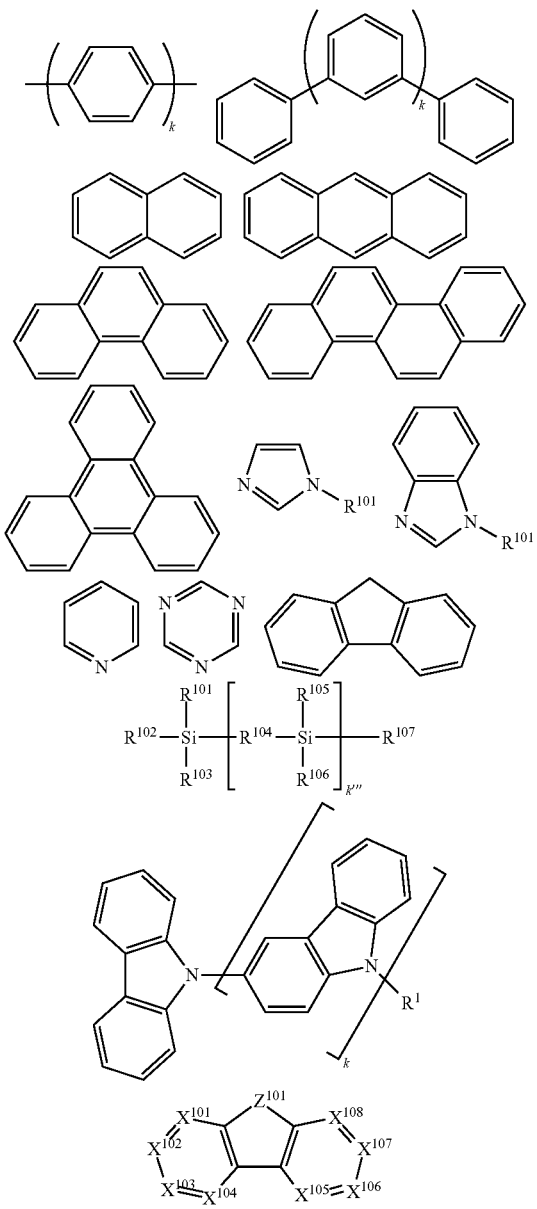

-continued

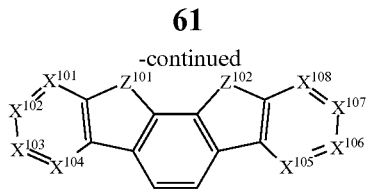

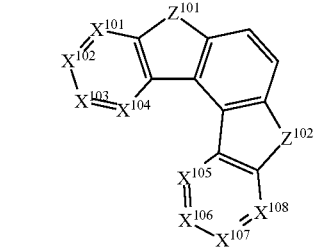

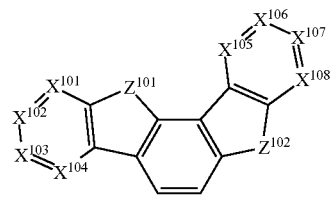

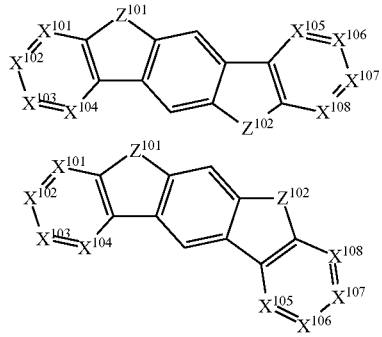

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

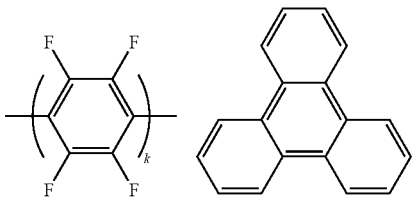
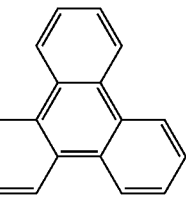

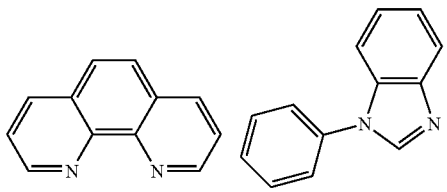
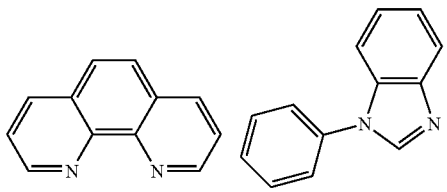

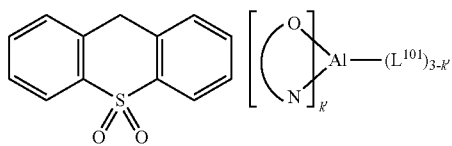
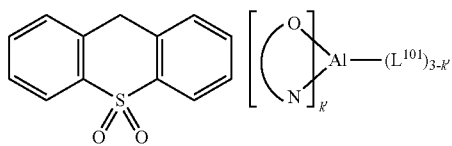
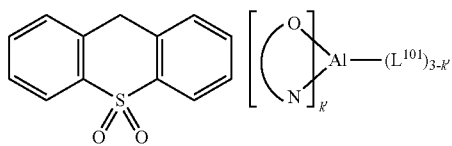

wherein k is an integer from 1 to 20; $L^{101}$ is an another ligand, k' is an integer from 1 to 3.

ETL:

Electron transport layer (ETL) may include a material capable of transporting electrons.

Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

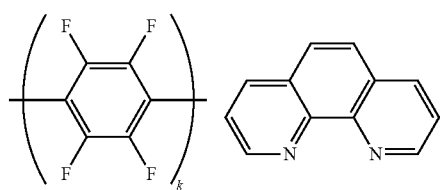
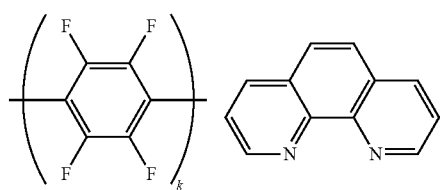

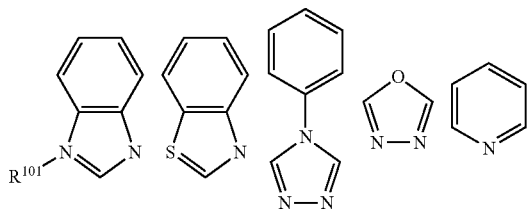
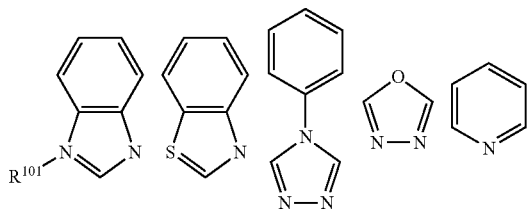

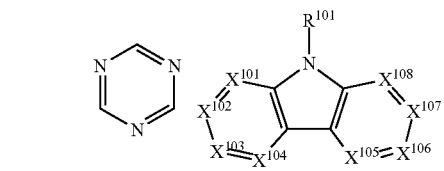

-continued

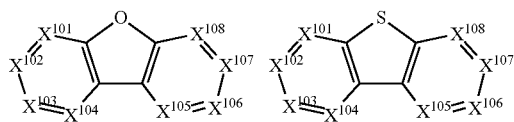

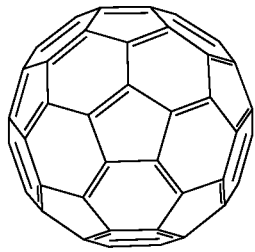

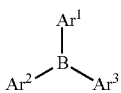

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

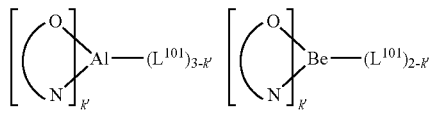

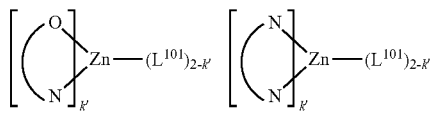

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
| --- | --- | --- |
| | Hole injection materials | |
| Phthalocyanine and porphyrin compounds | 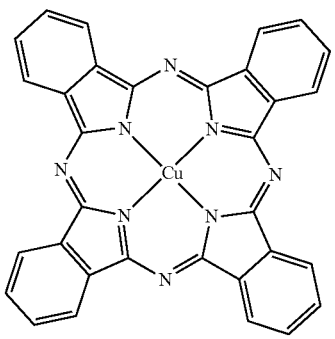 | Appl. Phys. Lett. 69, 2160 (1996) |

TABLE A-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |
| Triarylamine or polythiophene polymers with conductivity dopants | | EP1725079A1 and |

TABLE A-continued
| MATERIAL | EXAMPLES OF MATERIAL | PUBLICATIONS |
|---|---|---|
| | 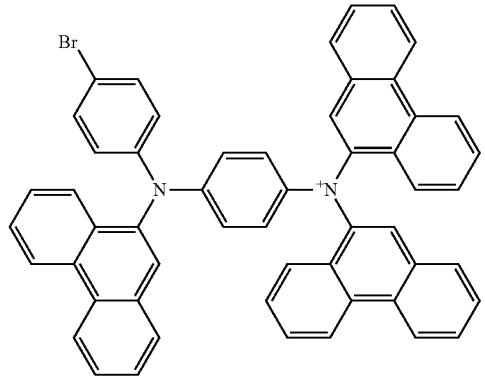 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 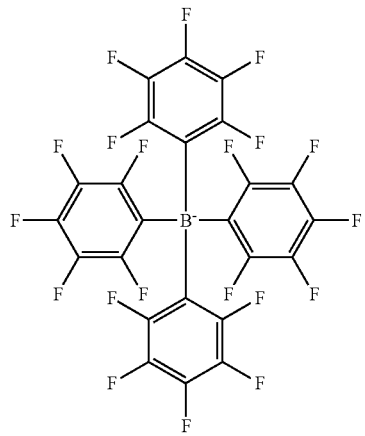 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 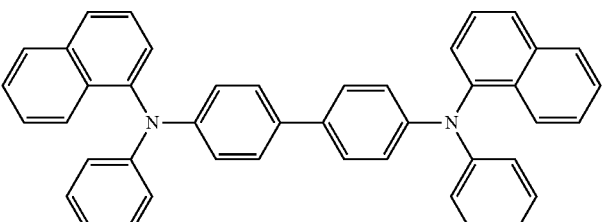 | US20050123751<br>SID Symposium Digest, 37, 923 (2006)<br>WO2009018009 |
| n-type semiconducting organic complexes | 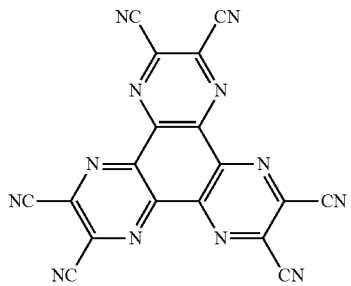 [SMILES: N#Cc1nc2c3nc(C#N)c(C#N)nc3c3nc(C#N)c(C#N)nc3c2nc1C#N] | US20020158242 |
| Metal organometallic complexes | 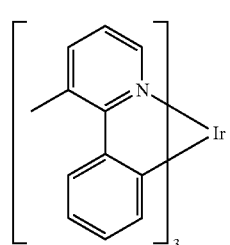 | US20060240279 |

TABLE A-continued
| MATERIAL | EXAMPLES OF MATERIAL | PUBLICATIONS |
| --- | --- | --- |
| Cross-linkable compounds | 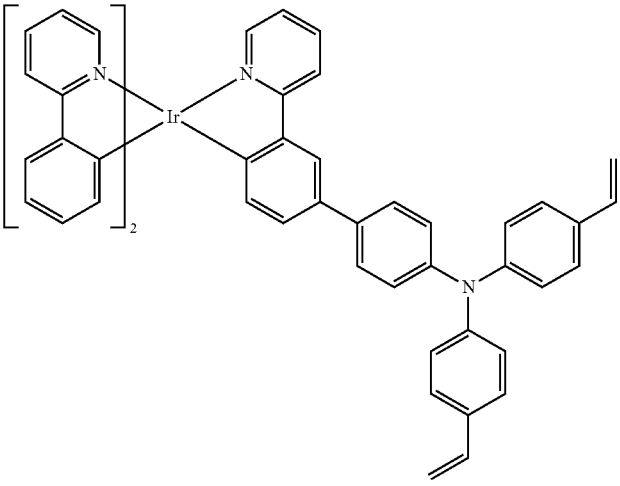 | US20080220265 |
| Polythiophene based polymers and copolymers | 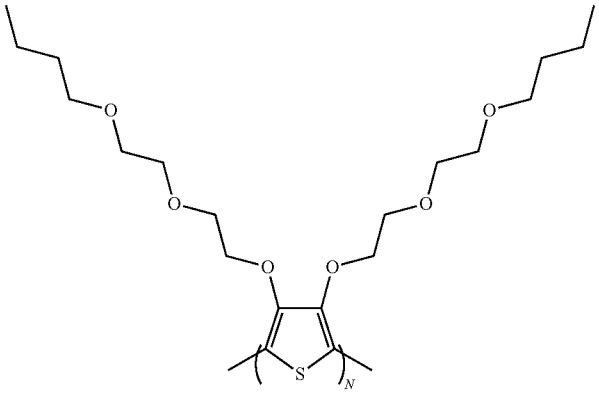 | WO 2011075644<br>EP2350216 |
Hole transporting materials
| | | |
| --- | --- | --- |
| Triarylamines (e.g., TPD, α-NPD) | 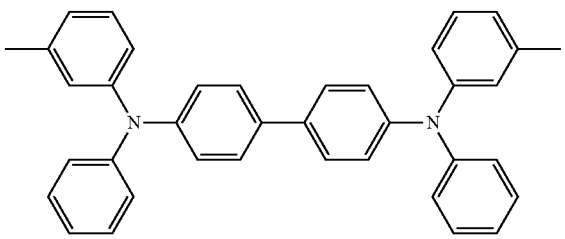 | Appl. Phys. Lett. 51, 913 (1987) |
| | 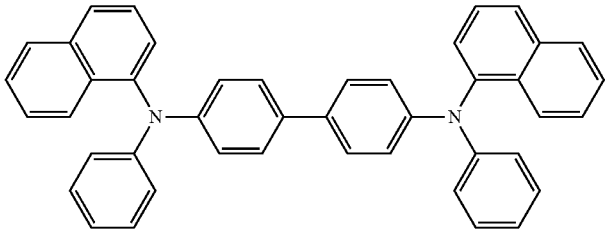 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |

TABLE A-continued
| MATERIAL | EXAMPLES OF MATERIAL | PUBLICATIONS |
|---|---|---|
| | 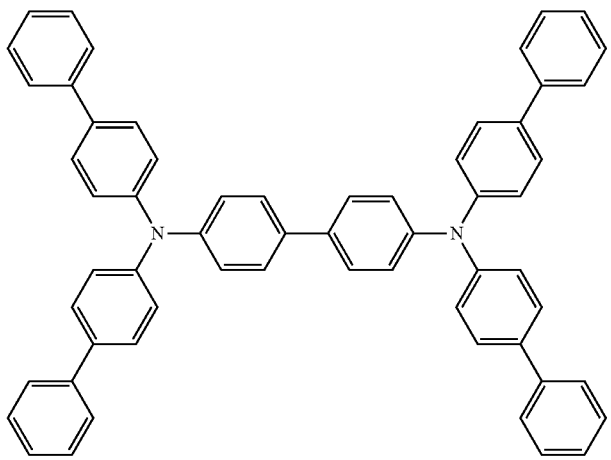 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 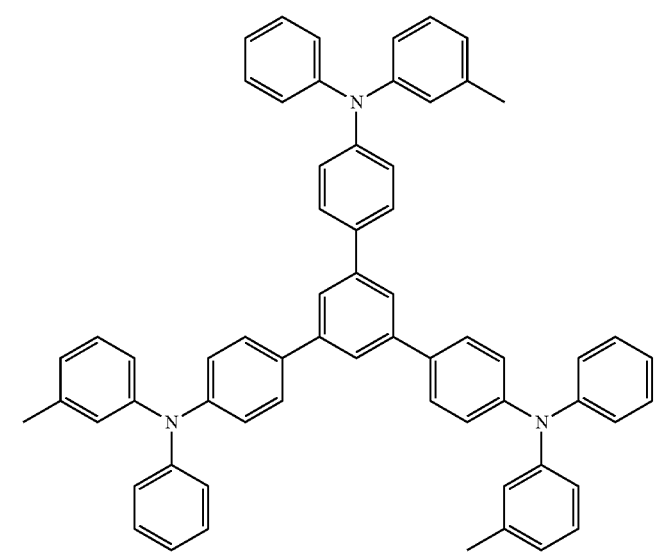 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 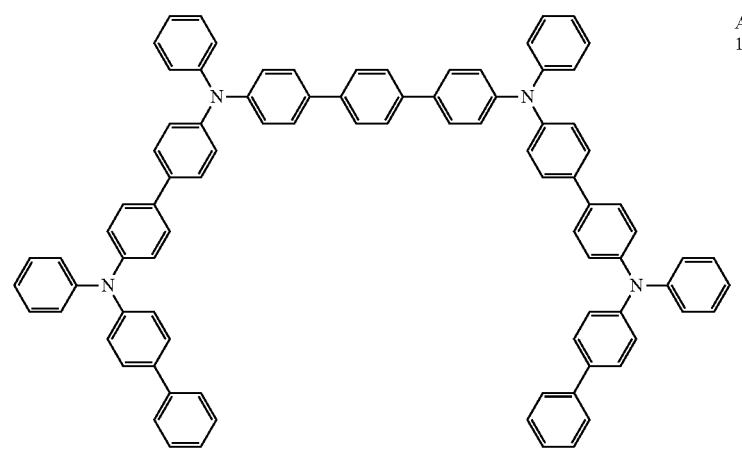 | Appl. Phys. Lett. 90, 183503 (2007) |

TABLE A-continued
| MATERIAL | EXAMPLES OF MATERIAL | PUBLICATIONS |
|---|---|---|
| | 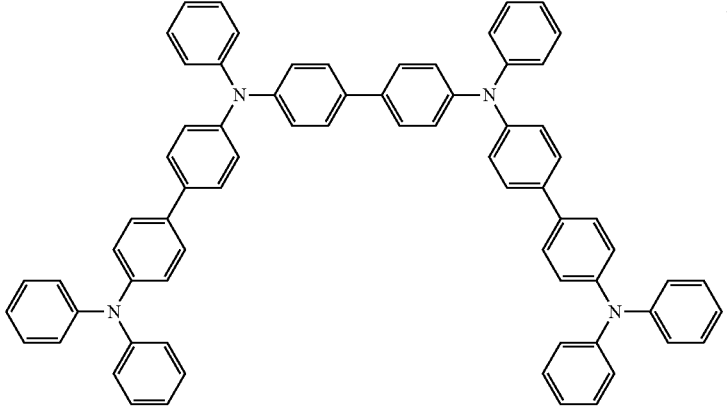 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spirofluorene core | 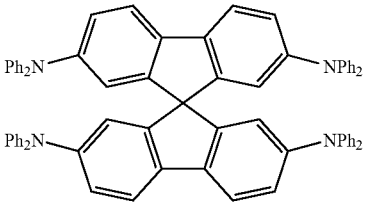 | Synth. Met. 91, 209 (1997) |
| Arylamine carbazole compounds | 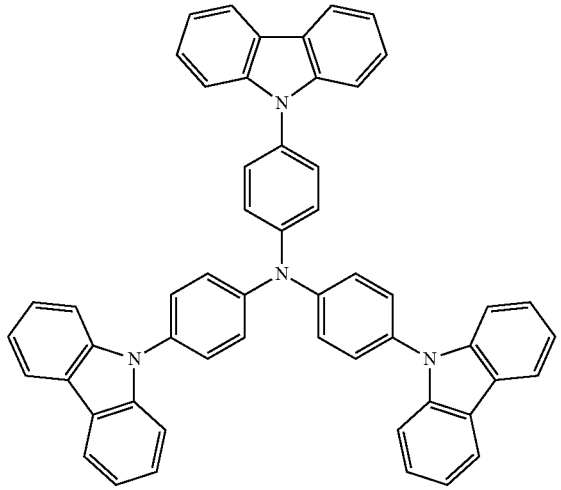 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/ (di)benzofuran | 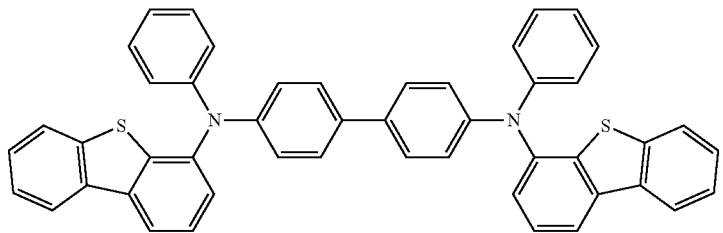 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |

TABLE A-continued
| MATERIAL | EXAMPLES OF MATERIAL | PUBLICATIONS |
|---|---|---|
| Indolocarbazoles | 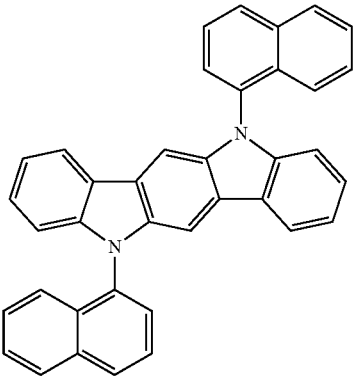 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 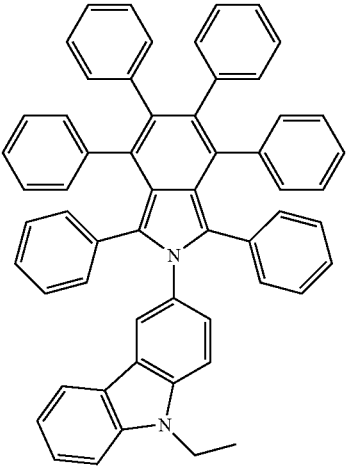 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 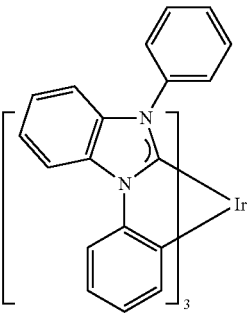 | US20080018221 |
Phosphorescent OLED host materials
Red hosts
| | | |
|---|---|---|
| Arylcarbazoles | 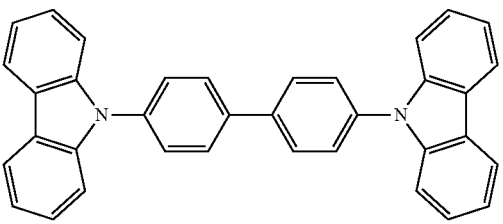 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE A-continued

| MATERIAL | EXAMPLES OF MATERIAL | PUBLICATIONS |
| --- | --- | --- |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE A-continued
| MATERIAL | EXAMPLES OF MATERIAL | PUBLICATIONS |
|---|---|---|
| Zinc complexes | 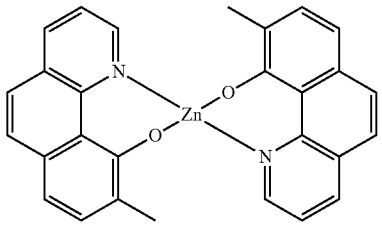 | WO2010056066 |
| Chrysene based compounds | 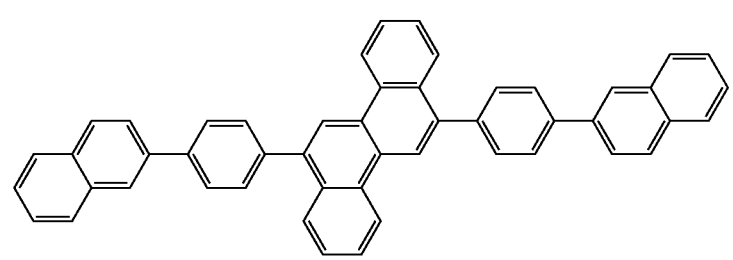 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| | | |
|---|---|---|
| Arylcarbazoles | 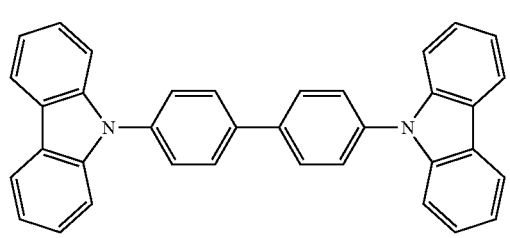 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 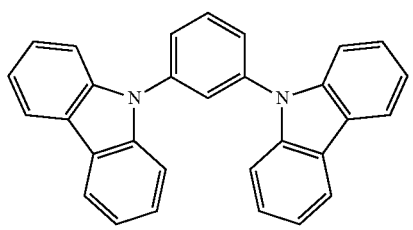 [SMILES: c1cc(-n2c3ccccc3c3ccccc32)cc(-n2c3ccccc3c3ccccc32)c1] | US20030175553 |
| | 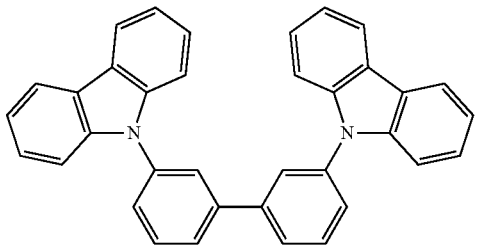 [SMILES: c1cc(-c2cccc(-n3c4ccccc4c4ccccc43)c2)cc(-n2c3ccccc3c3ccccc32)c1] | WO2001039234 |
| Aryltriphenylene compounds | 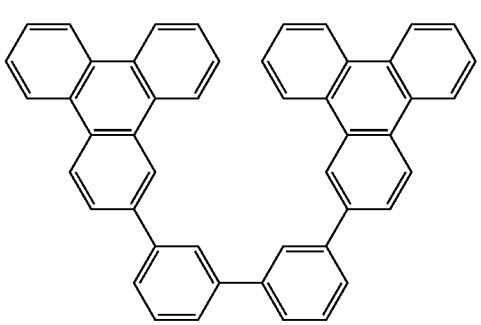 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE A-continued
| MATERIAL | EXAMPLES OF MATERIAL | PUBLICATIONS |
|---|---|---|
| | 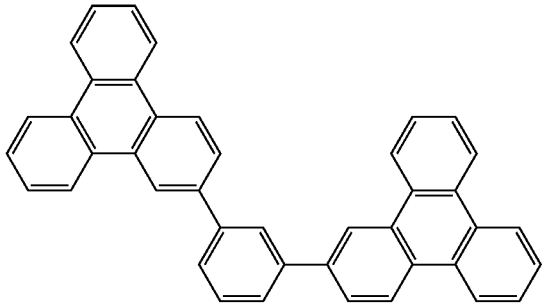 [SMILES: c1cc(-c2ccc3c4ccccc4c4ccccc4c3c2)cc(-c2ccc3c4ccccc4c4ccccc4c3c2)c1] | US20060280965 |
| | 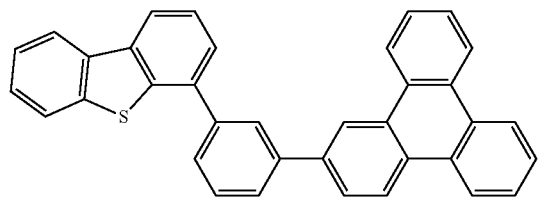 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 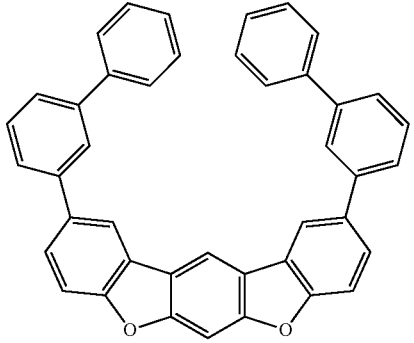 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 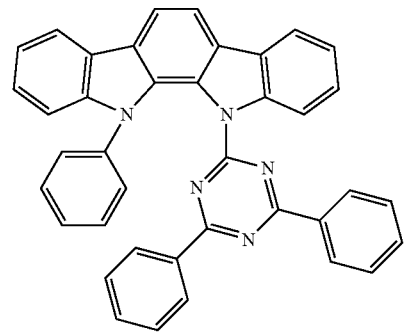 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 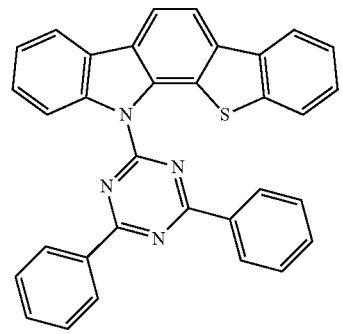 [SMILES: c1ccc(-c2nc(-c3ccccc3)nc(-n3c4ccccc4c4ccc5c6ccccc6sc5c43)n2)cc1] | WO2010107244 |

TABLE A-continued
| MATERIAL | EXAMPLES OF MATERIAL | PUBLICATIONS |
|---|---|---|
| Aza-carbazole/DBT/DBF | 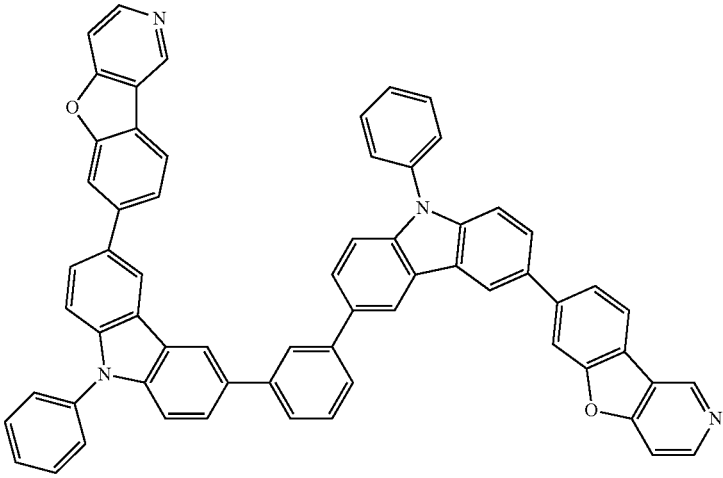 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 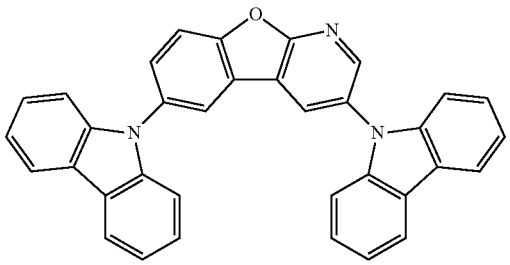 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 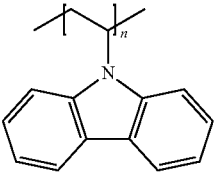 | Appl. Phys. Lett. 77, 2280 (2000) |
| Spirofluorene compounds | 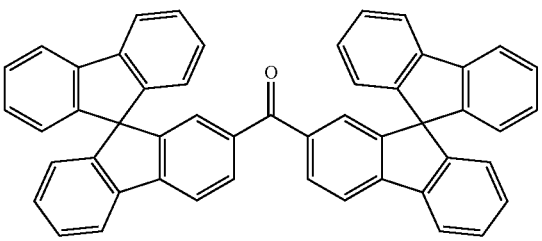 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 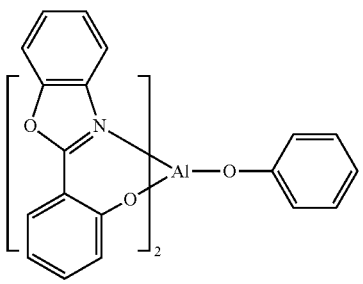 | WO2005089025 |

TABLE A-continued
| MATERIAL | EXAMPLES OF MATERIAL | PUBLICATIONS |
|---|---|---|
| | 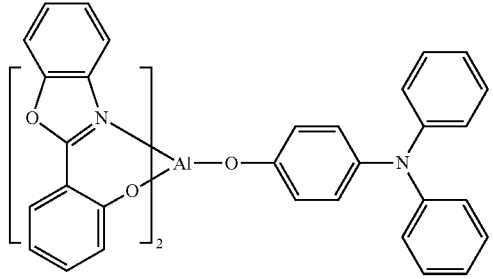 | WO2006132173 |
| | 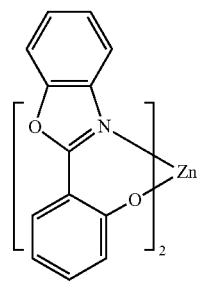 | JP200511610 |
| Spirofluorene-carbazole compounds | 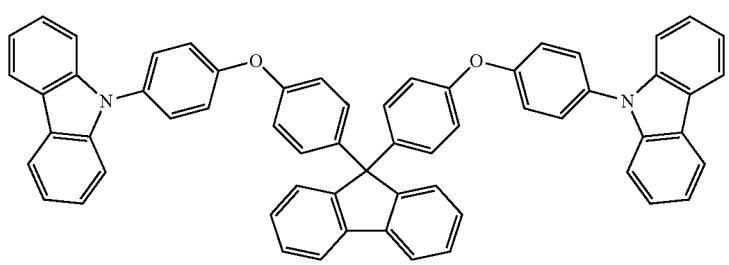 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 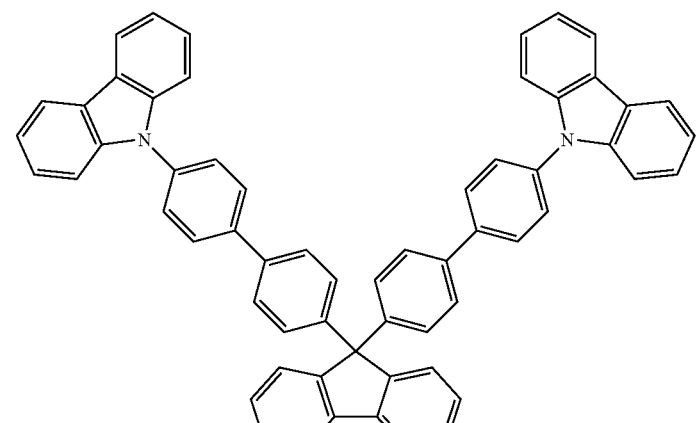 | JP2007254297 |
| Indolocarbazoles | 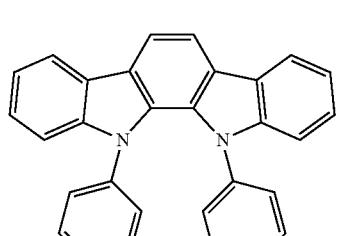 | WO2007063796 |

TABLE A-continued
| MATERIAL | EXAMPLES OF MATERIAL | PUBLICATIONS |
|---|---|---|
| | 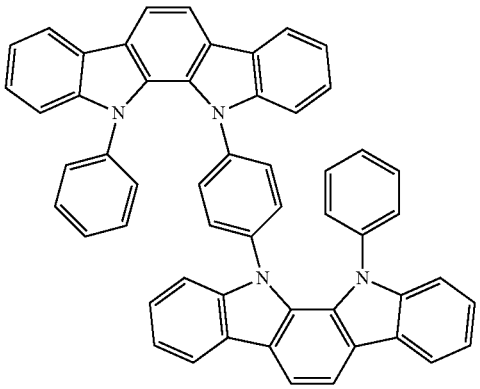 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 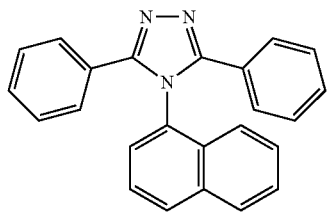 [SMILES: c1ccc(-c2nnc(-c3ccccc3)n2-c2cccc3ccccc23)cc1] | J. Appl. Phys. 90, 5048 (2001) |
| | 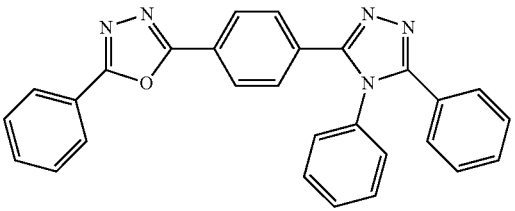 [SMILES: c1ccc(-c2nnc(-c3ccc(-c4nnc(-c5ccccc5)n4-c4ccccc4)cc3)o2)cc1] | WO2004107822 |
| Tetraphenylene complexes | 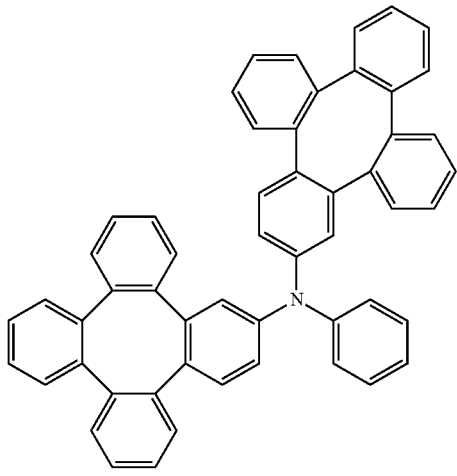 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 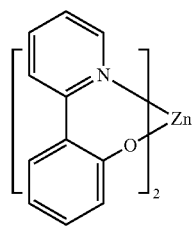 | WO2005030900 |

TABLE A-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |
| Dibenzothiophene/Dibenzofuran-carbazole compounds | | WO2006114966, US20090167162 |
| | | US20090167162 |
| | | WO2009086028 |

TABLE A-continued
| MATERIAL | EXAMPLES OF MATERIAL | PUBLICATIONS |
|---|---|---|
| | 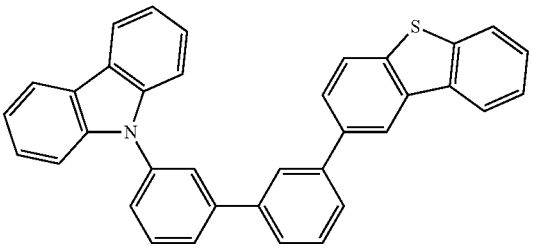 [SMILES: c1cc(-c2cccc(-n3c4ccccc4c4ccccc43)c2)cc(-c2ccc3sc4ccccc4c3c2)c1] | US20090030202, US20090017330 |
| | 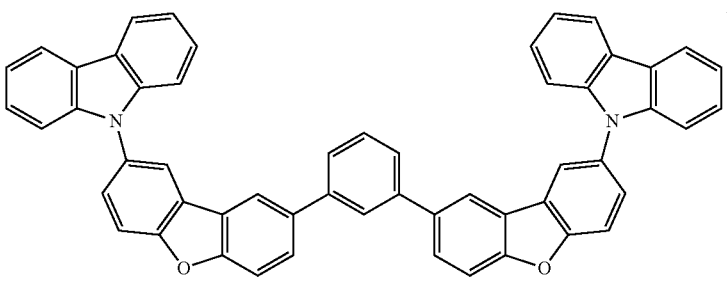 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 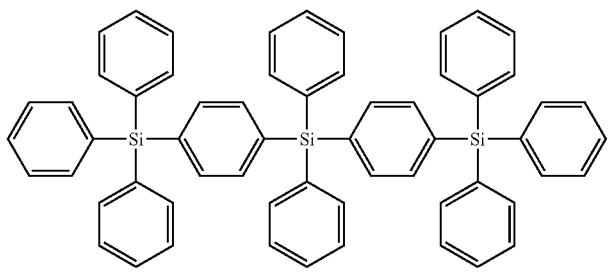 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 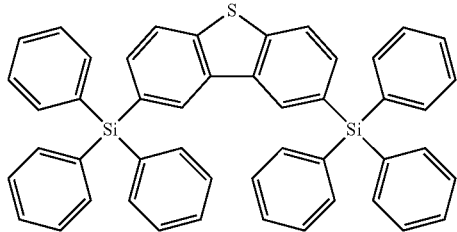 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 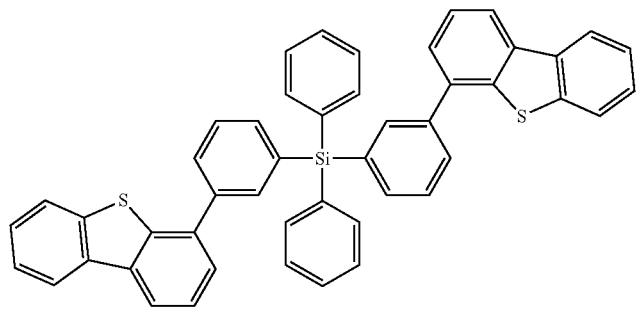 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 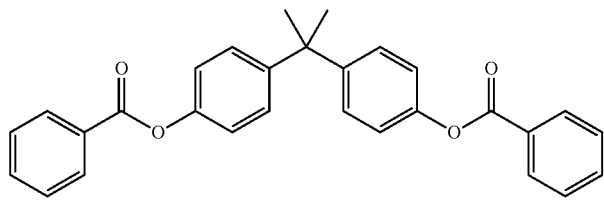 [SMILES: CC(C)(c1ccc(OC(=O)c2ccccc2)cc1)c1ccc(OC(=O)c2ccccc2)cc1] | WO2006100298 |

TABLE A-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

TABLE A-continued

| MATERIAL | EXAMPLES OF MATERIAL | PUBLICATIONS |
|---|---|---|
| | | US20080261076 US20100090591 |
| | | US20070087321 |
| | | Adv. Mater. 19, 739 (2007) |
| | | WO2009100991 |
| | | WO2008101842 |

TABLE A-continued
| MATERIAL | EXAMPLES OF MATERIAL | PUBLICATIONS |
|---|---|---|
| | 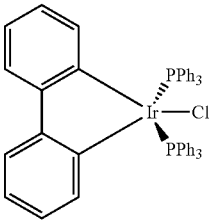 | U.S. Pat. No. 7,232,618 |
| Platinum(II) organometallic complexes | 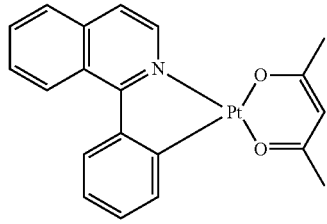 | WO2003040257 |
| | 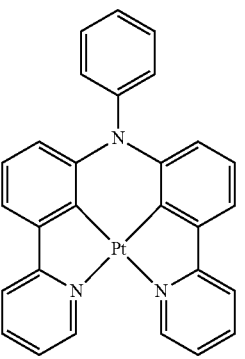 | US20070103060 |
| Osmium(III) complexes | 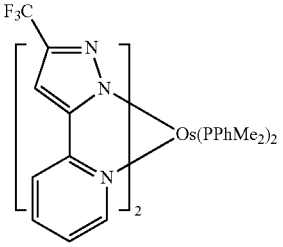 | Chem. Mater. 17, 3532 (2005) |
| Ruthenium(II) complexes | 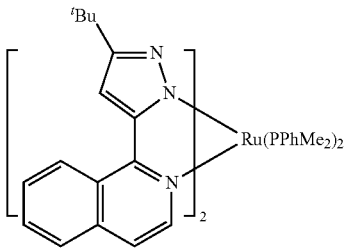 | Adv. Mater. 17, 1059 (2005) |
| Rhenium (I), (II), and (III) complexes | 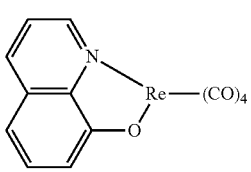 | US20050244673 |

TABLE A-continued
| MATERIAL | EXAMPLES OF MATERIAL | PUBLICATIONS |
|---|---|---|
| | Green dopants | |
| Iridium(III) organometallic complexes | 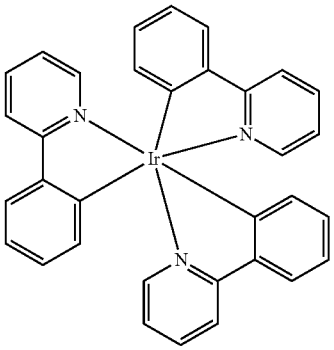<br>and its derivatives | Inorg. Chem. 40, 1704 (2001) |
| | 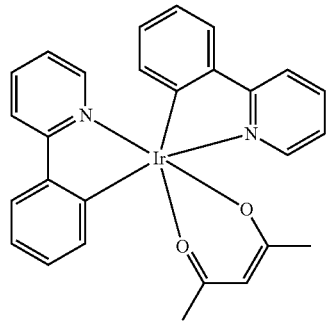 | US20020034656 |
| | 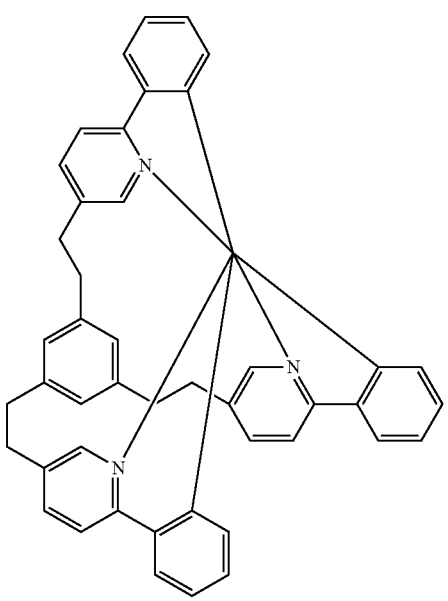 | U.S. Pat. No. 7,332,232 |

TABLE A-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE A-continued

| MATERIAL | EXAMPLES OF MATERIAL | PUBLICATIONS |
|---|---|---|
| | | U.S. Pat. No. 6,921,915 |
| | | US20100244004 |
| | | U.S. Pat. No. 6,687,266 |
| | | Chem. Mater. 16, 2480 (2004) |
| | | US20070190359 |

TABLE A-continued

| MATERIAL | EXAMPLES OF MATERIAL | PUBLICATIONS |
|---|---|---|
| | | US 20060008670<br>JP2007123392 |
| | | WO2010086089,<br>WO2011044988 |
| | | Adv. Mater. 16, 2003<br>(2004) |
| | | Angew. Chem. Int. Ed.<br>2006, 45, 7800 |
| | | WO2009050290 |
| | | US20090165846 |

TABLE A-continued

| MATERIAL | EXAMPLES OF MATERIAL | PUBLICATIONS |
| --- | --- | --- |
| | | US20080015355 |
| | | US20010015432 |
| | | US20100295032 |
| Monomer for polymeric metal organometallic compounds | | U.S. Pat. No. 7,250,226, U.S. Pat. No. 7,396,598 |
| Pt(II) organometallic complexes, including polydentate ligands | | Appl. Phys. Lett. 86, 153505 (2005) |

TABLE A-continued
| MATERIAL | EXAMPLES OF MATERIAL | PUBLICATIONS |
|---|---|---|
| | 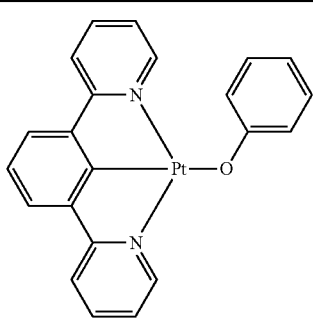 | Appl. Phys. Lett. 86, 153505 (2005) |
| | 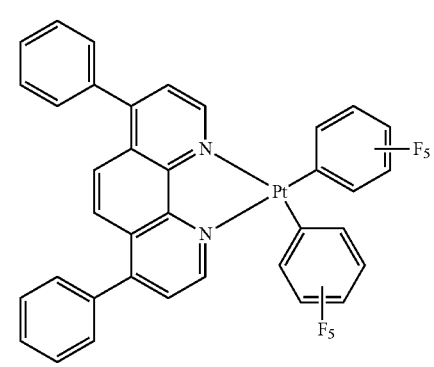 | Chem. Lett. 34, 592 (2005) |
| | 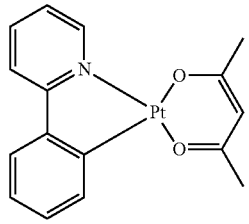 | WO2002015645 |
| | 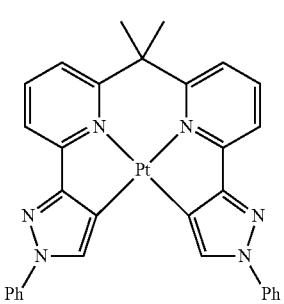 | US20060263635 |
| | 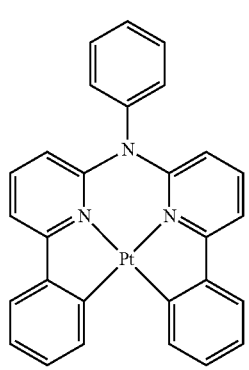 | US20060182992<br>US20070103060 |

TABLE A-continued
| MATERIAL | EXAMPLES OF MATERIAL | PUBLICATIONS |
|---|---|---|
| Cu complexes | 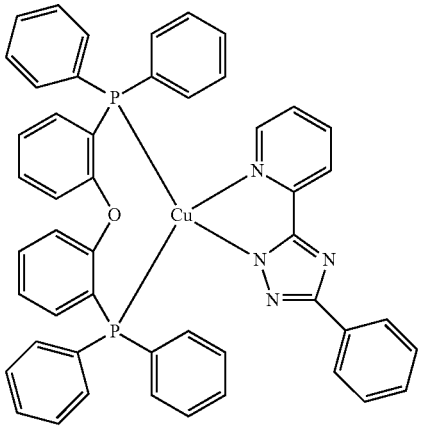 | WO2009000673 |
|  | 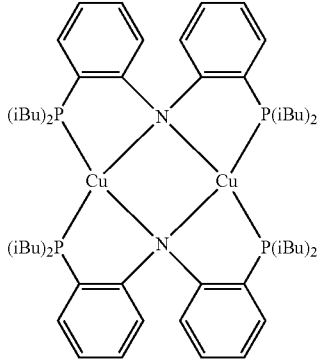 | US20070111026 |
| Gold complexes | 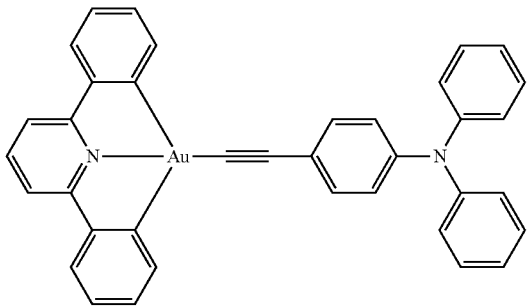 | Chem. Commun. 2906 (2005) |
| Rhenium(III) complexes | 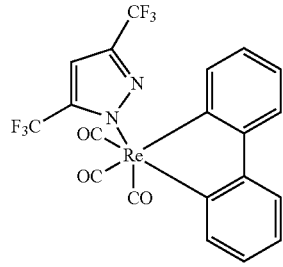 | Inorg. Chem. 42, 1248 (2003) |

TABLE A-continued
| MATERIAL | EXAMPLES OF MATERIAL | PUBLICATIONS |
|---|---|---|
| Osmium(II) complexes | 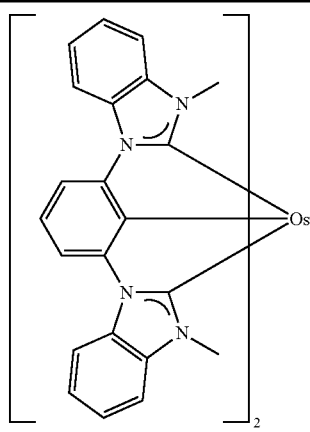 | U.S. Pat. No. 7,279,704 |
| Deuterated organometallic complexes | 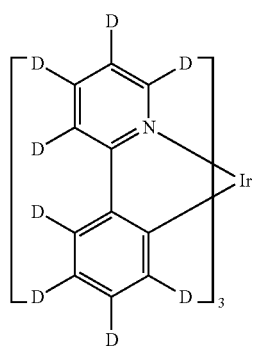 | US20030138657 |
| Organometallic complexes with two or more metal centers | 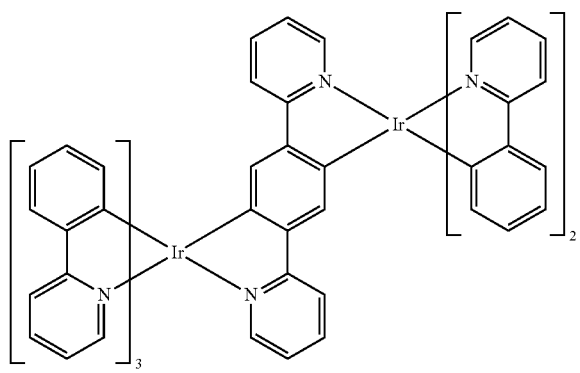 | US20030152802 |
| | 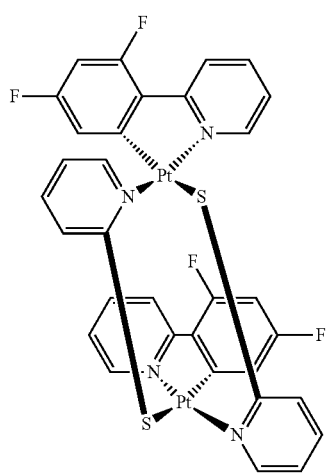 | U.S. Pat. No. 7,090,928 |

TABLE A-continued
| MATERIAL | EXAMPLES OF MATERIAL | PUBLICATIONS |
|---|---|---|
| | Blue dopants | |
| Iridium(III) organometallic complexes | 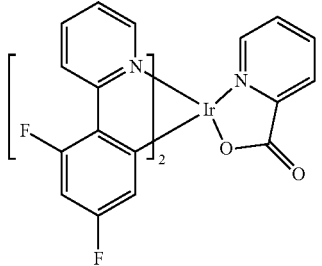 | WO2002002714 |
| | 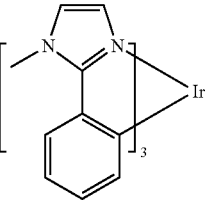 | WO2006009024 |
| | 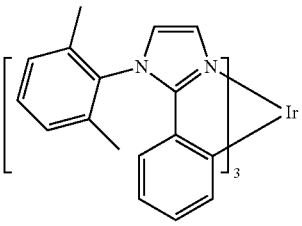 | US20060251923<br>US20110057559<br>US20110204333 |
| | 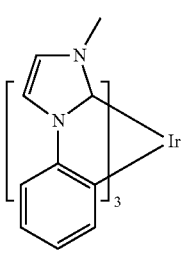 | U.S. Pat. No. 7,393,599,<br>WO2006056418,<br>US20050260441,<br>WO2005019373 |
| | 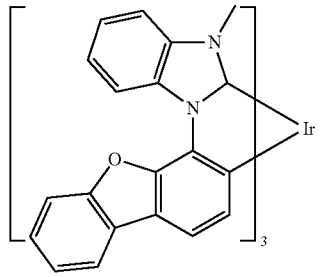 | U.S. Pat. No. 7,534,505 |

TABLE A-continued
| MATERIAL | EXAMPLES OF MATERIAL | PUBLICATIONS |
|---|---|---|
| | 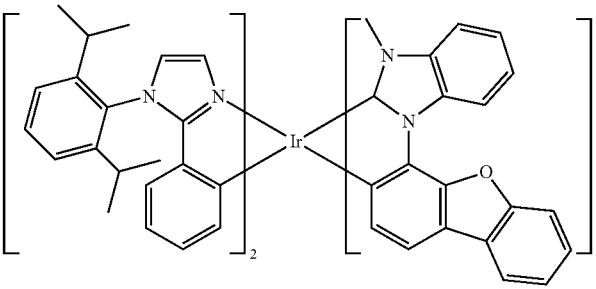 | WO2011051404 |
| | 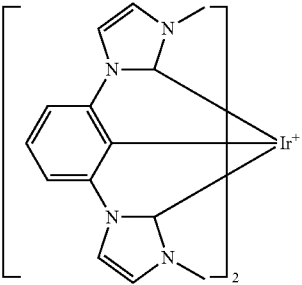 | U.S. Pat. No. 7,445,855 |
| | 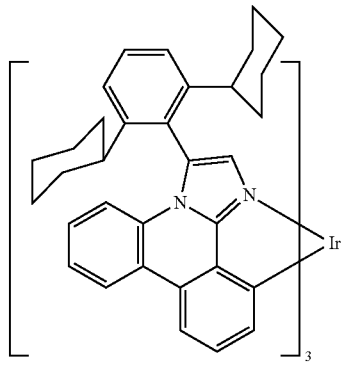 | US20070190359, US20080297033 US20100148663 |
| | 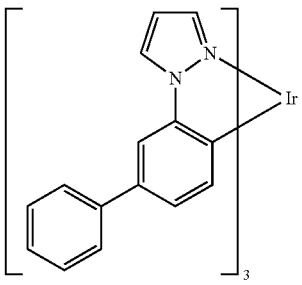 | U.S. Pat. No. 7,338,722 |
| | 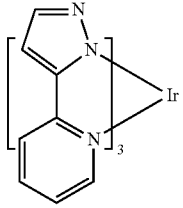 | US20020134984 |

TABLE A-continued

| MATERIAL | EXAMPLES OF MATERIAL | PUBLICATIONS |
|---|---|---|
| | | Angew. Chem. Int. Ed. 47, 4542 (2008) |
| | | Chem. Mater. 18, 5119 (2006) |
| | | Inorg. Chem. 46, 4308 (2007) |
| | | WO2005123873 |
| | | WO2005123873 |

| MATERIAL | EXAMPLES OF MATERIAL | PUBLICATIONS |
|---|---|---|
| | 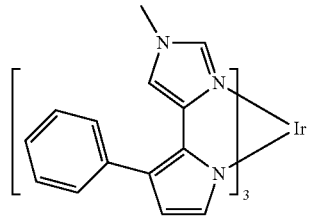 | WO2007004380 |
| | 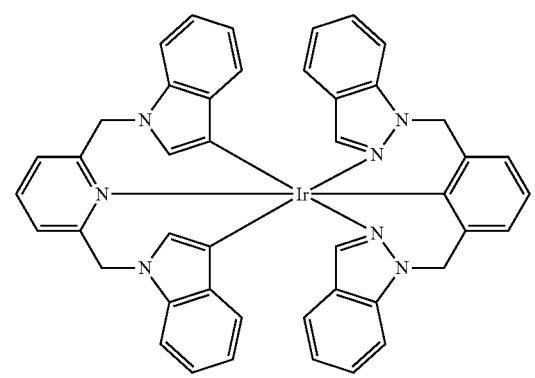 | WO2006082742 |
| Osmium(II) complexes | 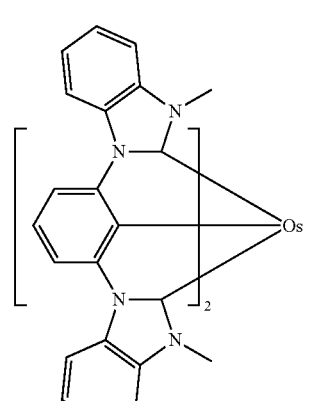 | U.S. Pat. No. 7,279,704 |
| | 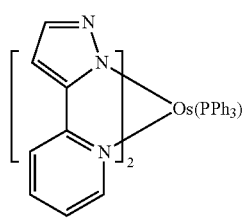 | Organometallics 23, 3745 (2004) |
| Gold complexes | 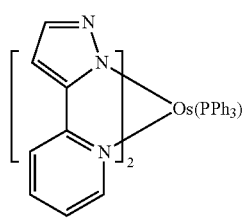 | Appl. Phys. Lett. 74, 1361 (1999) |
| Platinum(II) complexes | 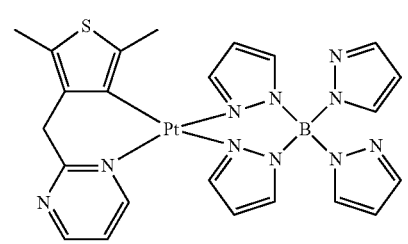 | WO2006098120, WO2006103874 |

TABLE A-continued

| MATERIAL | EXAMPLES OF MATERIAL | PUBLICATIONS |
| --- | --- | --- |
| Pt tetradentate complexes with at least one metal-carbene bond | 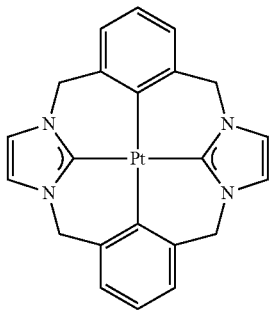 | U.S. Pat. No. 7,655,323 |
| Exciton/hole blocking layer materials | | |
| Bathocuprine compounds (e.g., BCP, BPhen) | 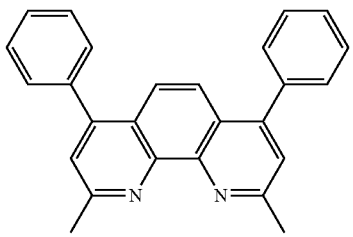 [SMILES: Cc1cc(-c2ccccc2)c2ccc3c(-c4ccccc4)cc(C)nc3c2n1] | Appl. Phys. Lett. 75, 4 (1999) |
|  | 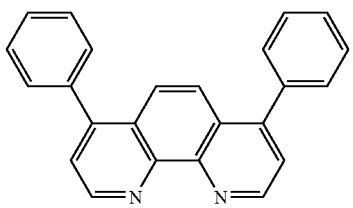 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 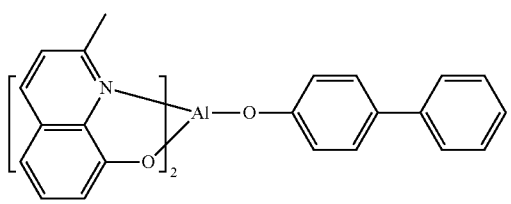 | Appl. Phys. Lett. 81, 162 (2002) |
| 5-member ring electron deficient heterocycles such as triazole, oxadiazole, imidazole, benzoimidazole | 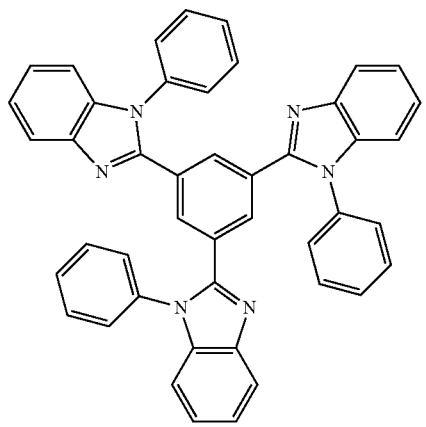 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE A-continued

| MATERIAL | EXAMPLES OF MATERIAL | PUBLICATIONS |
|---|---|---|
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |

TABLE A-continued
| MATERIAL | EXAMPLES OF MATERIAL | PUBLICATIONS |
|---|---|---|
| Aza-carbazoles | 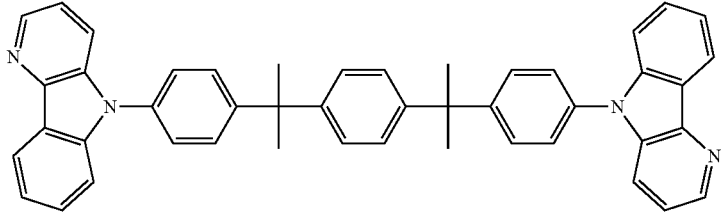 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials
| Anthracene-benzoimidazole compounds | 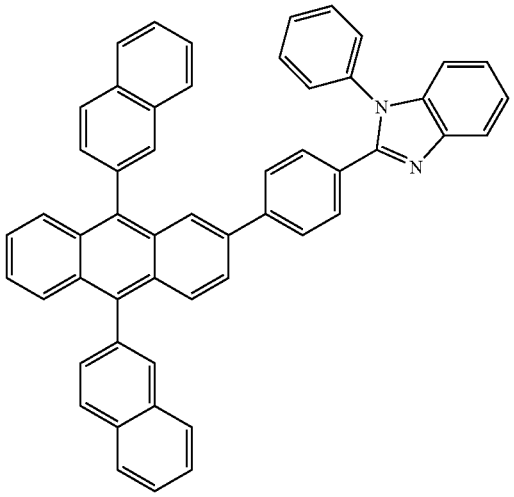 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 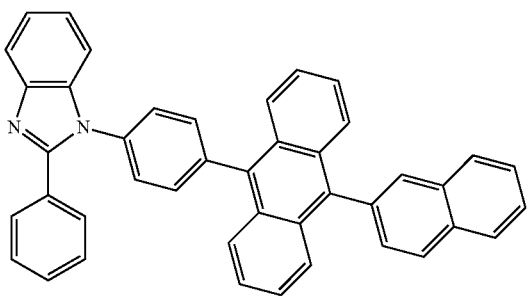 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 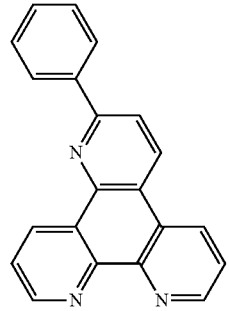 [SMILES: c1ccc(-c2ccc3c4cccnc4c4ncccc4c3n2)cc1] | US20090115316 |

TABLE A-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE A-continued
| MATERIAL | EXAMPLES OF MATERIAL | PUBLICATIONS |
|---|---|---|
| | 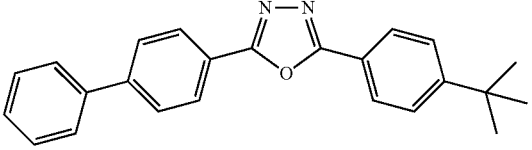 [SMILES: CC(C)(C)c1ccc(-c2nnc(-c3ccc(-c4ccccc4)cc3)o2)cc1] | Appl. Phys. Lett. 55, 1489 (1989) |
| | 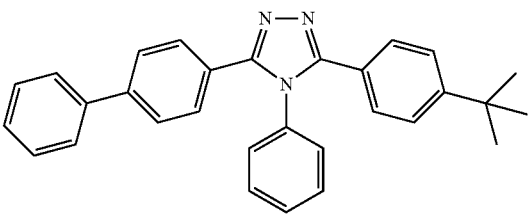 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 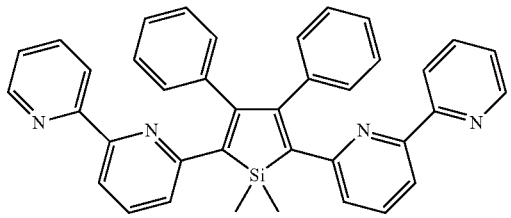 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 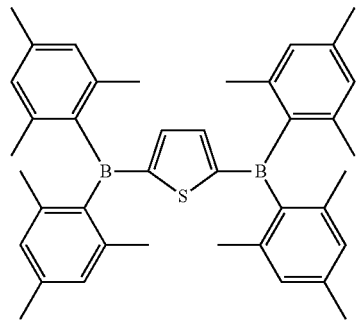 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 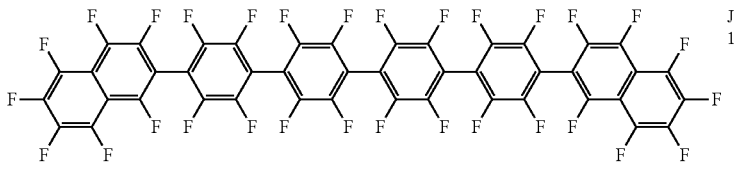 | J. Am. Chem. Soc. 122, 1832 (2000) |
| Fullerene (e.g., $C_{60}$) | 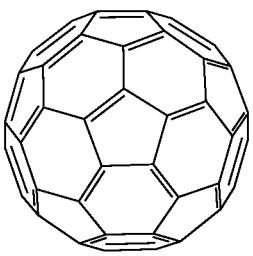 [SMILES: c1cc2c3ccc4c5ccc6c7ccc8c9ccc%10c1c1c2c2c3c4c3c5c6c4c7c8c5c9c%10c1c1c2c3c4c51] | US20090101870 |

TABLE A-continued

| MATERIAL | EXAMPLES OF MATERIAL | PUBLICATIONS |
|---|---|---|
| Triazine complexes | | US20040036077 |
| Zn (N^N)complexes | | U.S. Pat. No. 6,528,187 |

Synthesis of Compounds

Chemical abbreviations used throughout this document are as follows:

"SPhos" is dicyclohexyl(2',6'-dimethoxy-[1,1'-biphenyl]-2-yl)phosphine;

"Pd$_2$(dba)$_3$" is tris(dibenzylideneacetone) dipalladium(0);

"DCM" is dichloromethane;

"DME" is dimethyoxyethane; and

"THF" is tetrahydrofuran.

Synthesis of Compound C5

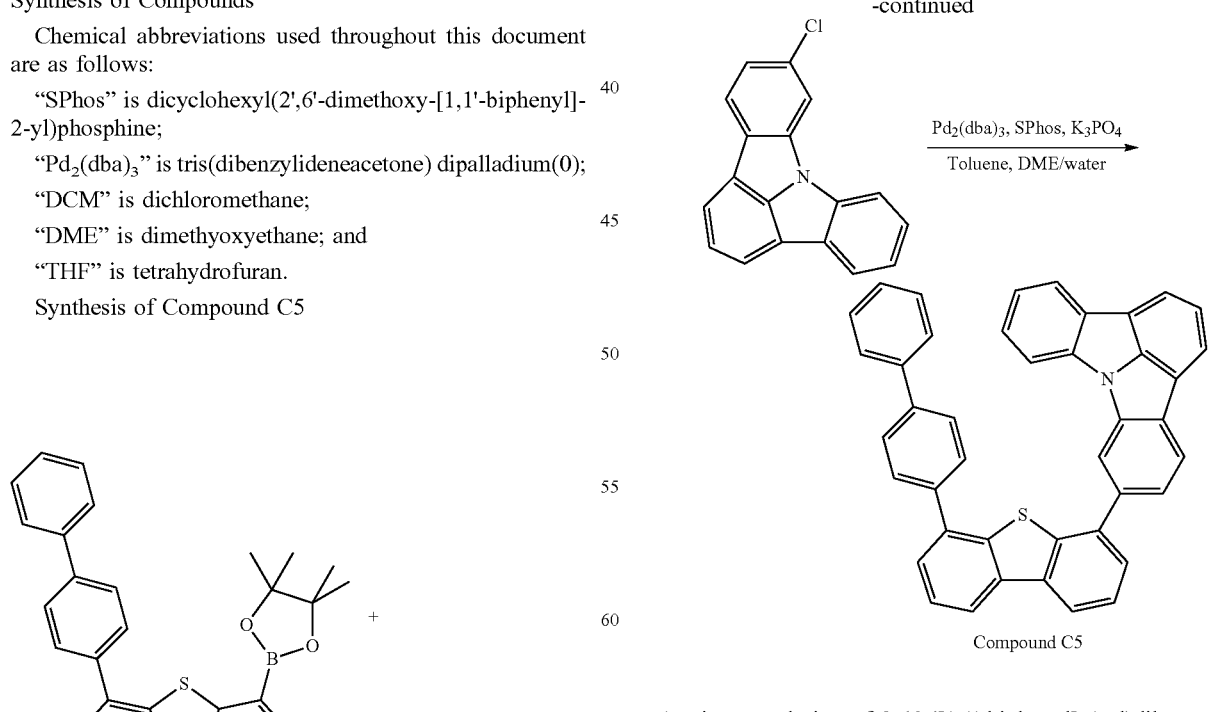

Compound C5

A mixture solution of 2-(6-([1,1'-biphenyl]-4-yl)dibenzo[b,d]thiophen-4-yl)-4,4,5,5-tetramethyl-1,3,2-dioxaborolane (4.75 g, 10.27 mmol), 6-chloroindolo[3,2,1-jk]carbazole (3.12 g, 11.30 mmol), Pd$_2$(dba)$_3$ (0.282 g, 0.308 mmol), SPhos (0.505 g, 1.233 mmol) and K₃PO₄ (7.09 g, 30.8 mmol) in DME (115 ml), toluene (130 ml) and water (30 ml) was refluxed under nitrogen for 36 hours. After cooling to room temperature, the solid was collected by filtration, dissolved in boiling xylene and filtered through a short plug of silica gel. Upon evaporation of the solvent, the crude product was recrystallized from xylene to yield Compound C5 (5.11 g, 86%) as a white solid.

Synthesis of Compound C8

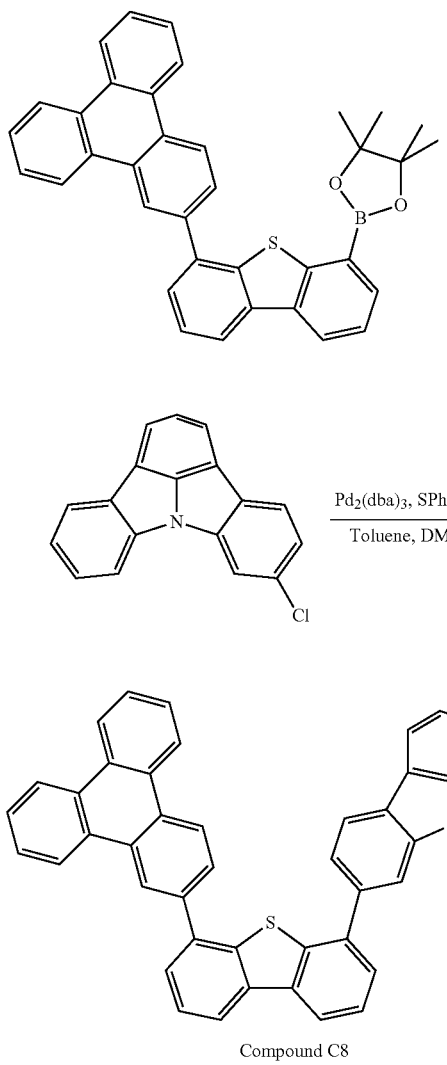

Compound C8

A solution of 4,4,5,5-tetramethyl-2-(6-(triphenylen-2-yl)dibenzo[b,d]thiophen-4-yl)-1,3,2-dioxaborolane (5 g, 9.32 mmol), 6-chloroindolo[3,2,1-jk]carbazole (2.96 g, 10.72 mmol), Pd₂(dba)₃ (0.213 g, 0.233 mmol), SPhos (0.382 g, 0.932 mmol), and K₃PO₄ (6.43 g, 28.0 mmol) in toluene (110 ml), DME (110 ml), and water (30 ml) was refluxed under nitrogen for 16 hours. The precipitation was isolated by filtration, triturated with o-xylene and methanol to yield Compound C8 (4.8 g, 80%) as a white solid.

Synthesis of Compound C11

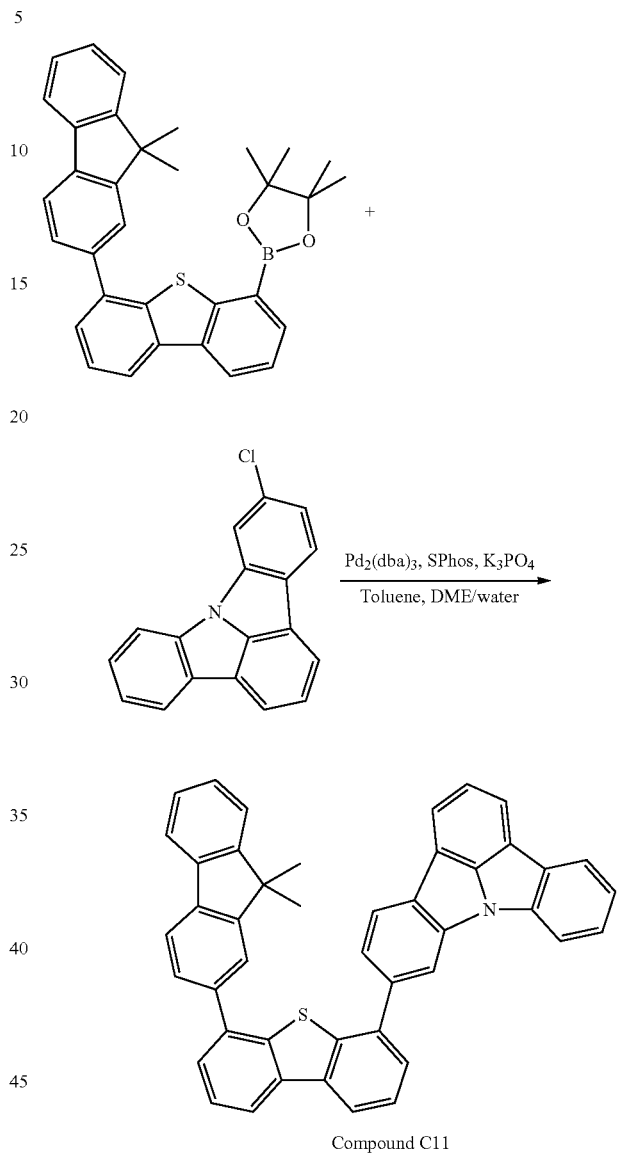

Compound C11

A mixture solution of 2-(6-(9,9-dimethyl-9H-fluoren-2-yl)dibenzo[b,d]thiophen-4-yl)-4,4,5,5-tetramethyl-1,3,2-dioxaborolane (3.5 g, 6.97 mmol), 6-chloroindolo[3,2,1-jk]carbazole (2.113 g, 7.66 mmol), Pd₂(dba)₃ (0.128 g, 0.139 mmol), SPhos (0.229 g, 0.557 mmol) and potassium phosphate (4.44 g, 20.90 mmol) in DME (42 ml), toluene (14 ml) and water (14 ml) was refluxed under nitrogen for 16 hours. After cooling to room temperature, the reaction mixture was diluted with with water. The organic layer was isolated, washed with brine and dried over Na₂SO₄. Upon evaporation of the solvent, the residue was triturated with ethanol. The solid was collected by filtration, dissolved in hot toluene, filtered through a short plug of silica gel. Upon evaporation off solvent, the crude product recrystallized from toluene to yield Compound C11 (3.6 g, 84%) as a white solid.

Synthesis of Compound D3

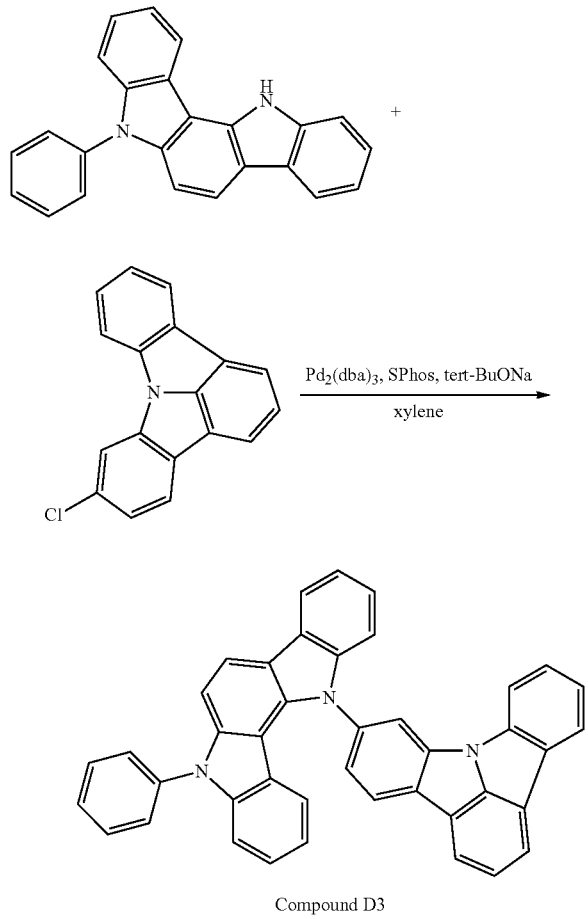

Compound D3

A solution of 5-phenyl-5,12-dihydroindolo[3,2-a]carbazole (2.77 g, 8.34 mmol), 6-chloroindolo[3,2,1-jk]carbazole (2.3 g, 8.34 mmol), Pd$_2$(dba)$_3$ (0.153 g, 0.167 mmol), SPhos (0.137 g, 0.334 mmol) and tert-BuONa (2.004 g, 20.85 mmol) in xylene (83 ml) was refluxed under nitrogen for 24 hours. After cooling to room temperature, the solid was removed by filtration, and the solvent was evaporated. The residue was purified by column chromatography on silica gel with heptane/DCM (9/1, v/v) as eluent, and recrystallized from toluene to yield Compound D3 (1.9 g, 40%) as a white solid.

Synthesis of Compound D11

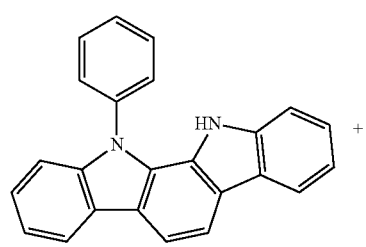

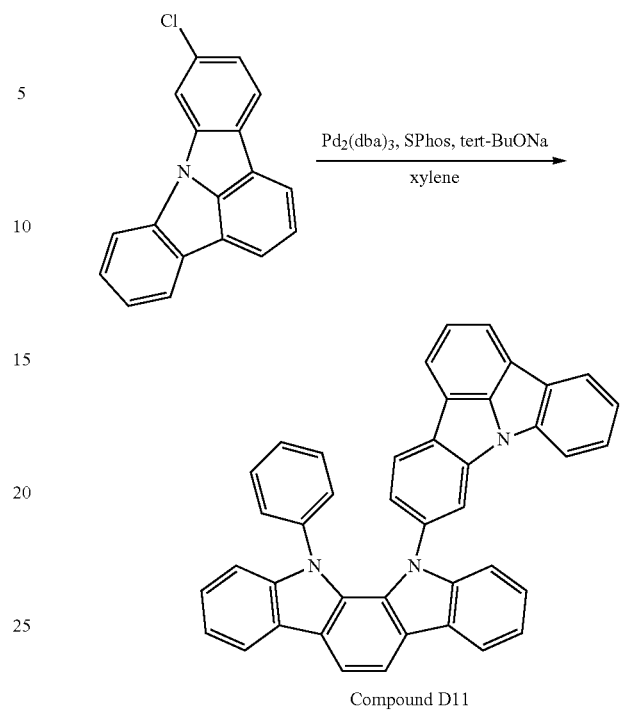

Compound D11

A solution of 11-phenyl-11,12-dihydroindolo[2,3-a]carbazole (4 g, 12.03 mmol), 10-chloroindolo[3,2,1-jk]carbazole (3.98 g, 14.44 mmol), Pd$_2$(dba)$_3$ (0.363 g, 0.397 mmol), SPhos (0.8 g, 1.951 mmol) and tert-BuONa (2.31 g, 24.07 mmol) in xylene (250 ml) was refluxed under nitrogen for 48 hours. The reaction mixture was cooled to room temperature, filtered through a short plug of Celite. Upon evaporation off the solvent, the residue was purified by column chromatography on silica gel with heptane/toluene (7/3 to 1/1, v/v) as eluent, followed by chromatography on silica gel with heptane/THF (85/15 to 65/35, v/v) as eluent to yield Compound D11 (3.88 g, 56%) as a white solid.

Synthesis of Compound D17

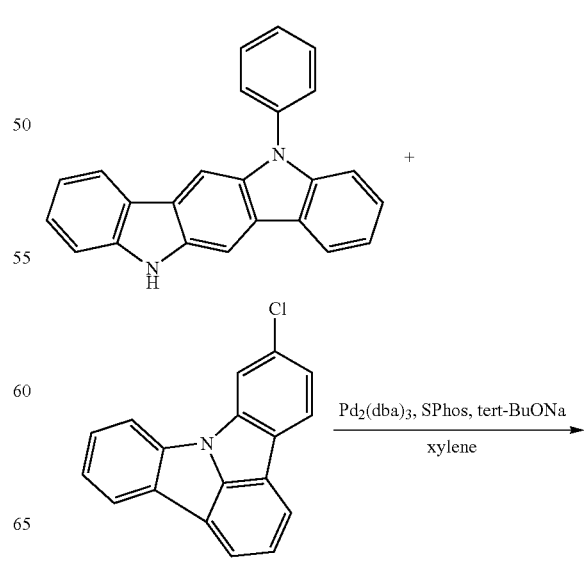

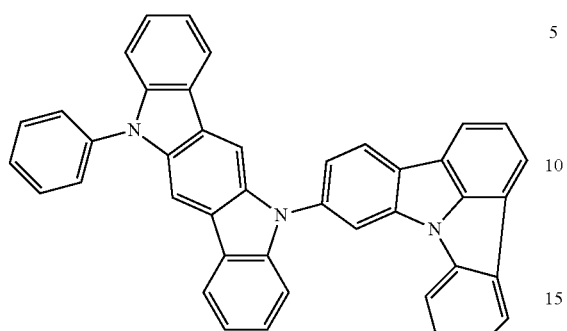

Compound D17

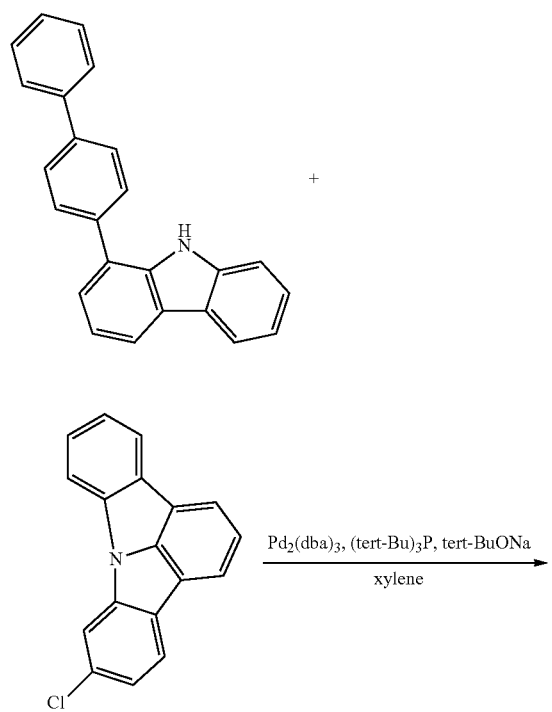

Compound F1

A solution of 6-chloroindolo[3,2,1-jk]carbazole (1.742 g 6.32 mmol), 5-phenyl-5,11-dihydroindolo[3,2-b]carbazole (2.1 g, 6.32 mmol) $Pd_2(dba)_3$ (0.116 g, 0.126 mmol), SPhos (0.104 g, 0.253 mmol) and tert-BuONa (1.821 g, 18.95 mmol) in xylene (100 ml) was refluxed overnight. The hot reactions solution was diluted with toluene, filtered through a short plug of silica gel. Upon evaporation off the solvent, the residue was purified by successive recrystallizations from ethyl acetate and xylene to yield Compound D17 (1.8 g, 50%) as a yellowish solid.

Synthesis of Compound F1

Into a degased solution of 1-([1,1'-biphenyl]-4-yl)-9H-carbazole (3 g, 9.39 mmol) and 6-chloroindolo[3,2,1-jk] carbazole (2.59 g, 9.39 mmol) in xylene (100 ml) was added tri-tert-butylphosphane (0.939 ml, 0.939 mmol), $Pd_2(dba)_3$ (0.172 g, 0.188 mmol) and tert-BuONa (1.81 g, 18.78 mmol). The reaction mixture was refluxed under nitrogen for 5 hours. After cooling to room temperature, the solid was collected by filtration, dissolved in boiling toluene and filtered through a short plug of silica gel. Upon evaporation off the solvent, the crude product was recrystallized from toluene to yield Compound F1 (4.0 g, 76%) as a white solid.

Experimental

Application in OLED.

All devices were fabricated by high vacuum (~$10^{-7}$ Torr) thermal evaporation. The anode electrode was 80 nm of indium tin oxide (ITO). The cathode electrode consisted of 1 nm of LiQ followed by 100 nm of Al. All devices were encapsulated with a glass lid sealed with an epoxy resin in a nitrogen glove box (<1 ppm of $H_2O$ and $O_2$) immediately after fabrication, and a moisture getter was incorporated inside the package.

Device Examples—Set 1

A first set of device examples have organic stacks consisting of, sequentially from the ITO surface, 10 nm of LG101 (from LG Chem) as the hole injection layer (HIL), 45 nm of PPh-TPD as the hole-transport layer (HTL), 40 nm of emissive layer (EML), followed by 30 nm of aDBT-ADN with LiQ as the electron-transport layer (ETL). The EML has two components, 90 wt % of the EML being the inventive compounds (Compound C5, C8, or C11) or comparative compound (CC-1) as the host and 10 wt % of the EML being Compound GD as the emitter. The structures of the compounds used are shown below.

PPh-TPD
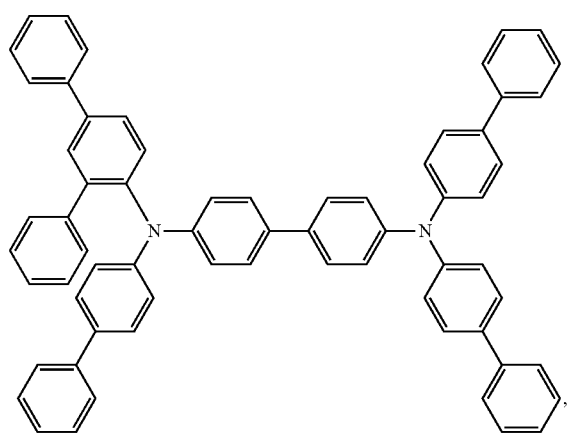
GD
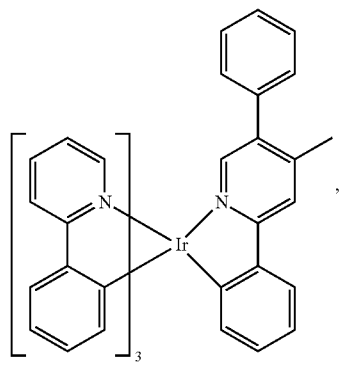
aDBT-ADN
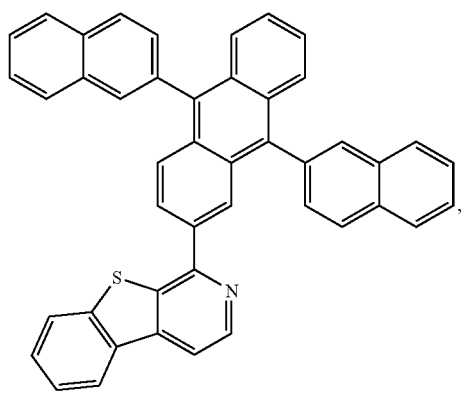
LiQ
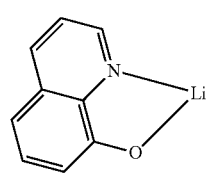
Compound C5
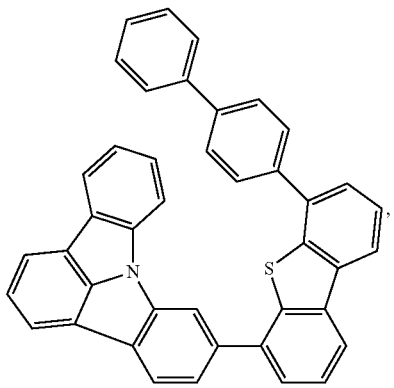
Compound C8, Compound C11, CC-1
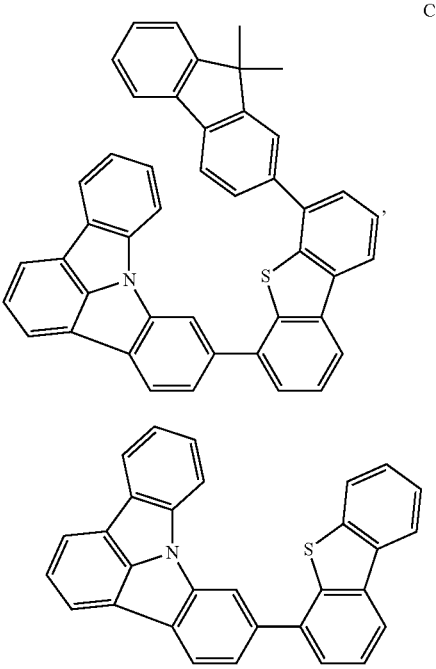
Provided in Table D1 below is a summary of the device data for device examples Set 1. The emission color, voltage (V), external quantum efficiency (EQE), and power efficiency (PE), recorded at 9000 nits, for the devices are presented.

TABLE D1

| | EML | | Emission | V | EQE | PE |
|---|---|---|---|---|---|---|
| Device ID | Host | Dopant | Color | [V] | [%] | [lm/W] |
| 1 | Compound C5 | GD | Green | 5.8 | 17.6 | 34.7 |
| 2 | Compound C8 | GD | Green | 5.9 | 19.8 | 38.3 |
| 3 | Compound C11 | GD | Green | 6.7 | 15.1 | 25.6 |
| DC-1 | CC-1 | GD | Green | 7.3 | 14.6 | 22.7 |

Device Examples—Set 2

A second set of device examples have the same device structure as that of Device Examples—Set 1, except that the EMLs in the second set of device examples have three components: 50 wt % of the EML being the invented compounds (Compound D3 or Compound F1) or comparative compound (CC-2) as the first host; 40 wt % of the EML being Compound EH-1 as the second host; and 10 wt % of the EML being Compound GD as the the emitter. The structures of Compound D3, Compound F1, EH-1 and CC-2 are shown below.

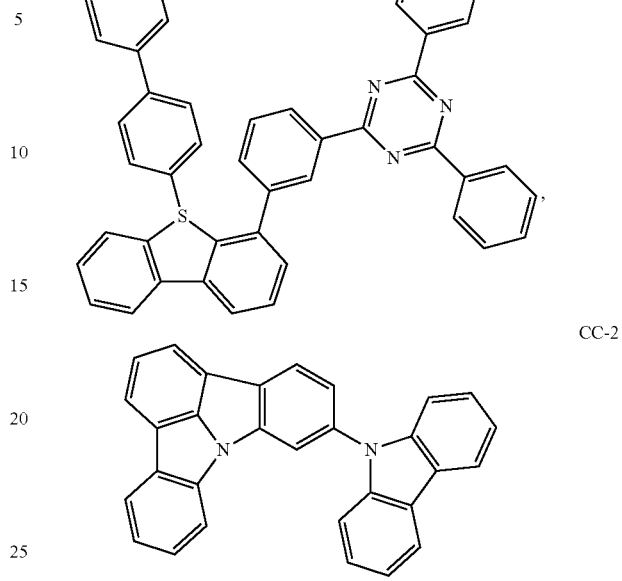

EH-1

CC-2

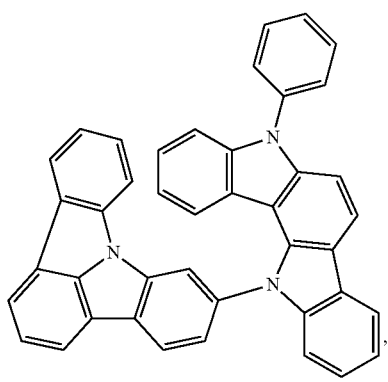

Compound D3

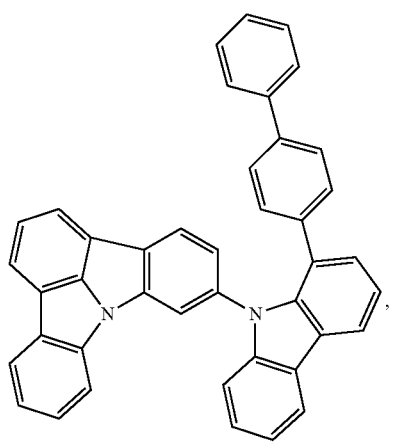

Compound F1

Provided in Table D2 below is a summary of the device data for device examples Set 2. Emission color, voltage (V), external quantum efficiency (EQE), and power efficiency (PE), recorded at 9000 nits, for the devices are presented.

TABLE D2

| | EML | | | | | | |
|---|---|---|---|---|---|---|---|
| Device ID | First Host | Second host | Dopant | Emission Color | V [V] | EQE [%] | PE [lm/W] |
| 4 | Compound D3 | EH-1 | GD | Green | 5.7 | 18.0 | 36.1 |
| 5 | Compound F1 | EH-1 | GD | Green | 5.7 | 15.7 | 31.6 |
| DC-2 | CC-2 | EH-1 | GD | Green | 6.6 | 13.8 | 23.7 |

The data in Table D1 and Table D2 show that the devices using the inventive compounds as the hosts require lower driving voltage while achieving higher efficiency than the devices using the comparative compounds as the host. The improved device performance of the inventive compounds was unexpected but the inventors believe that the improvements are attributable to their unique chemical structure. For example, the additional building blocks, biphenyl, triphenylene and fluorene, in the inventive Compounds C5, C8 and C11, respectively, extend the aromatic system and might have enhanced the charge transport capability of these compounds. The same argument also holds for Compounds D3 and F1.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having a formula:

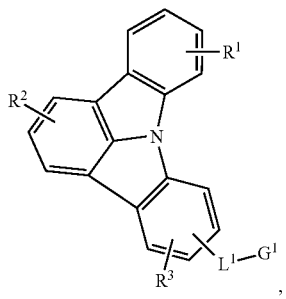

Formula I;
wherein $L^1$ is selected from the group consisting of a direct bond, phenyl, biphenyl, terphenyl, fluorene, carbazole, pyridine, pyrimidine, pyrazine, pyridazine, triazine, naphthalene, anthracene, and combinations thereof;
wherein $G^1$ is selected from the group consisting of:

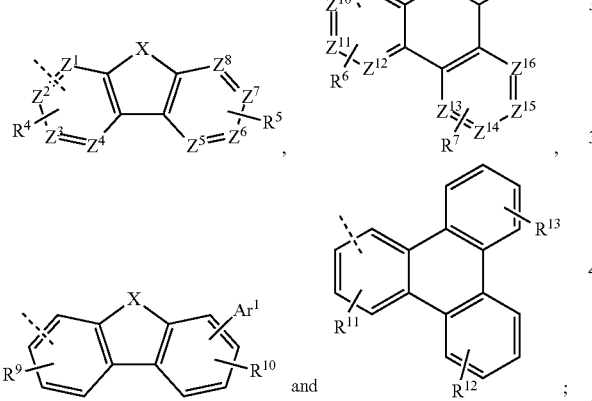

wherein X is selected from the group consisting of oxygen, sulfur, and selenium;
wherein $R^1$, $R^5$, $R^7$, $R^8$, $R^{12}$, and $R^{13}$ each independently represent mono, di, tri, or tetra substitution, or no substitution;
wherein $R^2$, $R^3$, $R^4$, $R^5$, $R^6$, $R^9$, $R^{10}$, and $R^{11}$ each independently represent mono, di, or tri substitution, or no substitution;
wherein $R^1$ to $R^{13}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;
wherein $Z^1$ to $Z^{20}$ are each independently selected from the group consisting of carbon and nitrogen;
wherein at least one of $Z^1$, $Z^2$, $Z^3$, $Z^4$, $Z^5$, $Z^6$, $Z^7$, and $Z^8$ is nitrogen; and at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen;
wherein when any of $Z^1$ to $Z^{20}$ is nitrogen, there is no substitution on that nitrogen;
wherein $L^1$ and $G^1$ are bonded together by a C—C bond;
wherein $Ar^1$ is selected from the group consisting of benzene, biphenyl, terphenyl, triphenylene, fluorene, dibenzofuran, dibenzothiophene, dibenzoselenophene, naphthalene, phenanthrene, carbazole, pyridine, pyrimidine, pyrazine, pyridazine, triazine, azatriphenylene, aza-fluorene, aza-dibenzofuran, aza-dibenzothiophene, aza-dibenzoselenophene, aza-carbazole, quinolone, quinazoline, and combinations thereof;
wherein $L^1$ and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, carbazole, pyridine, pyrimidine, pyrazine, pyridazine, triazine, quinolone, phenanthroline, aza-dibenzofuran, aza-dibenzothiophene, aza-dibenzoselenophene, aza-fluorene and aza-triphenylene, aza-carbazole, and combinations thereof; and
wherein the compound of Formula I contains at most one non-fused carbazole moiety.

2. The compound of claim 1, wherein $G^1$ is selected from the group consisting of:

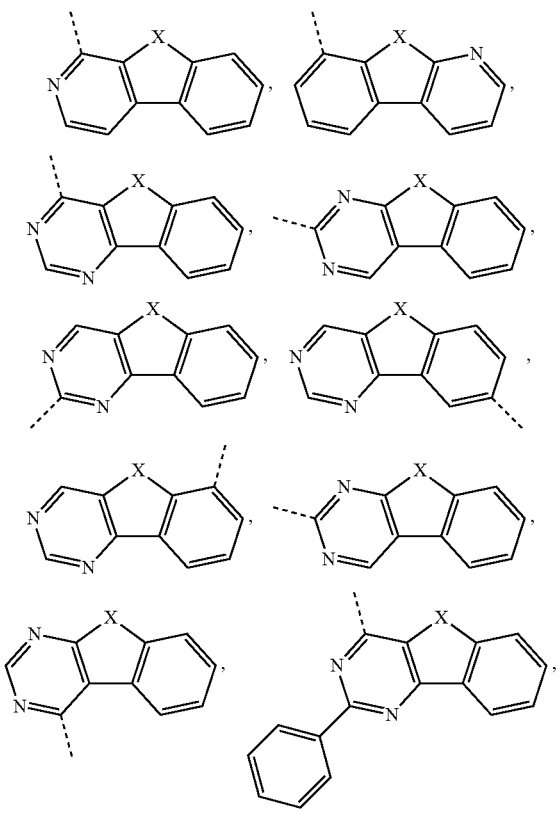

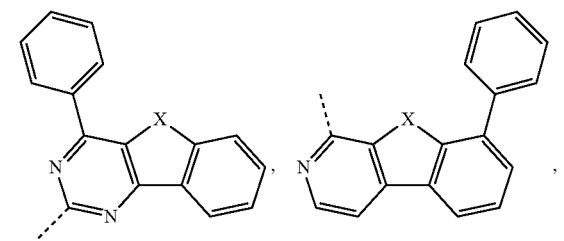
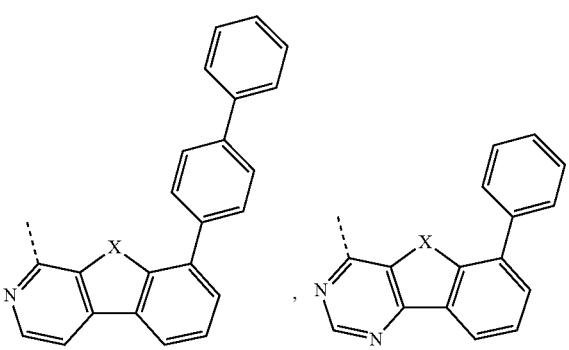
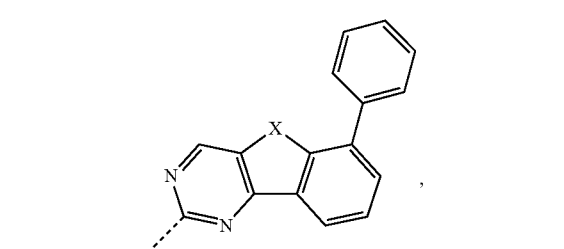
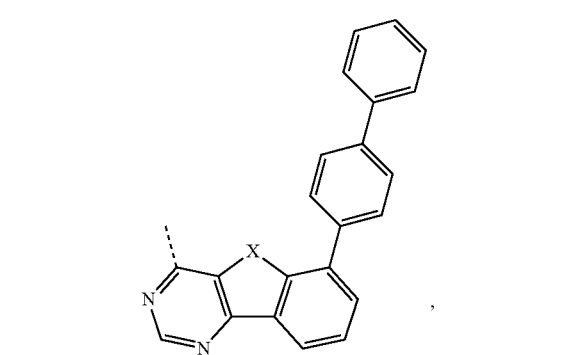
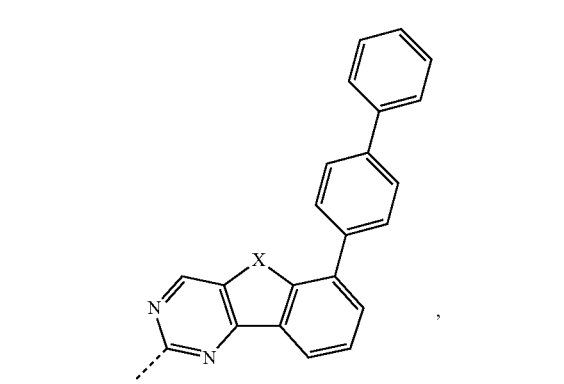
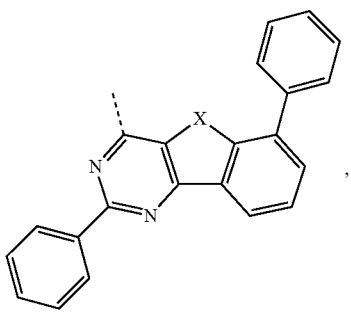
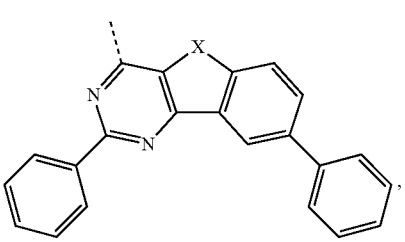
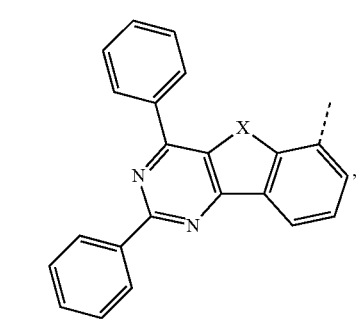
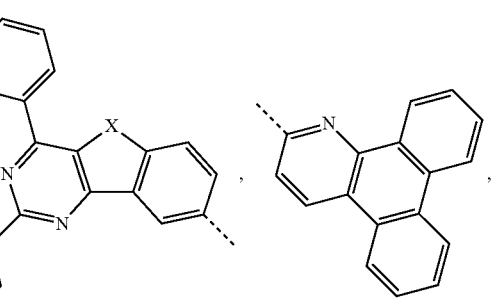
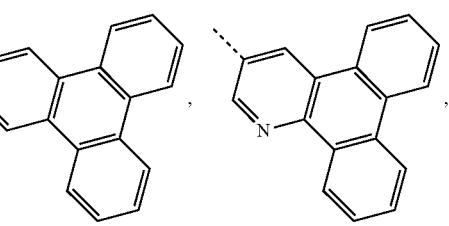
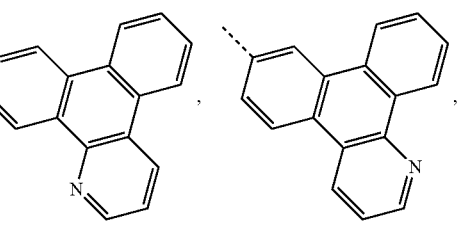

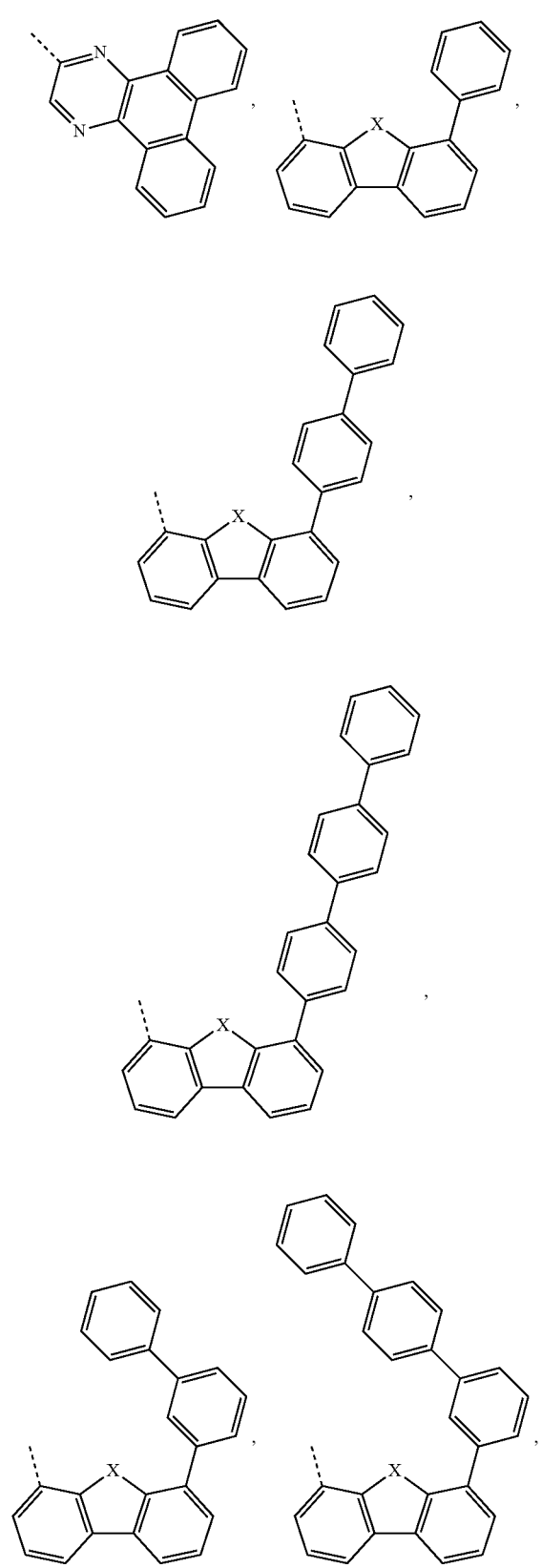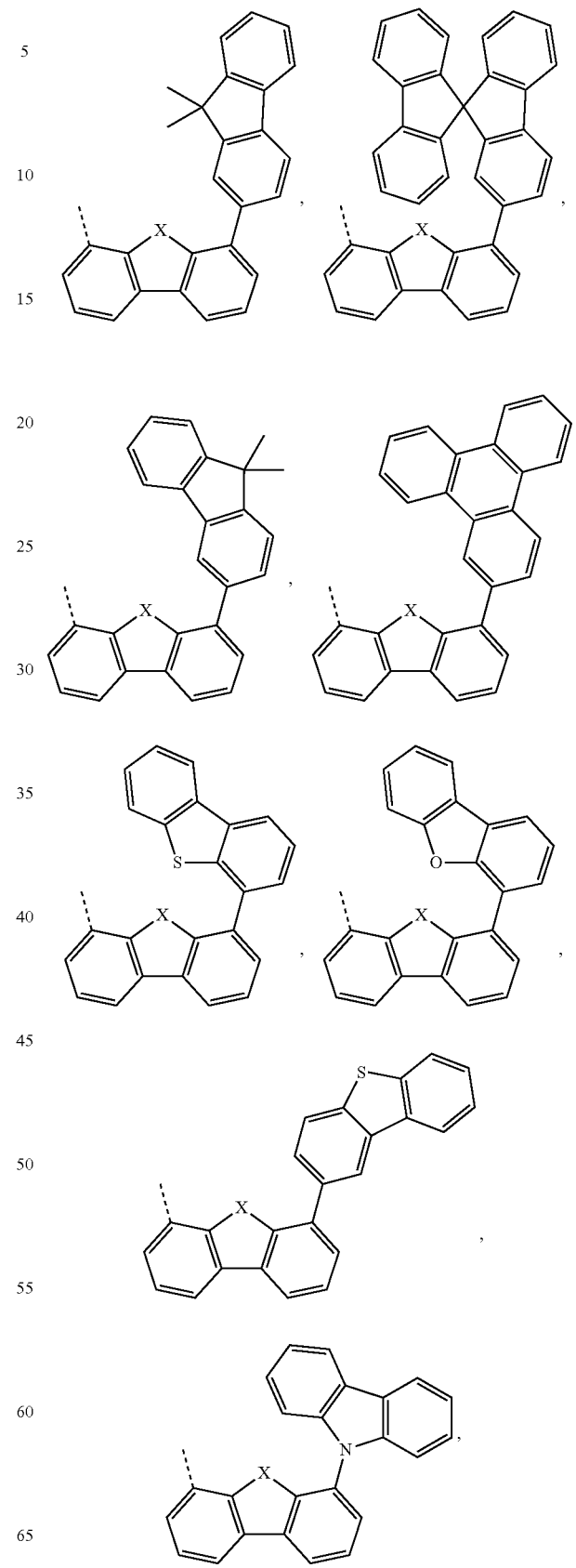

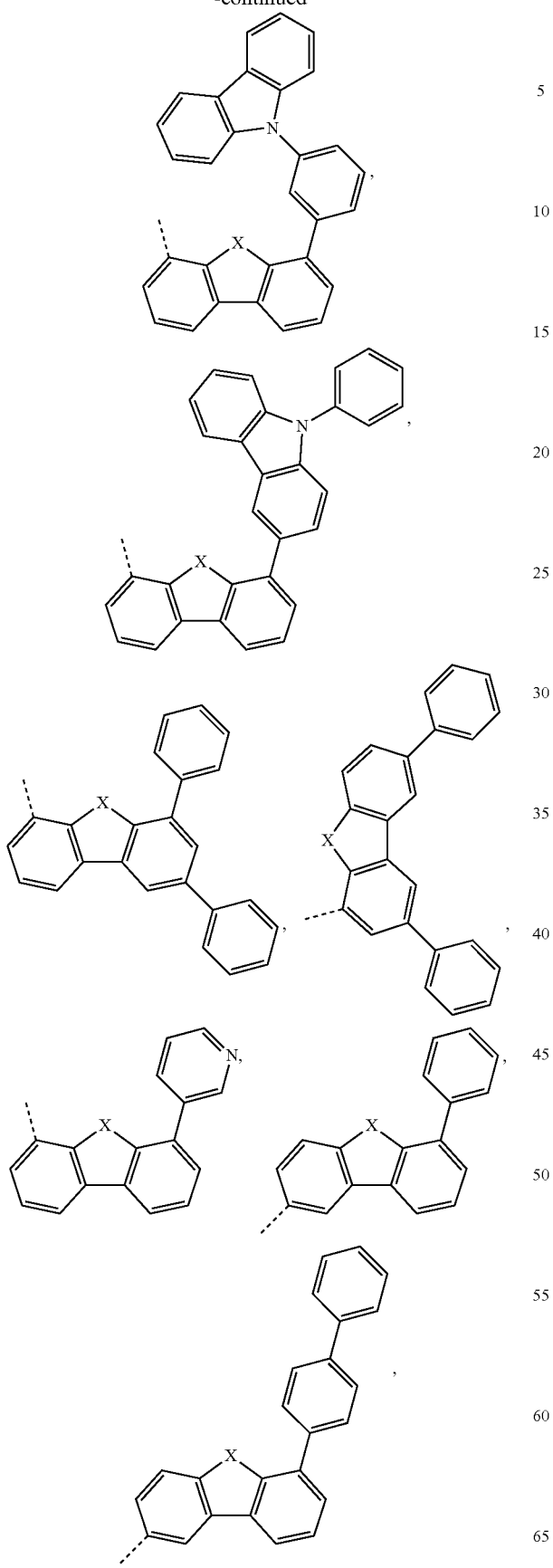
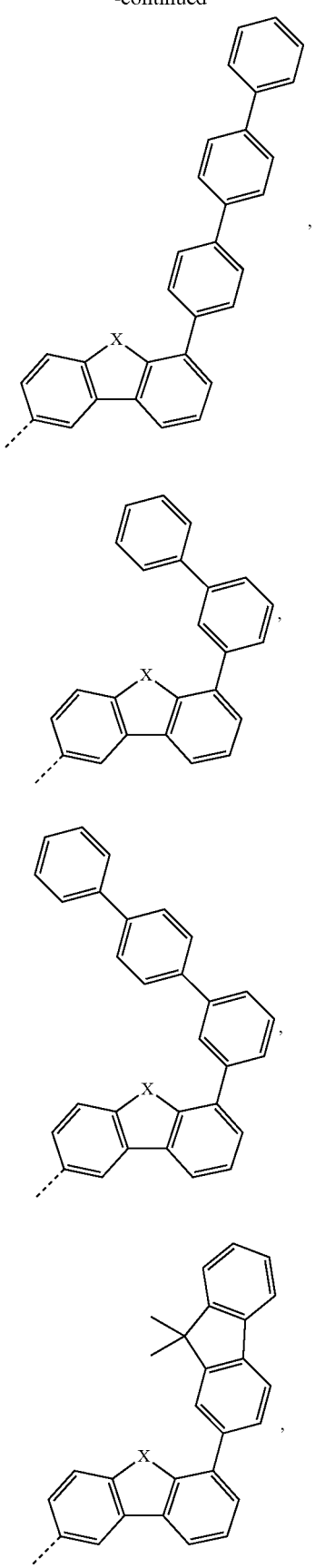

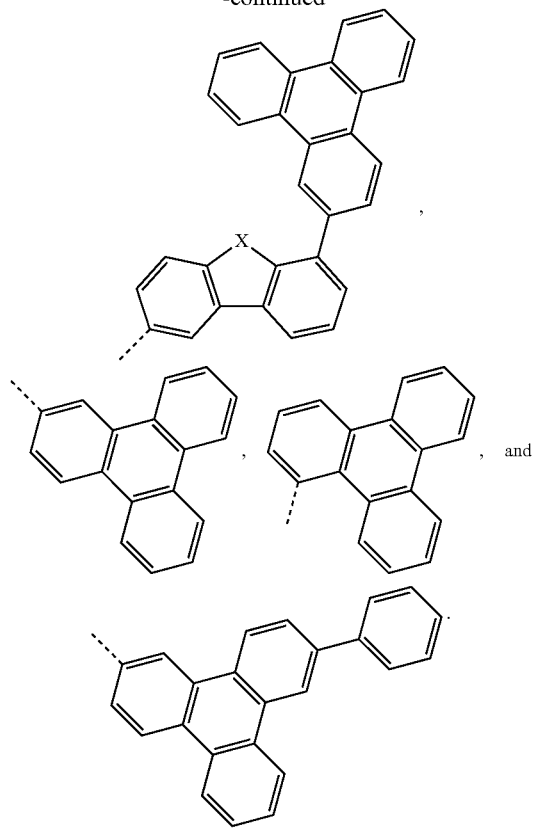
3. The compound of claim 1, wherein the compound is selected from the group consisting of:
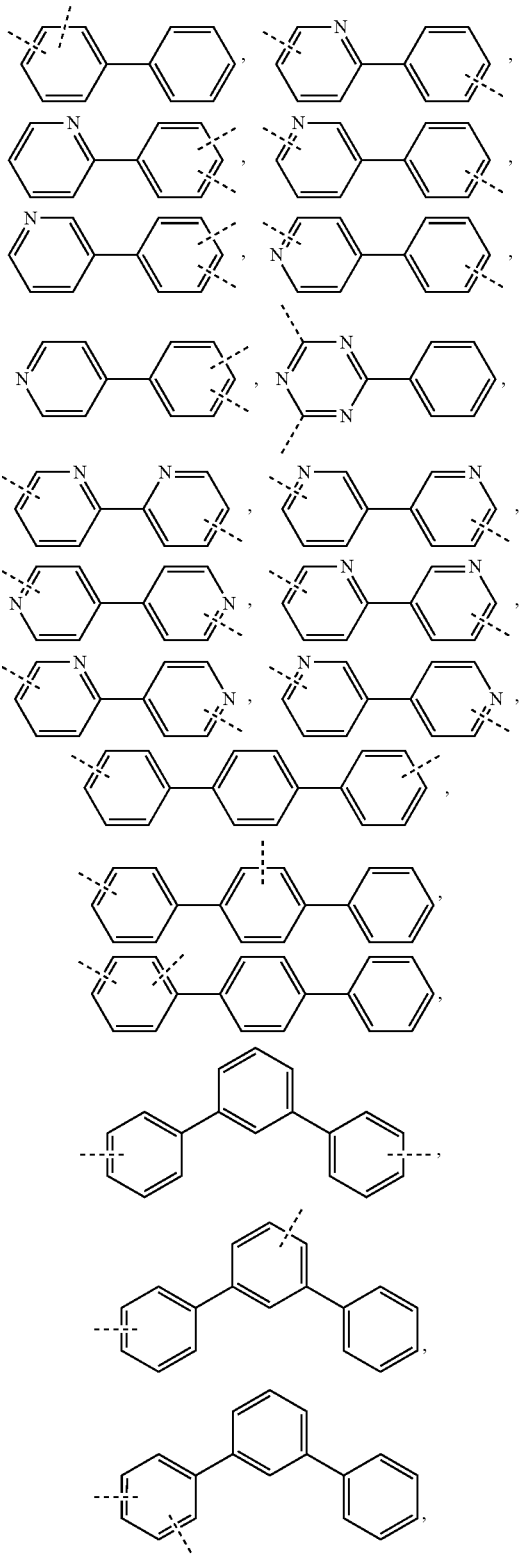
4. The compound of claim 1, wherein $L^1$ is selected from the group consisting of:
a direct bond,
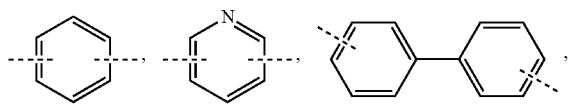

-continued

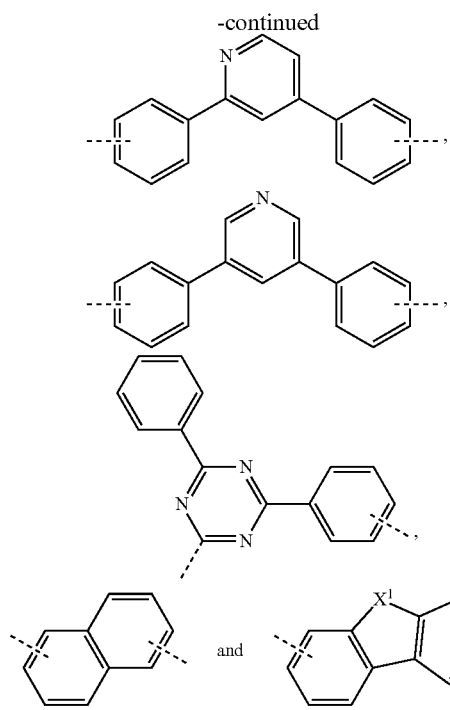

wherein $X^1$ is selected from a group consisting of O, S, Se, $CR^{L1}R^{L2}$, and $NR^{L3}$;

wherein $R^{L1}$, $R^{L2}$, and $R^{L3}$ are each independently selected from the group consisting of hydrogen, deuterium, alkyl, aryl, and combinations thereof.

5. The compound of claim 1, wherein the compound is selected from the group consisting of:

Compounds A1, A2, and A3 each represented by the formula

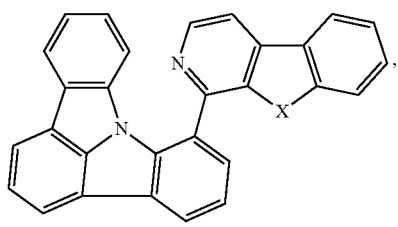

wherein in Compound A1, X = O,
in Compound A2, X = S, and
in Compound A3, X = Se Compounds A4, A5, and A6 each represented by the formula

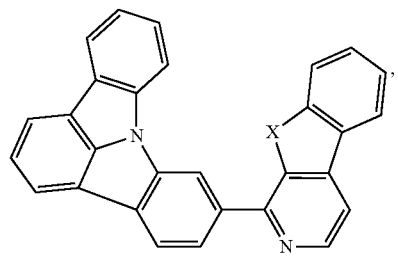

wherein in Compound A4, X = O,
in Compound A5, X = S, and
in Compound A6, X = Se Compounds A7, A8, and A9 each represented by the formula

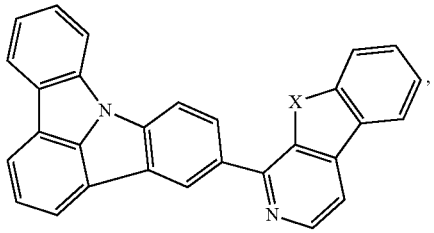

wherein in Compound A7, X = O,
in Compound A8, X = S, and
in Compound A9, X = Se Compounds A10, A11, and A12 each represented by the formula

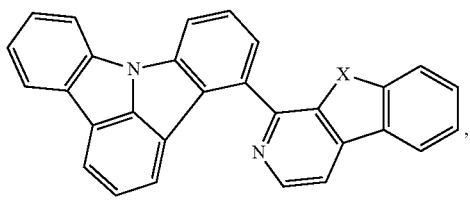

wherein in Compound A10, X = O,
in Compound A11, X = S, and
in Compound A12, X = Se Compounds A13, A14, and A15 each represented by the formula

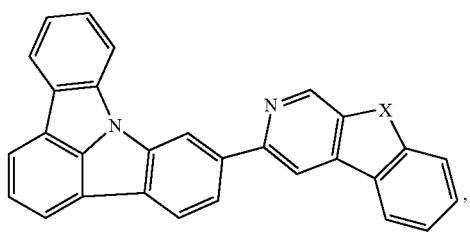

wherein in Compound A13, X = O,
in Compound A14, X = S, and
in Compound A15, X = Se Compounds A16, A17, and A18 each represented by the formula

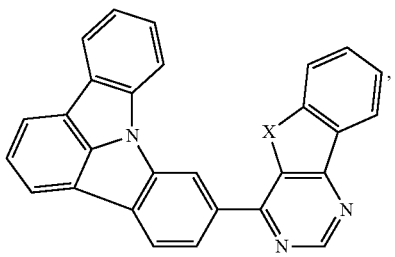

wherein in Compound A16, X = O,
in Compound A17, X = S, and
in Compound A18, X = Se -continued Compounds A19, A20, and A21 each represented by the formula

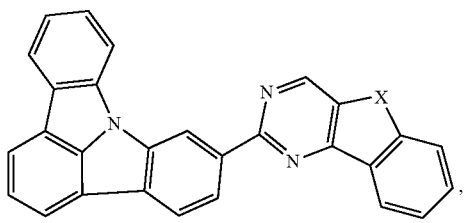

wherein in Compound A19, X = O,
in Compound A20, X = S, and
in Compound A21, X = Se Compounds A22, A23, and A24 each represented by the formula

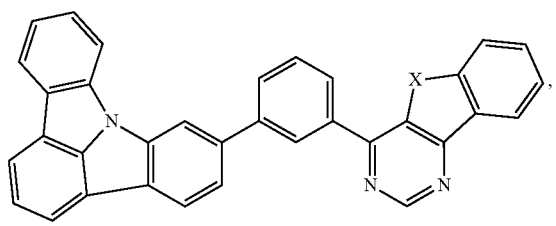

wherein in Compound A22, X = O,
in Compound A23, X = S, and
in Compound A24, X = Se Compounds A25, A26, and A27 each represented by the formula

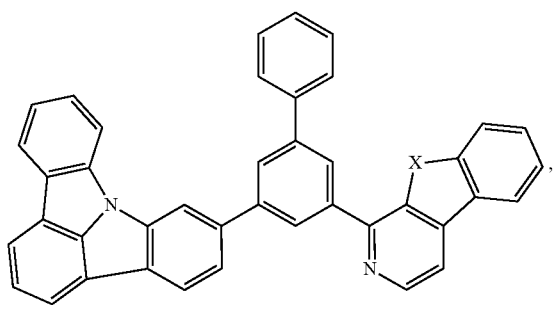

wherein in Compound A25, X = O,
in Compound A26, X = S, and
in Compound A27, X = Se Compounds A28, A29, and A30 each represented by the formula

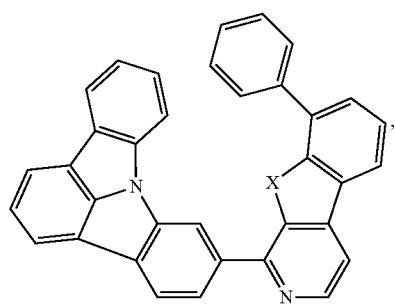

wherein in Compound A28, X = O,
in Compound A29, X = S, and
in Compound A30, X = Se -continued Compounds A31, A32, and A33 each represented by the formula

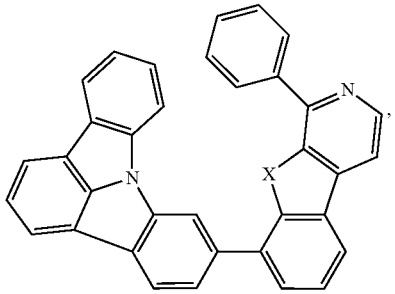

wherein in Compound A31, X = O,
in Compound A32, X = S, and
in Compound A33, X = Se Compounds A34, A35, and A36 each represented by the formula

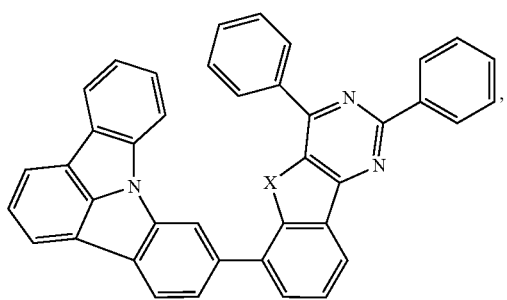

wherein in Compound A34, X = O,
in Compound A35, X = S, and
in Compound A36, X = Se Compound B1

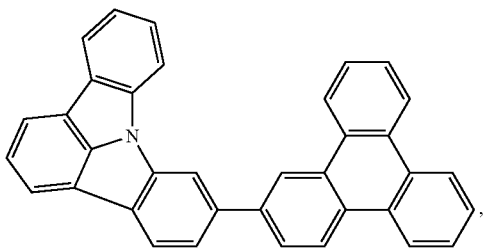

Compound B2

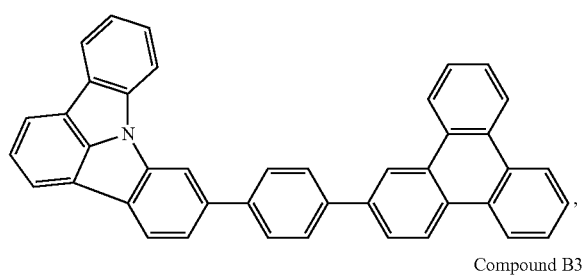

Compound B3

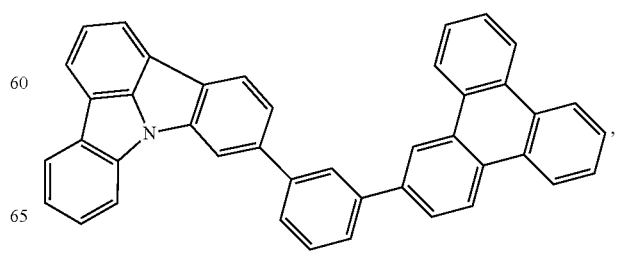

-continued
Compound B4
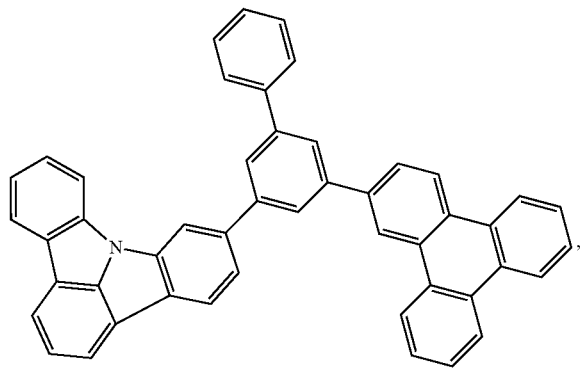
Compound B5
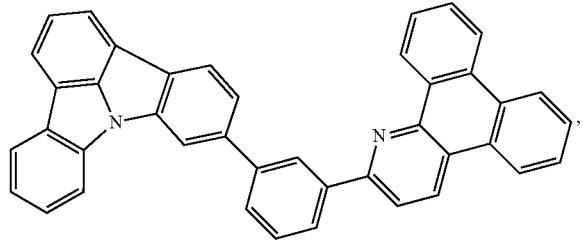
Compound B6
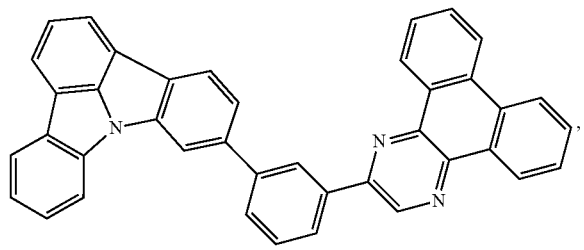
Compound B7
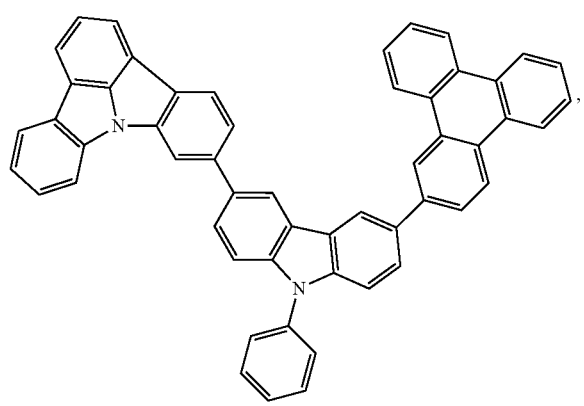
-continued
Compound B8
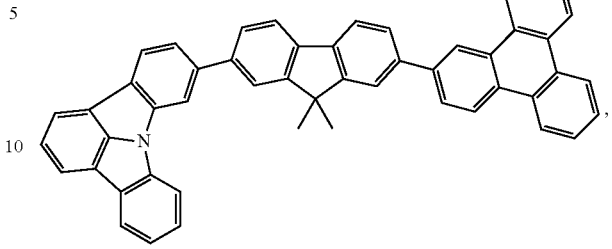
Compound B9
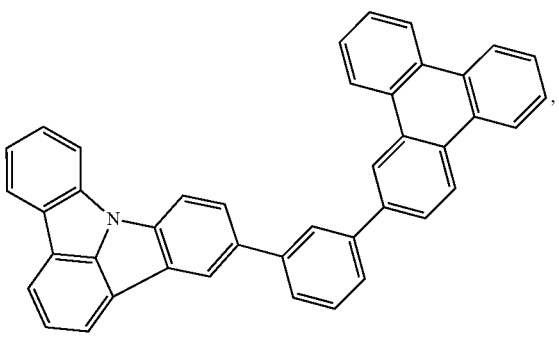
Compounds C1, C2, and C3 each represented by the formula
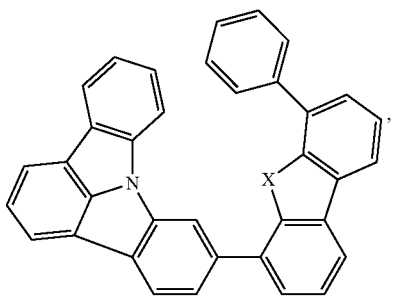
wherein in Compound C1, X = O,
in Compound C2, X = S, and
in Compound C3, X = Se
Compounds C4, C5, and C6 each represented by the formula
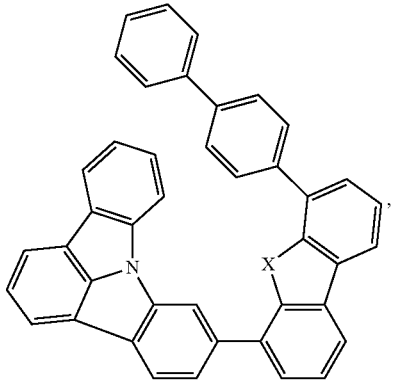
wherein in Compound C4, X = O,
in Compound C5, X = S, and
in Compound C6, X = Se Compounds C7, C8, and C9 each represented by the formula

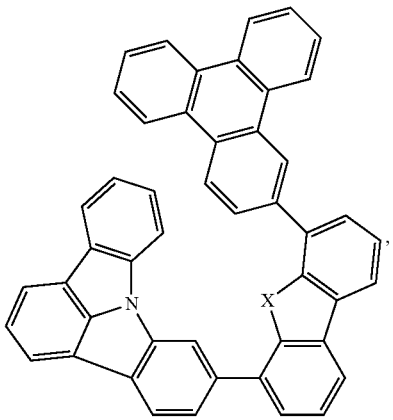

wherein in Compound C7, X = O,
in Compound C8, X = S, and
in Compound C9, X = Se Compounds C10, C11, and C12 each represented by the formula

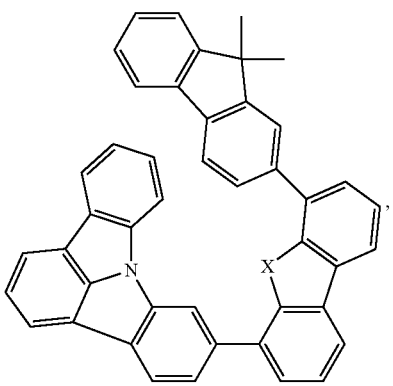

wherein in Compound C10, X = O,
in Compound C11, X = S, and
in Compound C12, X = Se Compounds C13, C14, and C15 each represented by the formula

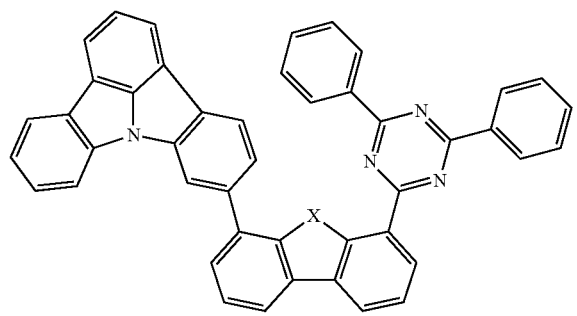

wherein in Compound C13, X = O,
in Compound C14, X = S, and
in Compound C15, X = Se Compounds C16, C17, and C18 each represented by the formula

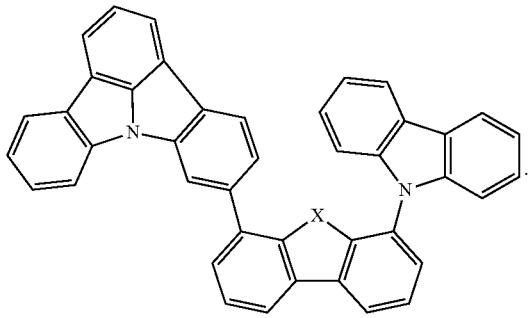

wherein in Compound C16, X = O,
in Compound C17, X = S, and
in Compound C18, X = Se Compounds C19, C20, and C21 each represented by the formula

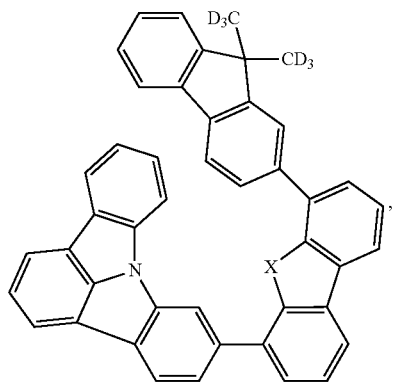

wherein in Compound C19, X = O,
in Compound C20, X = S, and
in Compound C21, X = Se Compounds C22, C23, and C24 each represented by the formula

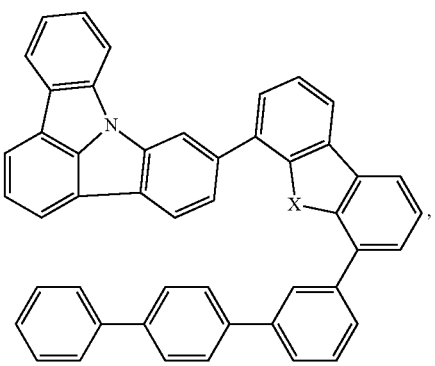

wherein in Compound C22, X = O,
in Compound C23, X = S, and
in Compound C24, X = Se -continued Compounds C25, C26, and C27 each represented by the formula

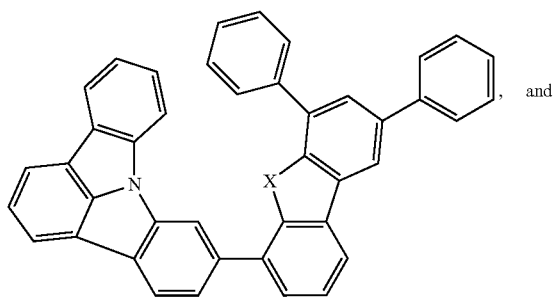

wherein in Compound C25, X = O,
in Compound C26, X = S, and
in Compound C27, X = Se Compounds C28, C29, and C30 each represented by the formula

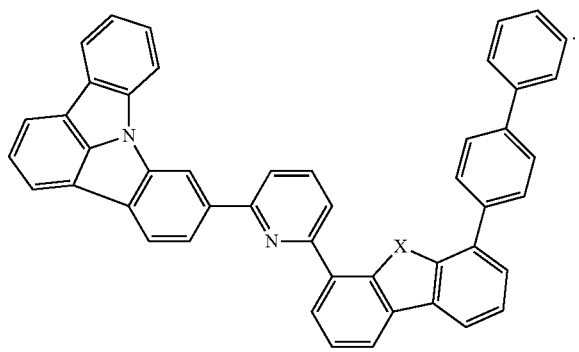

wherein in Compound C28, X = O,
in Compound C29, X = S, and
in Compound C30, X = Se 6. A compound having a formula,

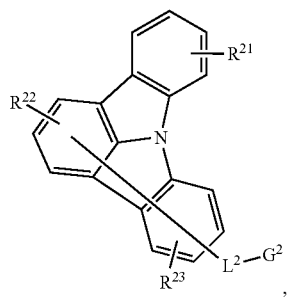

Formula II;
wherein $L^2$ is selected from the group consisting of a direct bond, alkyl, alkoxyl, aryl, heteroaryl, and combinations thereof;
wherein $R^{21}$ represents mono, di, tri, or tetra substitution, or no substitution;
wherein $R^{22}$, and $R^{23}$ each independently represent mono, di, or tri substitution, or no substitution;
wherein $R^{21}$ to $R^{23}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;
wherein $G^2$ is selected from the group consisting of:

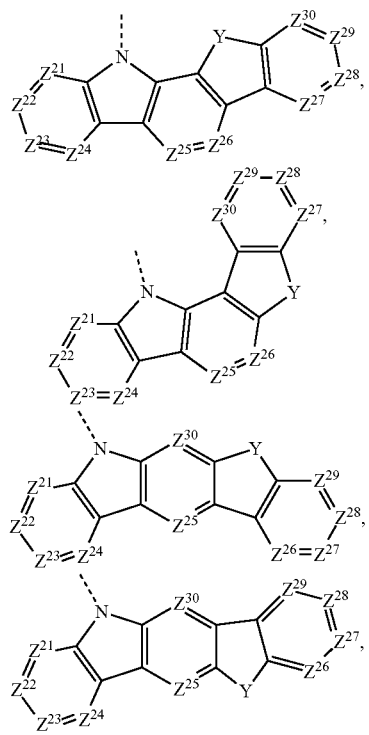

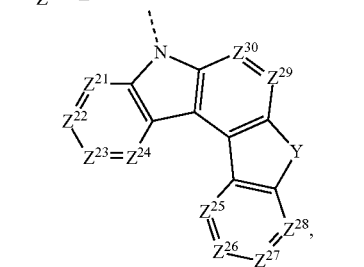

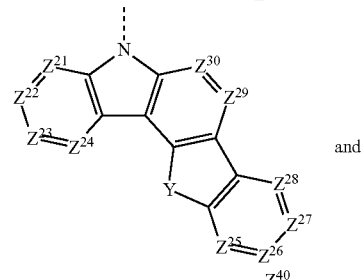

and

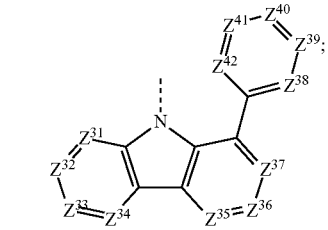

wherein $Z^{21}$ to $Z^{42}$ are each independently selected from the group consisting of $C-R^{20}$ and N;

wherein at least one of $Z^{21}$ to $Z^{42}$ is C—$R^{20}$;

wherein each $R^{20}$ can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any adjacent substituents are optionally joined to form a ring;

wherein Y is selected from the group consisting of: O, S, Se, $BR^{B1}$, $NR^{B2}$, $PR^{B3}$, and $CR^{B4}R^{B5}$;

wherein $R^{B1}$, $R^{B2}$, $R^{B3}$, $R^{B4}$ and $R^{B5}$ are each independently selected from the group consisting of hydrogen, deuterium, alkyl, cycloalkyl, heteroalkyl, arylalkyl, alkoxy, aryloxy, silyl, alkenyl, cycloalkenyl, heteroalkenyl, alkynyl, aryl, heteroaryl, and combinations thereof;

wherein $R^{B4}$ and $R^{B5}$ are optionally jointed to form a ring;

wherein $L^2$ is optionally further substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; and wherein the compound of Formula II contains at most one non-fused carbazole moiety.

7. The compound of claim 6, wherein the compound is selected from the group consisting of:

Compound D1

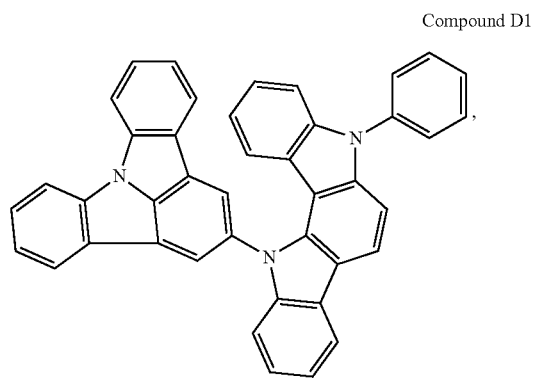

Compound D2

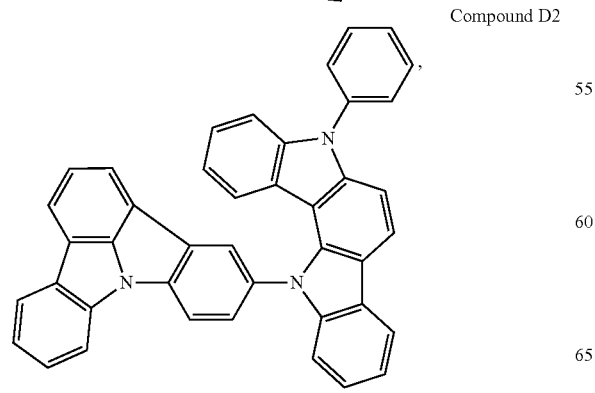

Compound D3

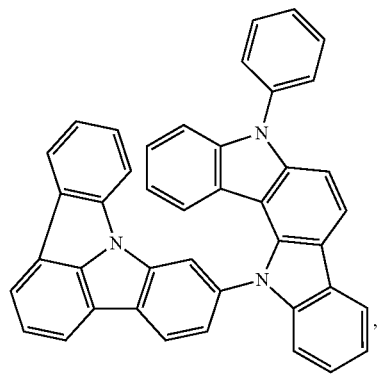

Compound D4

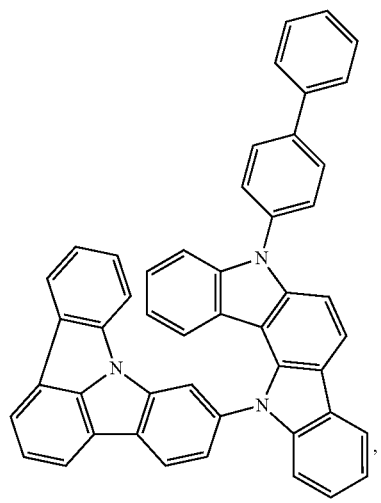

Compound D5

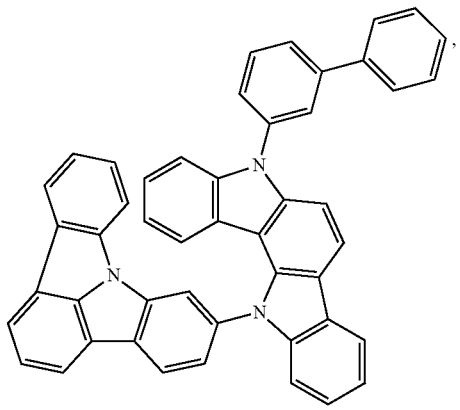

Compound D6
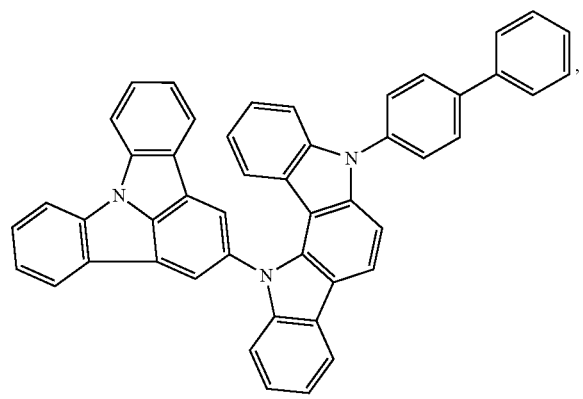
Compound D7
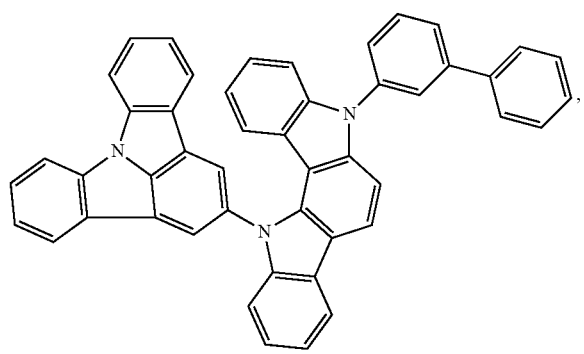
Compound D8
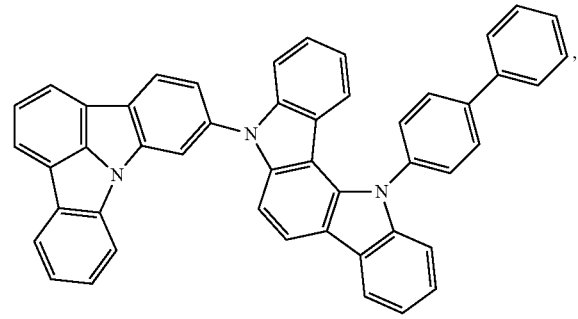
Compound D9
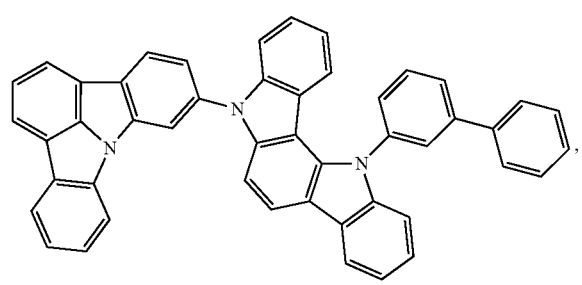
Compound D10
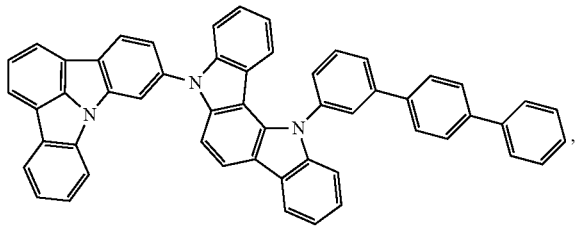
Compound D11
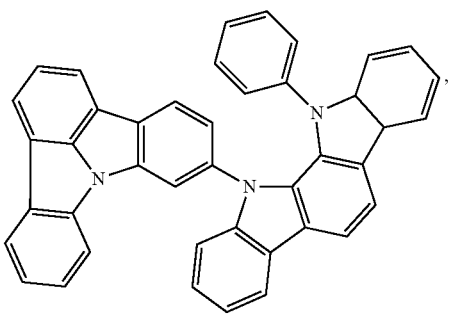
Compound D12
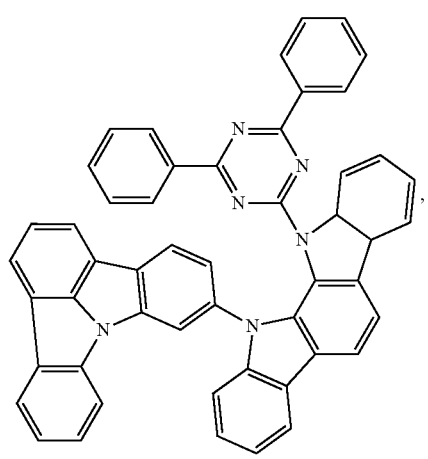
Compound D13
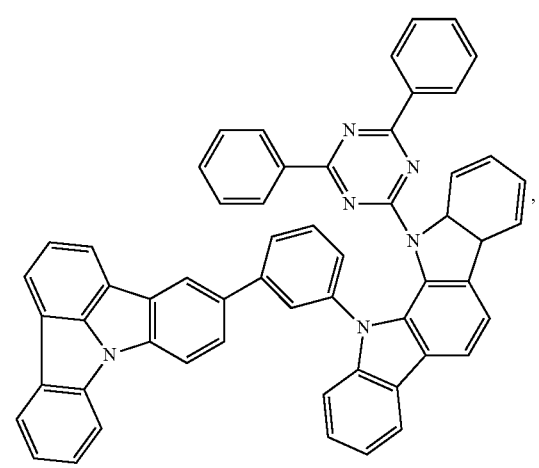

Compound D14
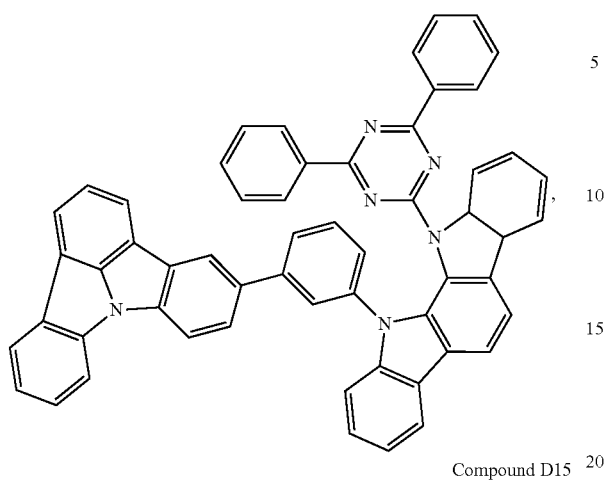
Compound D15
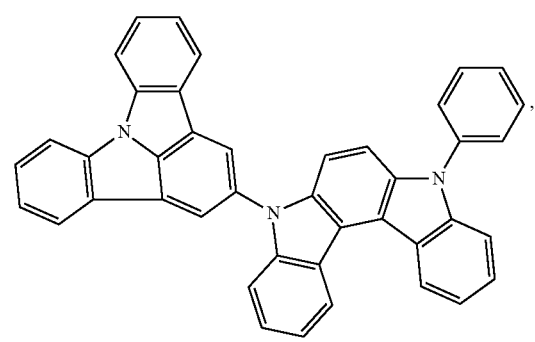
Compound D16
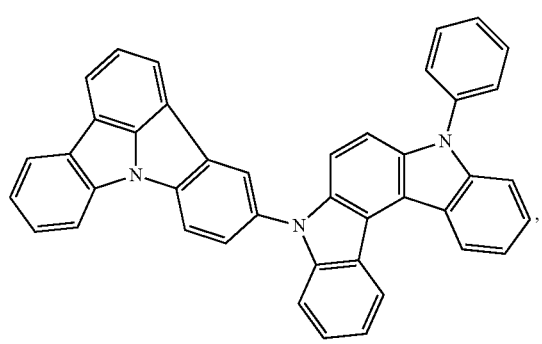
Compound D17
Compound D18
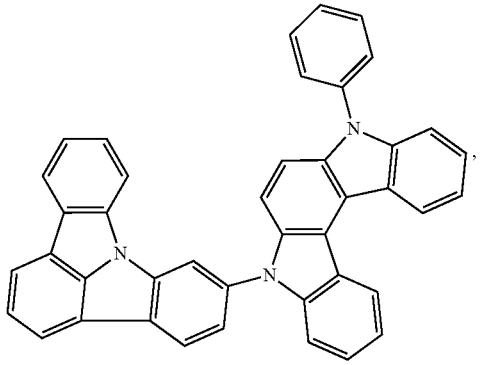
Compound D19
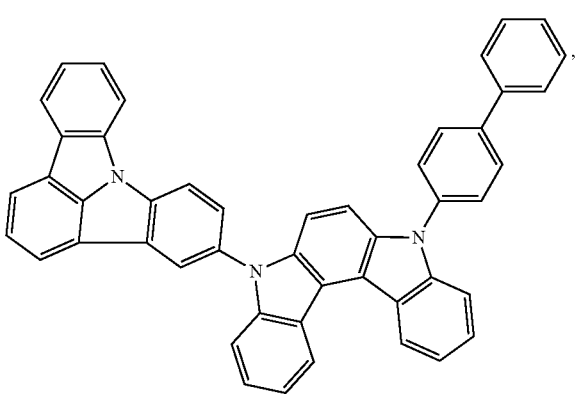
Compound D20
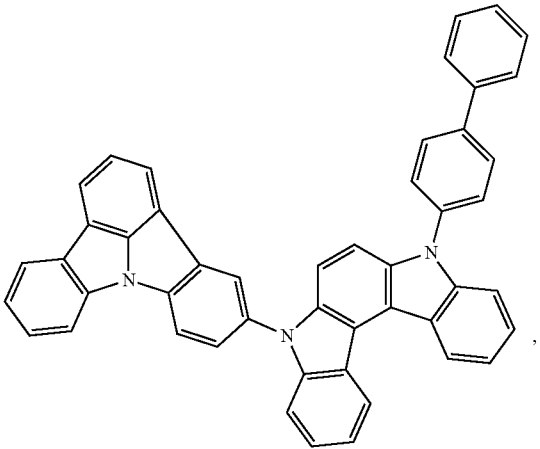

Compound D21
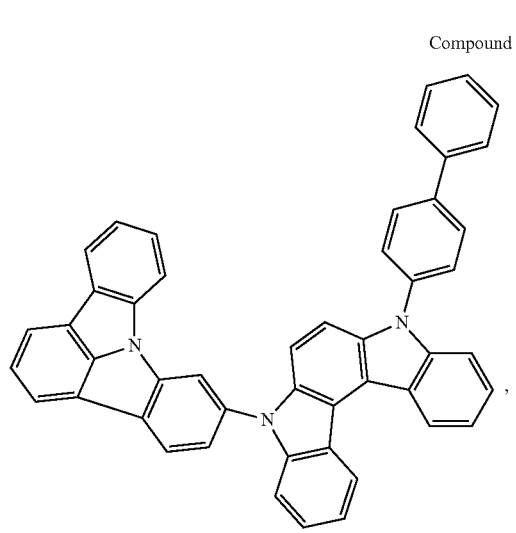
Compound D22
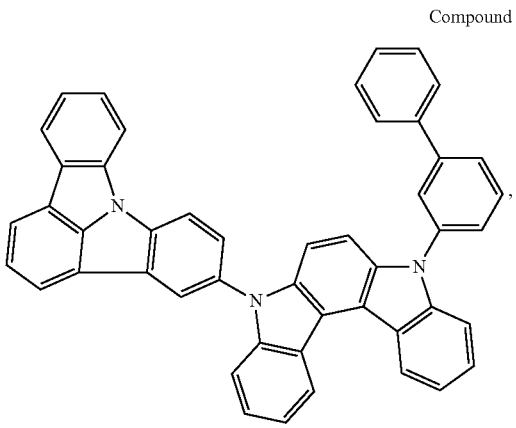
Compound D23
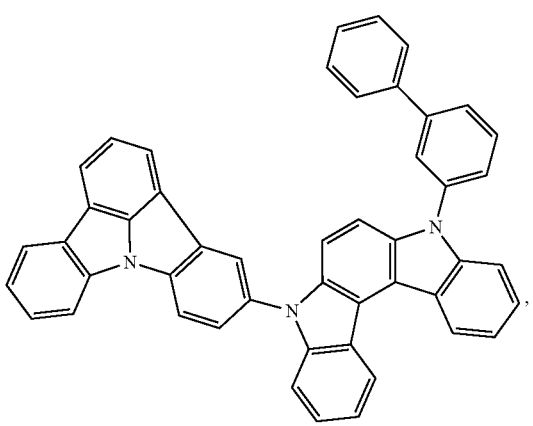
Compound D24
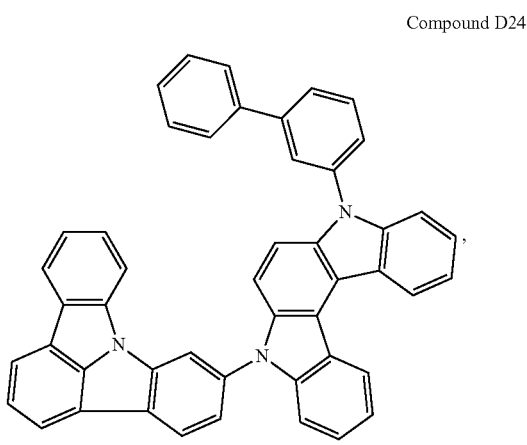
Compound D25
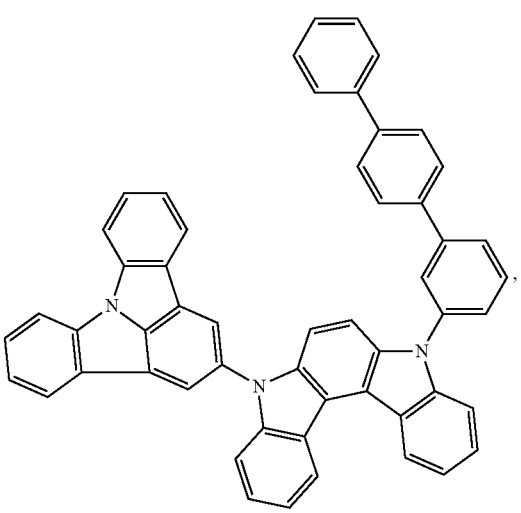
Compound D26
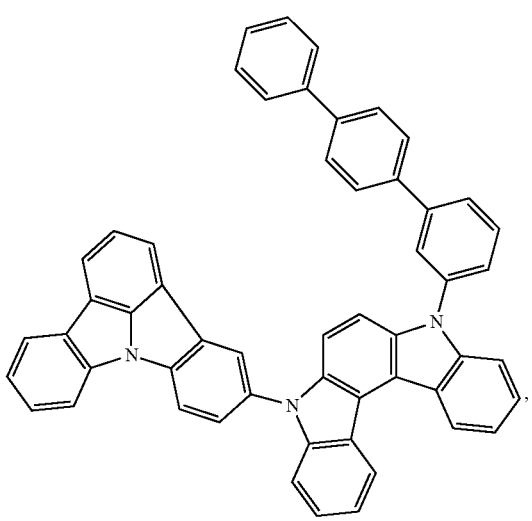

Compound D27
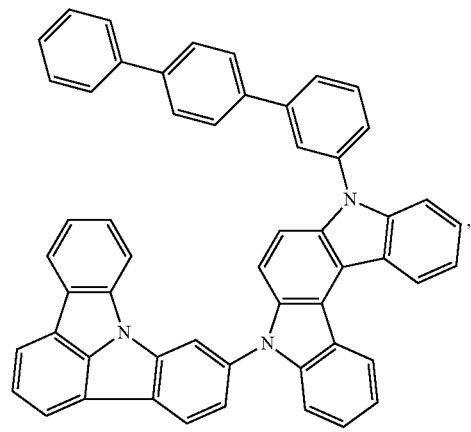
Compound D28
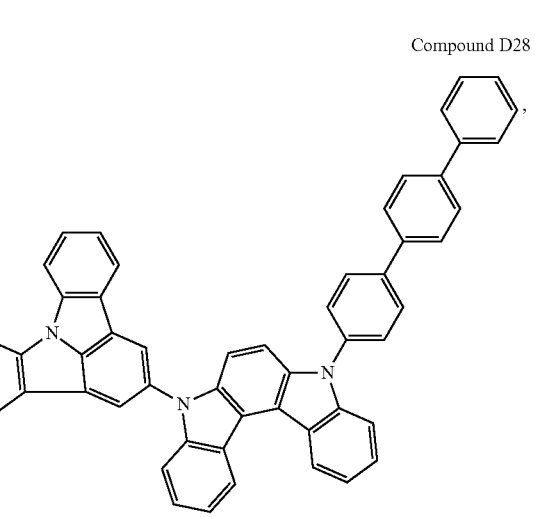
Compound D29
Compound D30
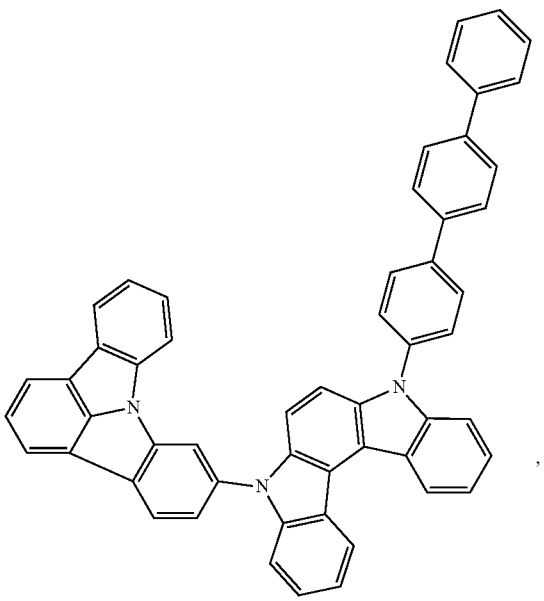
Compound D31
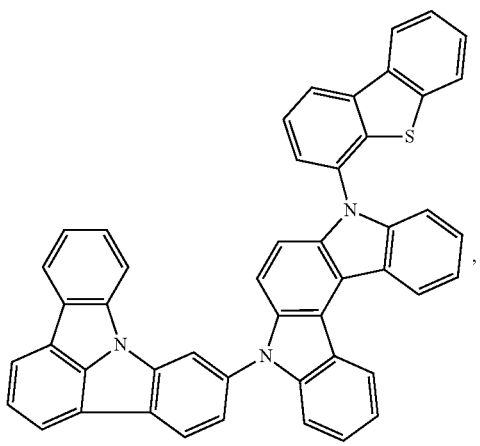
Compound D32
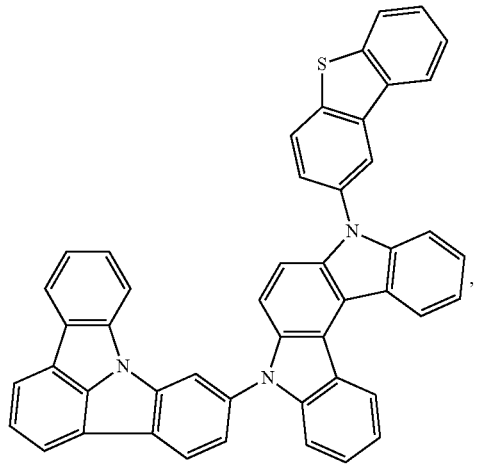

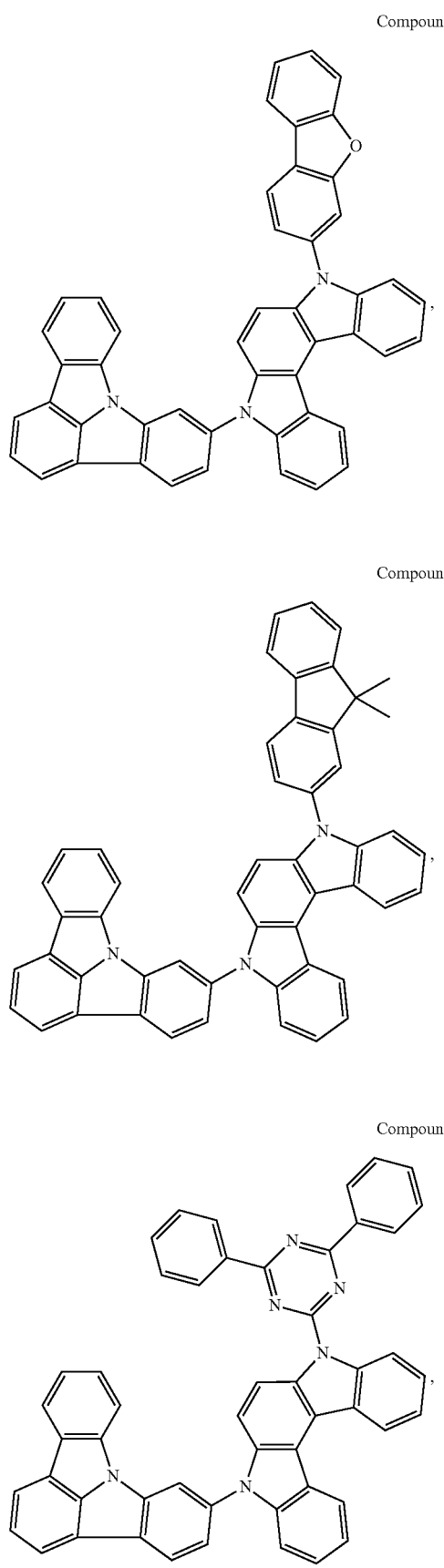
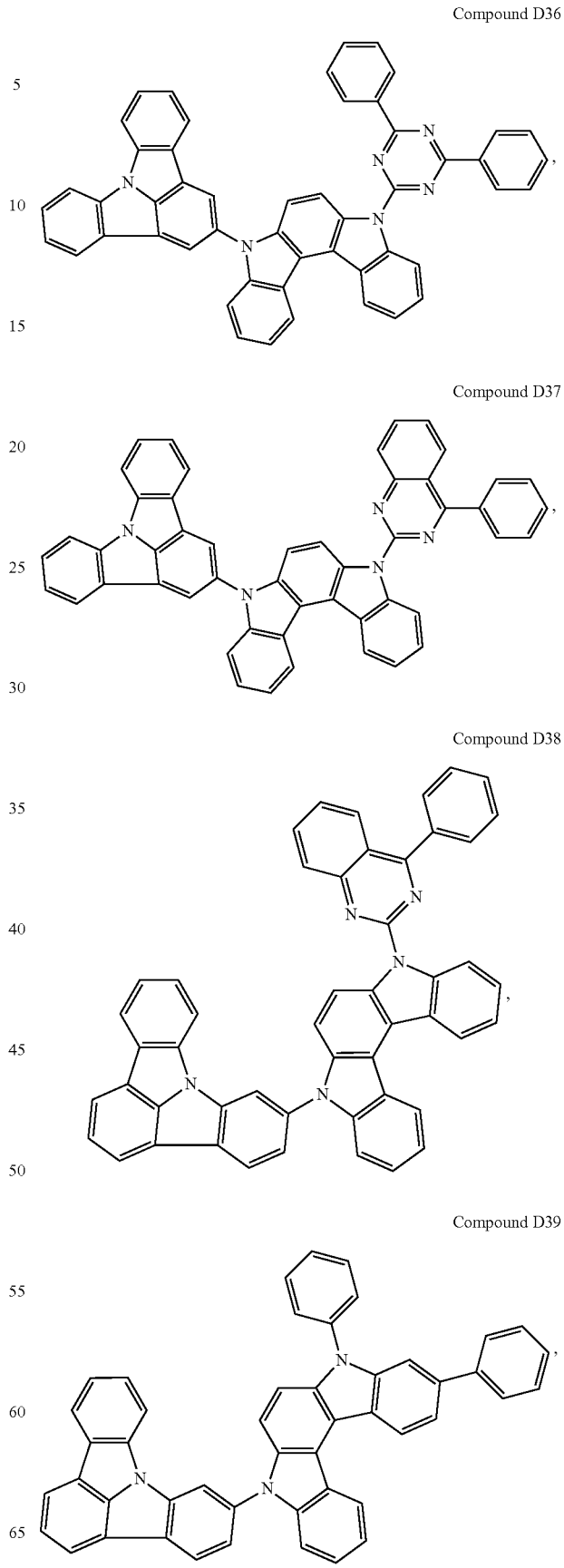

Compound D40
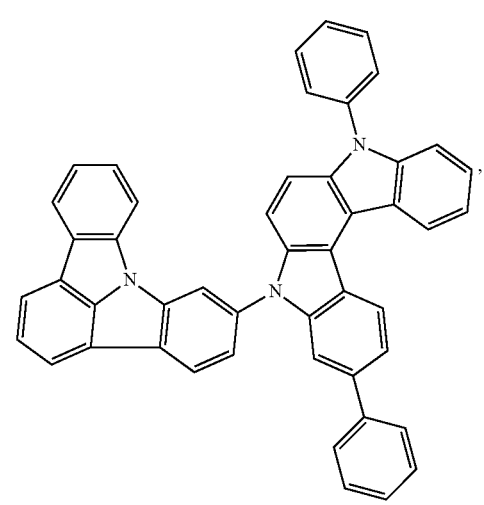
Compound D43
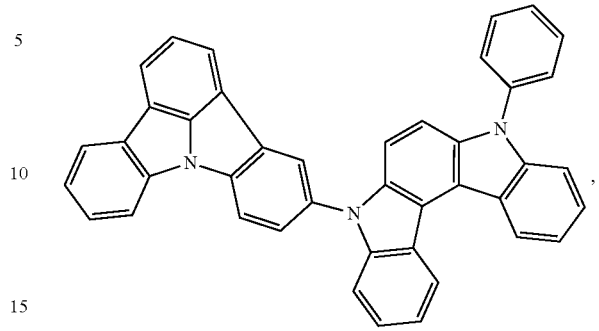
Compound D44
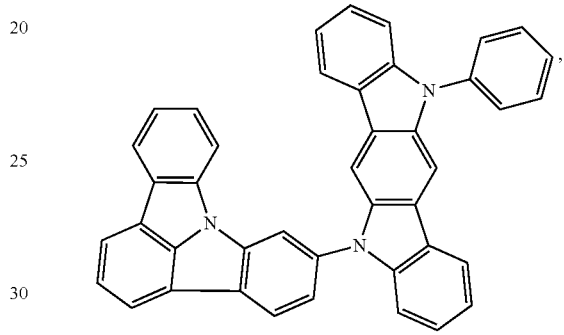
Compound D41
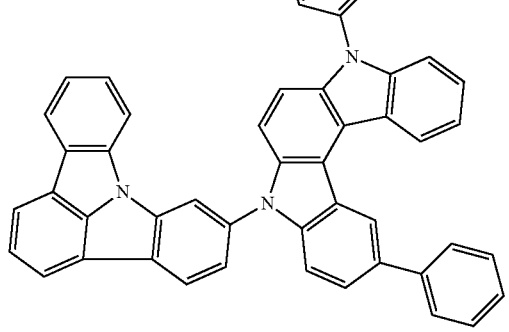
Compound D45
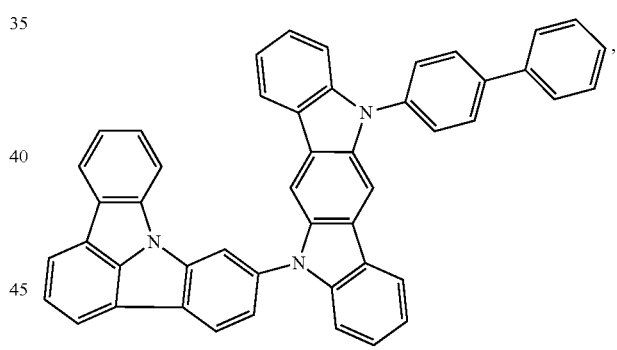
Compound D42
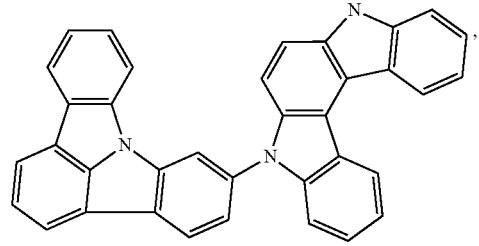
Compounds E1, E2, and E3 each represented by the formula
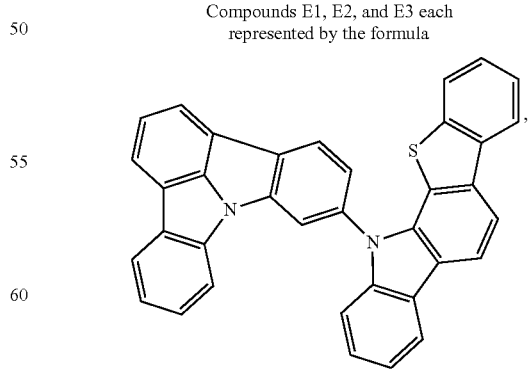
wherein in Compound E1, X = O,
in Compound E2, X = S, and
in Compound E3, X = Se -continued Compounds E4, E5, and E6 each represented by the formula

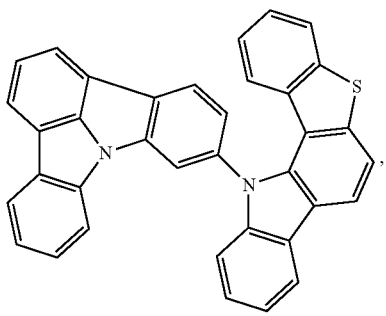

wherein in Compound E4, X = O,
in Compound E5, X = S, and
in Compound E6, X = Se Compounds E7, E8, and E9 each represented by the formula

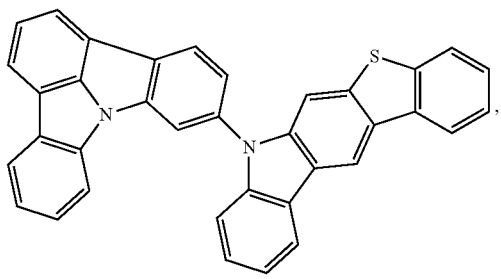

wherein in Compound E7, X = O,
in Compound E8, X = S, and
in Compound E9, X = Se Compounds E10, E11, and E12 each represented by the formula

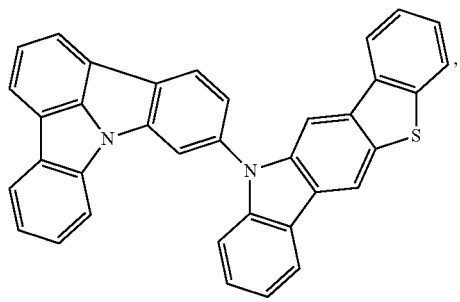

wherein in Compound E10, X = O,
in Compound E11, X = S, and
in Compound E12, X = Se Compounds E13, E14, and E15 each represented by the formula

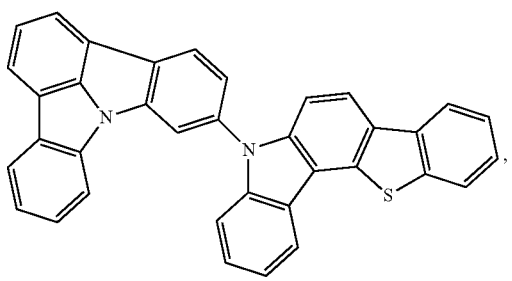

wherein in Compound E13, X = O,
in Compound E14, X = S, and
in Compound E15, X = Se -continued Compounds E16, E17, and E18 each represented by the formula

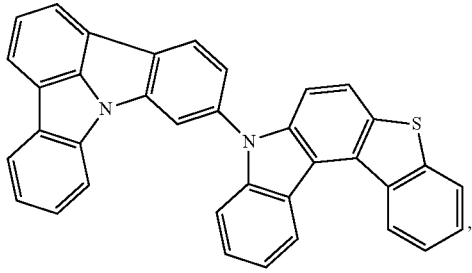

wherein in Compound E16, X = O,
in Compound E17, X = S, and
in Compound E18, X = Se Compound F1

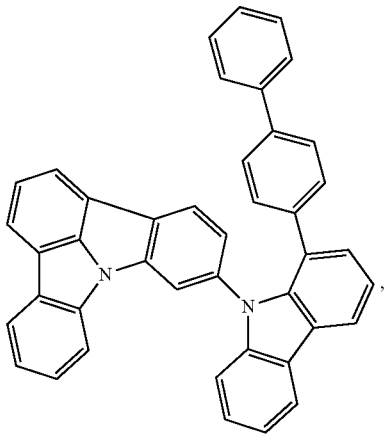

Compound F2

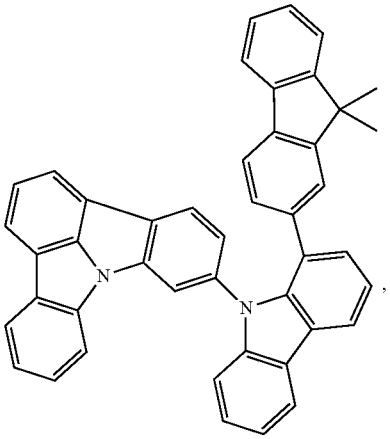

Compound F3

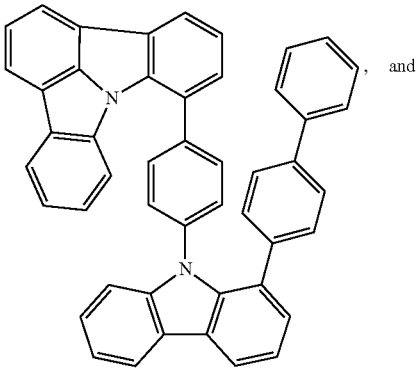, and

Compound F4

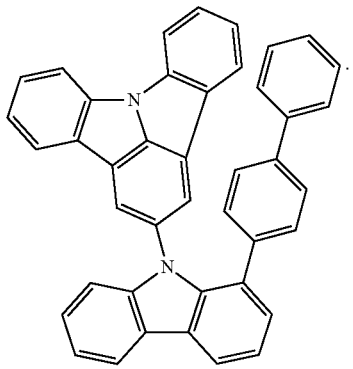

8. A first organic light emitting device comprising:
an anode;
a cathode; and
an organic layer, disposed between the anode and the cathode, comprising a compound having a formula selected from the group consisting of:

Formula I

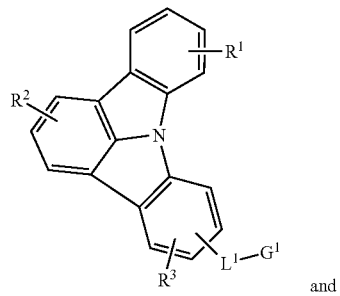

and

Formula II

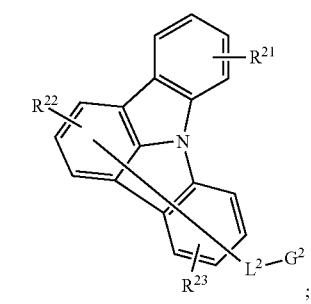

;

wherein $L^1$ is selected from the group consisting of a direct bond, phenyl, biphenyl, terphenyl, fluorene, carbazole, pyridine, pyrimidine, pyrazine, pyridazine, triazine, naphthalene, anthracene, and combinations thereof;

wherein $G^1$ is selected from the group consisting of:

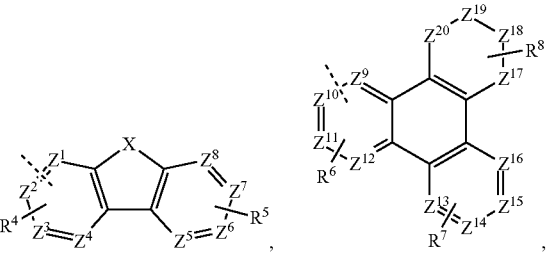
,

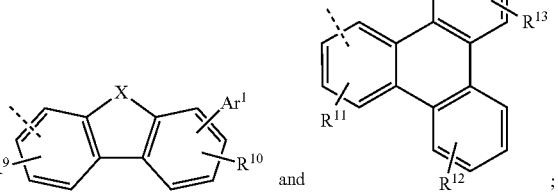

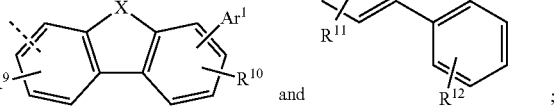

and

;

wherein X is selected from the group consisting of oxygen, sulfur and selenium;
wherein $R^1$, $R^5$, $R^7$, $R^8$, $R^{12}$, $R^{13}$, and $R^{21}$ each independently represent mono, di, tri, or tetra substitution, or no substitution;
wherein $R^2$, $R^3$, $R^4$, $R^5$, $R^6$, $R^9$, $R^{10}$, $R^{11}$, $R^{22}$, and $R^{23}$ each independently represent mono, di, or tri substitution, or no substitution;
wherein $R^1$ to $R^{13}$ and $R^{21}$ to $R^{23}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;
wherein $Z^1$ to $Z^{20}$ are each independently selected from the group consisting of carbon and nitrogen;
wherein at least one of $Z^1$, $Z^2$, $Z^3$, $Z^4$, $Z^5$, $Z^6$, $Z^7$ and $Z^8$ is nitrogen; and at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen;
wherein when any of $Z^1$ to $Z^{20}$ is nitrogen, there is no substitution on that nitrogen;
wherein $L^1$ and $G^1$ are bonded together by a C—C bond;
wherein $Ar^1$ is selected from the group consisting of benzene, biphenyl, terphenyl, triphenylene, fluorene, dibenzofuran, dibenzothiophene, dibenzoselenophene, naphthalene, phenanthrene, carbazole, pyridine, pyrimidine, pyrazine, pyridazine, triazine, azatriphenylene, aza-fluorene, aza-dibenzofuran, aza-dibenzothiophene, aza-dibenzoselenophene, aza-carbazole, quinolone, quinazoline, and combinations thereof;
wherein $L^1$ and $Ar^1$ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, carbazole, pyridine, pyrimidine, pyrazine, pyridazine, triazine, quinolone, phenanthroline, aza-dibenzofuran, aza-dibenzothiophene, aza-dibenzoselenophene, aza-fluorene and aza-triphenylene, aza-carbazole, and combinations thereof;

wherein L² is selected from the group consisting of a direct bond, alkyl, alkoxyl, aryl, heteroaryl, and combinations thereof;

wherein G² is selected from the group consisting of:

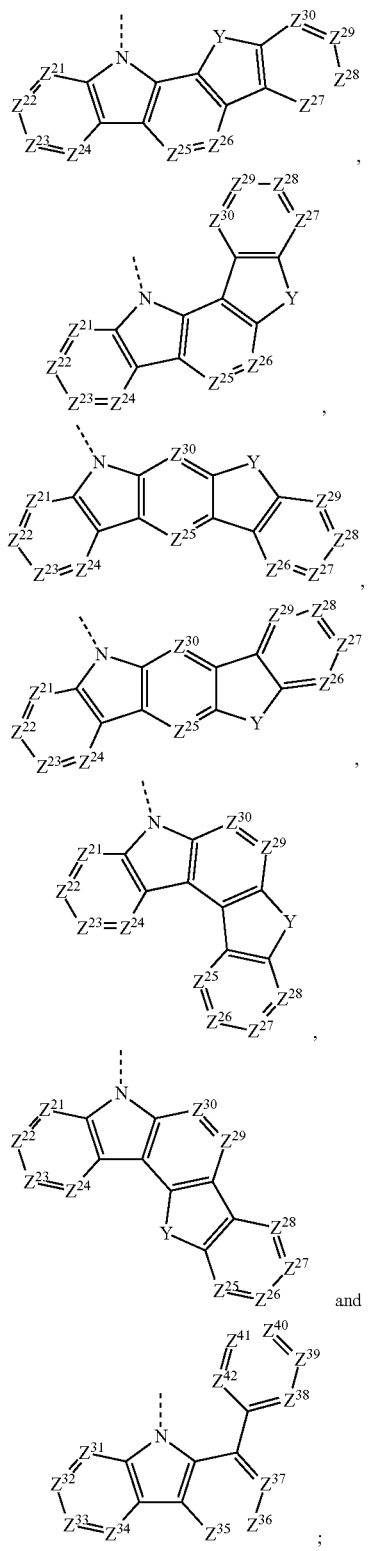

, wherein Z²¹ to Z⁴² are each independently selected from the group consisting of C—R²⁰ and N;

wherein at least one of Z²¹ to Z⁴² is C—R²⁰;

wherein each R²⁰ can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any adjacent substituents are optionally joined to form a ring;

wherein Y is selected from the group consisting of: O, S, Se, BR$^{B1}$, NR$^{B2}$, PR$^{B3}$, and CR$^{B4}$R$^{B5}$;

wherein R$^{B1}$, R$^{B2}$, R$^{B3}$, R$^{B4}$ and R$^{B5}$ are each independently selected from the group consisting of hydrogen, deuterium, alkyl, cycloalkyl, heteroalkyl, arylalkyl, alkoxy, aryloxy, silyl, alkenyl, cycloalkenyl, heteroalkenyl, alkynyl, aryl, heteroaryl, and combinations thereof;

wherein R$^{B4}$ and R$^{B5}$ are optionally jointed to form a ring;

wherein L² is optionally further substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; and wherein the compounds of Formula I and Formula II each contains at most one non-fused carbazole moiety.

9. The first organic light emitting device of claim 8, wherein the organic layer is an emissive layer and the compound of Formula I or Formula II is a host.

10. The first organic light emitting device of claim 8, wherein the organic layer further comprises a phosphorescent emissive dopant; wherein the emissive dopant is a transition metal complex having at least one ligand or part of the ligand if the ligand is more than bidentate selected from the group consisting of:

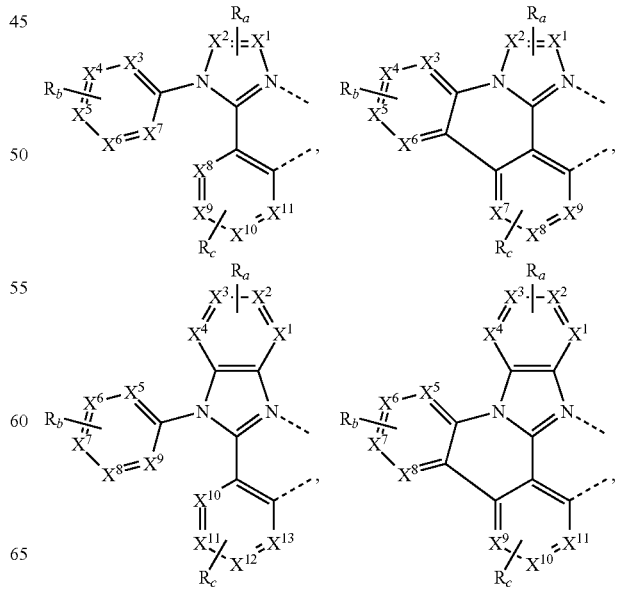

-continued

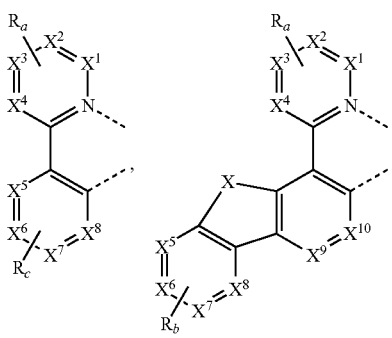

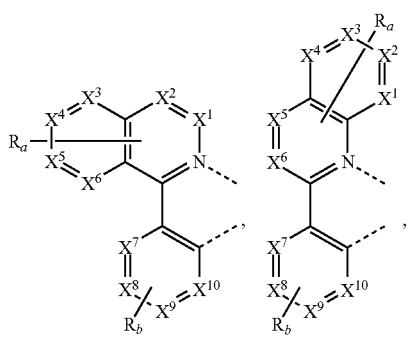

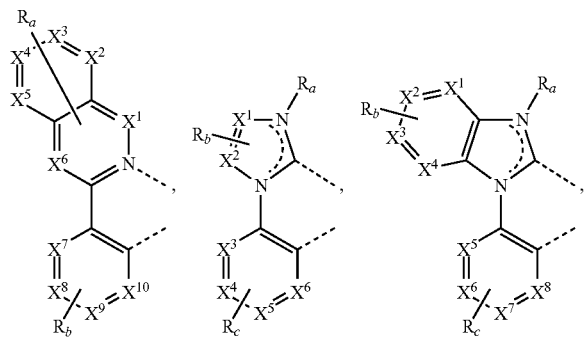

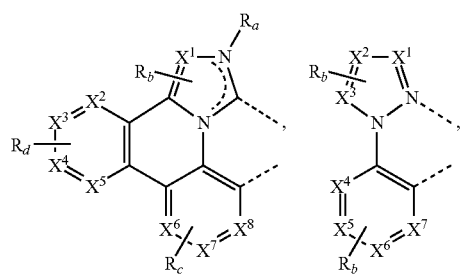

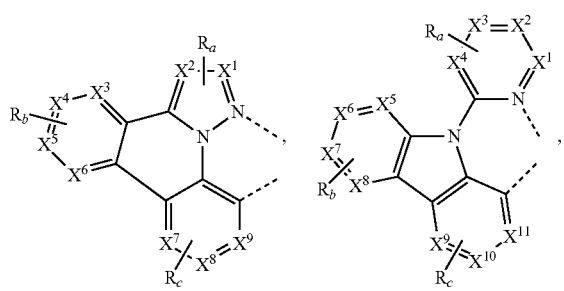

-continued

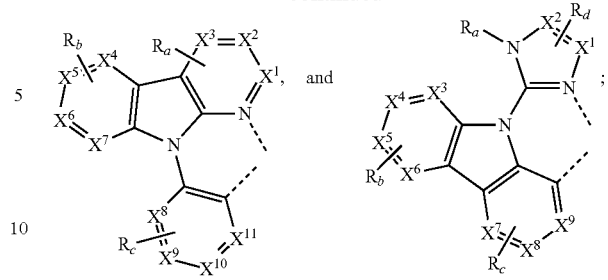

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

11. The first organic light emitting device of claim 8, wherein the organic layer is a blocking layer and the compound having Formula I or Formula II is a blocking material in the organic layer.

12. The first organic light emitting device of claim 8, wherein the organic layer is an electron transporting layer and the compound having Formula I or Formula II is an electron transporting material in the organic layer.

13. The first organic light emitting device of claim 8, wherein the device is incorporated into a device selected from the group consisting of a consumer product, an electronic component module, an organic light-emitting device, and a lighting panel.

14. A formulation comprising a compound having a formula selected from the group consisting of:

Formula I

, and

Formula II

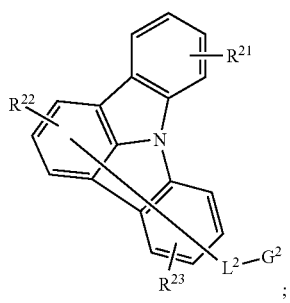

wherein L¹ is selected from the group consisting of a direct bond, phenyl, biphenyl, terphenyl, fluorene, carbazole, pyridine, pyrimidine, pyrazine, pyridazine, triazine, naphthalene, anthracene, and combinations thereof;

wherein G¹ is selected from the group consisting of:

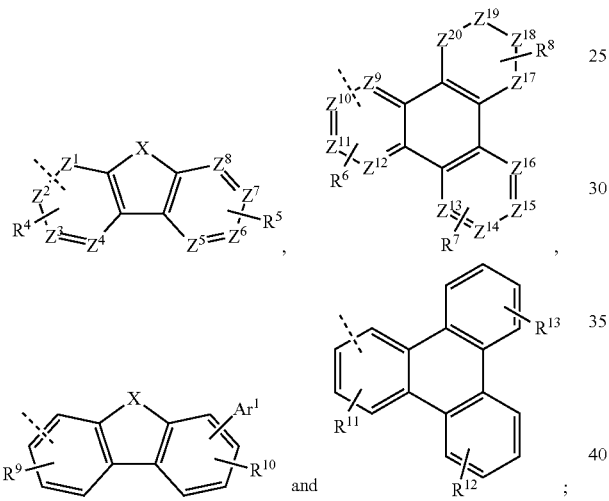

wherein X is selected from the group consisting of oxygen, sulfur and selenium;
wherein $R^1$, $R^5$, $R^7$, $R^8$, $R^{12}$, $R^{13}$, and $R^{21}$ each independently represent mono, di, tri, or tetra substitution, or no substitution;
wherein $R^2$, $R^3$, $R^4$, $R^5$, $R^6$, $R^9$, $R^{10}$, $R^{11}$, $R^{22}$ and $R^{23}$ each independently represent mono, di, or tri substitution, or no substitution;
wherein $R^1$ to $R^{13}$ and $R^{21}$ to $R^{23}$ are each independently selected from the group consisting of hydrogen, deuterium, alkyl, cycloalkyl, alkoxyl, halogen, silyl, nitro, benzene, biphenyl, terphenyl, naphthalene, phenanthrene, benzofuran, benzothiophene, benzoselenophene, dibenzofuran, dibenzothiophene, dibenzoselenophene, fluorene, triphenylene, carbazole, pyridine, pyrimidine, pyrazine, pyridazine, triazine, quinoline, phenanthroline, aza-dibenzofuran, aza-dibenzothiophene, aza-dibenzoselenophene, aza-fluorene, aza-triphenylene, aza-carbazole, and combinations thereof;
wherein $Z^1$ to $Z^{20}$ are each independently selected from the group consisting of carbon and nitrogen;
wherein at least one of $Z^1$, $Z^2$, $Z^3$, $Z^4$, $Z^5$, $Z^6$, $Z^7$ and $Z^8$ is nitrogen; and at least one of $Z^9$, $Z^{10}$, $Z^{11}$, $Z^{12}$, $Z^{13}$, $Z^{14}$, $Z^{15}$, $Z^{16}$, $Z^{17}$, $Z^{18}$, $Z^{19}$ and $Z^{20}$ is nitrogen;
wherein when any of $Z^1$ to $Z^{20}$ is nitrogen, there is no substitution on that nitrogen;
wherein L¹ and G¹ are bonded together by a C—C bond;
wherein Ar¹ is selected from the group consisting of benzene, biphenyl, terphenyl, triphenylene, fluorene, dibenzofuran, dibenzothiophene, dibenzoselenophene, naphthalene, phenanthrene, carbazole, pyridine, pyrimidine, pyrazine, pyridazine, triazine, azatriphenylene, aza-fluorene, aza-dibenzofuran, aza-dibenzothiophene, aza-dibenzoselenophene, aza-carbazole, quinolone, quinazoline, and combinations thereof;
wherein L¹ and Ar¹ are each optionally further substituted with one or more substituents selected from the group consisting of deuterium, alkyl, alkoxyl, halogen, silyl, nitro, benzene, biphenyl, terphenyl, naphthalene, phenanthrene, dibenzofuran, dibenzothiophene, dibenzoselenophene, fluorene, triphenylene, carbazole, pyridine, pyrimidine, pyrazine, pyridazine, triazine, quinolone, phenanthroline, aza-dibenzofuran, aza-dibenzothiophene, aza-dibenzoselenophene, aza-fluorene and aza-triphenylene, aza-carbazole, and combinations thereof;
wherein L² is selected from the group consisting of a direct bond, alkyl, alkoxyl, aryl, heteroaryl, and combinations thereof;
wherein G² is selected from the group consisting of:

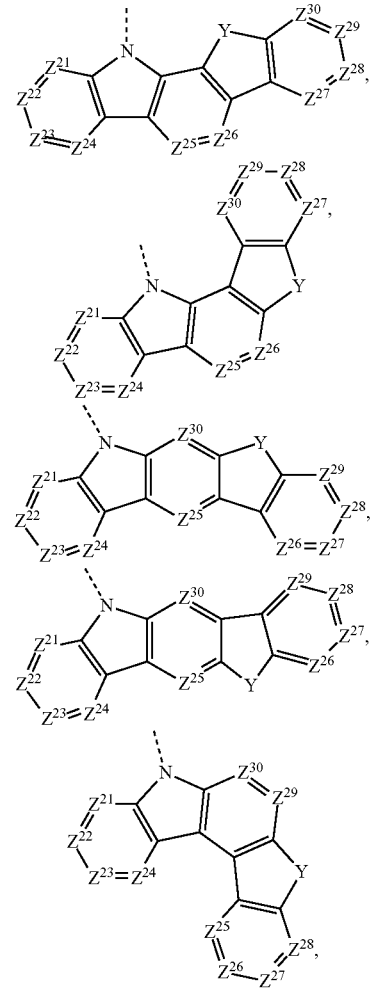

-continued

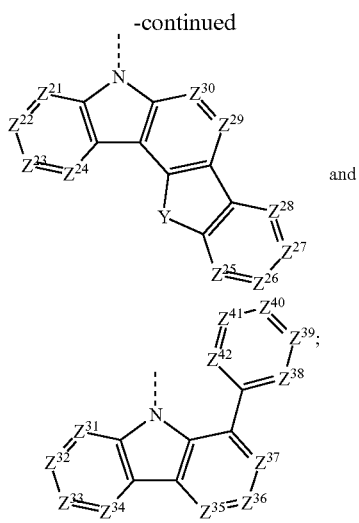

and wherein $Z^{21}$ to $Z^{42}$ are each independently selected from the group consisting of C—$R^{20}$ and N;

wherein at least one of $Z^{21}$ to $Z^{42}$ is C—$R^{20}$;

wherein each $R^{20}$ can be same or different, and is independently selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof;

wherein any adjacent substituents are optionally joined to form a ring;

wherein Y is selected from the group consisting of: O, S, Se, $BR^{B1}$, $NR^{B2}$, $PR^{B3}$, and $CR^{B4}R^{B5}$;

wherein $R^{B1}$, $R^{B2}$, $R^{B3}$, $R^{B4}$ and $R^{B5}$ are each independently selected from the group consisting of hydrogen, deuterium, alkyl, cycloalkyl, heteroalkyl, arylalkyl, alkoxy, aryloxy, silyl, alkenyl, cycloalkenyl, heteroalkenyl, alkynyl, aryl, heteroaryl, and combinations thereof;

wherein $R^{B4}$ and $R^{B5}$ are optionally jointed to form a ring;

wherein $L^2$ is optionally further substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof; and provided that the compound of Formula I and Formula II each contains at most one non-fused carbazole moiety.

15. A formulation comprising the compound in claim 1.

* * * * *